United States Patent
Mueller et al.

(10) Patent No.: US 7,105,517 B2
(45) Date of Patent: Sep. 12, 2006

(54) THIAZOLYL SUBSTITUTED AMINOPYRIMIDINES AS PLANT PROTECTION AGENTS

(75) Inventors: Urs Mueller, Basel (CH); Martin Eberle, Basel (CH); Christian Pillonel, Basel (CH); William Lutz, Basel (CH); Peter Stanetty, Vienna (AT)

(73) Assignee: Syngenta Crop Protection, Inc., Greensboro, NC (US)

( * ) Notice: Subject to any disclaimer, the term of this patent is extended or adjusted under 35 U.S.C. 154(b) by 4 days.

(21) Appl. No.: 10/491,231

(22) PCT Filed: Sep. 19, 2002

(86) PCT No.: PCT/IB02/03868

§ 371 (c)(1),
(2), (4) Date: Sep. 24, 2004

(87) PCT Pub. No.: WO03/029249

PCT Pub. Date: Apr. 10, 2003

(65) Prior Publication Data

US 2005/0038059 A1    Feb. 17, 2005

(30) Foreign Application Priority Data

Oct. 1, 2001 (GB) .................... 0123589.4

(51) Int. Cl.
C07D 417/04 (2006.01)
A01N 43/78 (2006.01)
C07D 277/34 (2006.01)

(52) U.S. Cl. .................. 514/235.8; 514/275; 544/122; 544/331

(58) Field of Classification Search ............... 544/122, 544/331; 514/235.8, 275
See application file for complete search history.

(56) References Cited

U.S. PATENT DOCUMENTS 6,531,479 B1 * 3/2003 Wang et al. .................. 514/275

FOREIGN PATENT DOCUMENTS

DE   19854082   10/1999
WO   02062793    8/2002

* cited by examiner

*Primary Examiner*—Deepak Rao
(74) *Attorney, Agent, or Firm*—Rebecca A. Gegick

(57) ABSTRACT

Compounds of formula (I), or a salt thereof, wherein $R_1$, $R_2$, $R_3$, $R_4$, $R_5$, $R_6$, $R_7$, and $R_8$ are specified organic redicals; and compositions containing them, processes for making them and their use as fungicides.

(I)

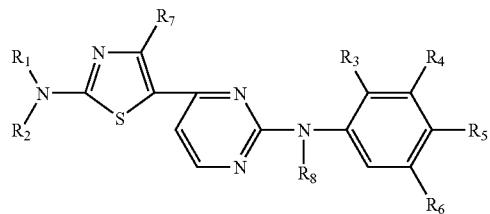

11 Claims, No Drawings

THIAZOLYL SUBSTITUTED AMINOPYRIMIDINES AS PLANT PROTECTION AGENTS

This application is a 371 of PCT/IB02/03868 filed Sep. 19, 2002.

The present invention relates to novel N-[4-(2-amino-thiazol-5-yl)-pyrimidin-2-yl]-N-phenyl-amine derivatives, to a method of protecting plants against attack or infestation by phytopathogenic organisms, such as nematodes or insects or especially microorganisms, preferably fungi, bacteria and viruses, or combinations of two or more of these organisms, by applying an N-[4-(2-amino-thiazol-5-yl)-pyrimidin-2-yl]-N-phenyl-amine derivative as specified hereinafter to a part and/or to the site of a plant, to the use of said derivative for protecting plants against said organisms, and to compositions comprising said derivative as the active component. The invention further relates to the preparation of these novel N-[4-(2-amino-thiazol-5-yl)-pyrimidin-2-yl]-N-phenyl-amine derivatives.

Certain N-phenyl-N-(4-thiazolyl-pyrimidin-2-yl)-amine derivatives have been described in the art, e.g. in the PCT patent applications WO 97/19065, WO 01/29009 and WO 01/30778, as having pharmacological properties, mainly as tumor-inhibiting anti-cancer substances.

Surprisingly, it has now been found that the new N-[4-(2-amino-thiazol-5-yl)-pyrimidin-2-yl]-N-phenyl-amine derivatives according to the present invention are effective in plant protection showing advantageous properties in the treatment of plant diseases caused by phytopathogenic microorganisms. Further the fungicidal activity allows to employ the compounds according to present invention for controlling fungi in related areas, e.g. in protection of technical materials, including wood and wood related technical products, in food storage, in hygiene management, etc.

The novel N-[4-(2-amino-thiazol-5-yl)-pyrimidin-2-yl]-N-phenyl-amine derivatives according to the invention are those of the formula I

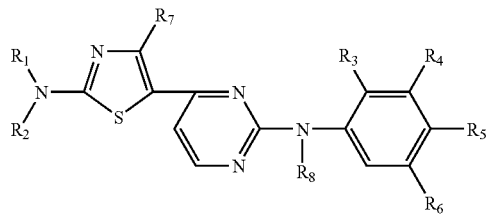

(I)

wherein
$R_1$ is hydrogen, $C_1$–$C_6$alkyl, $C_2$–$C_6$alkenyl, $C_3$–$C_7$cycloalkyl, $C_3$–$C_7$cycloalkyl-$C_1$–$C_4$alkyl, $C_1$–$C_4$alkyl-$C_3$–$C_7$cycloalkyl-$C_1$–$C_4$alkyl, $C_1$–$C_6$haloalkyl, $C_1$–$C_6$hydroxyalkyl, $C_1$–$C_4$alkoxy-$C_1$–$C_6$alkyl, $C_1$–$C_6$aminoalkyl, $C_1$–$C_4$alkyl-$C_1$–$C_6$aminoalkyl, di($C_1$–$C_4$alkyl)-$C_1$–$C_6$aminoalkyl, aryl-$C_1$–$C_4$alkyl, heteroaryl-$C_1$–$C_4$alkyl, or a group —CO—$R_9$, —CO—$OR_{10}$, —CO—$NR_{10}R_{11}$, or —$NR_{10}R_{11}$;
$R_2$ is hydrogen, $C_1$–$C_6$alkyl, $C_1$–$C_6$haloalkyl, $C_1$–$C_6$hydroxyalkyl, $C_1$–$C_4$alkoxy-$C_1$–$C_6$alkyl, $C_1$–$C_6$aminoalkyl, $C_1$–$C_4$alkyl-$C_1$–$C_6$aminoalkyl or a group —CO—$R_9$;
$R_1$ and $R_2$ together with the nitrogen to which they are bound form an optionally substituted N-linked saturated or unsaturated N-ring system which may contain oxygen or sulfur as a ring member, or form a group —N=$CR_9$—$NR_{10}R_{11}$;
$R_3$ is hydrogen, halogen or $C_1$–$C_4$alkyl;
$R_4$ is hydrogen, $C_1$–$C_6$alkyl, $C_1$–$C_6$haloalkyl, $C_1$–$C_6$cyanoalkyl, $C_3$–$C_7$cycloalkyl, $C_2$–$C_6$alkenyl, $C_2$–$C_6$haloalkenyl, $C_2$–$C_6$alkynyl, $C_2$–$C_6$haloalkynyl, amino, $C_1$–$C_6$alkylamino, di($C_1$–$C_4$alkyl)-amino, halogen, hydroxy, mercapto, cyano, $C_1$–$C_6$alkoxy, $C_2$–$C_6$alkenyloxy, $C_2$–$C_6$alkynyloxy, $C_1$–$C_6$haloalkoxy, $C_1$–$C_8$alkanoyloxy-$C_1$–$C_6$alkyl, $C_1$–$C_6$alkylthio, $C_1$–$C_6$alkylsulfinyl, $C_1$–$C_6$alkylsulfonyl, $C_1$–$C_6$hydroxyalkyl, $C_1$–$C_4$alkoxy-$C_1$–$C_6$alkyl, $C_1$–$C_6$aminoalkyl, $C_1$–$C_4$alkyl-$C_1$–$C_6$aminoalkyl, di($C_1$–$C_4$alkyl)-$C_1$–$C_6$aminoalkyl, $C_1$–$C_8$alkoxycarbonyl, $C_1$–$C_8$alkanoyl-$C_1$–$C_6$aminoalkyl, optionally substituted heterocyclyl, optionally substituted aryl, optionally substituted heteroaryl, or a group —CO—$R_9$, —O—CO—$R_9$, —NH—CO—$R_9$, —($C_1$–$C_6$alkylene-)-CO—$R_9$, —C(—O—$C_1$–$C_6$alkylene-O—)—$R_9$, —C(=N$OR_8$)—$R_9$ or —CO—$NR_{10}R_{11}$;
$R_5$ is hydrogen, hydroxy, halogen, $C_1$–$C_6$alkyl, $C_1$–$C_6$alkoxy or $C_1$–$C_6$haloalkyl;
$R_6$ is hydrogen, $C_1$–$C_6$alkyl or $C_1$–$C_6$haloalkyl;
$R_7$ is thienyl, pyridinyl or aryl each optionally substituted with one to three substituents independently selected from the group comprising halogen, $C_1$–$C_4$alkyl, $C_1$–$C_4$alkoxy, $C_1$–$C_4$haloalkyl and $C_1$–$C_4$haloalkoxy;
$R_8$ is hydrogen, $C_1$–$C_6$alkyl, $C_2$–$C_6$alkenyl, $C_2$–$C_6$alkynyl, $C_1$–$C_4$alkoxy-$C_1$–$C_6$alkyl, or a group —CO—$R_9$ or —CO—$OR_{10}$;
$R_9$ is hydrogen, $C_1$–$C_6$alkyl, $C_1$–$C_6$haloalkyl, $C_3$–$C_7$cycloalkyl, $C_3$–$C_7$cycloalkyl-$C_1$–$C_4$alkyl, aryl, $C_1$–$C_4$alkyl-$C_3$–$C_7$cycloalkyl-$C_1$–$C_4$alkyl, aryl-$C_1$–$C_4$alkyl, heteroaryl or heteroaryl-$C_1$–$C_4$alkyl;
$R_{10}$ is $C_1$–$C_6$alkyl, $C_1$–$C_6$haloalkyl, $C_3$–$C_7$cycloalkyl-$C_1$–$C_4$alkyl or $C_1$–$C_4$alkoxy-$C_1$–$C_6$alkyl;
$R_{11}$ is $C_1$–$C_6$alkyl, $C_3$–$C_7$cycloalkyl, $C_3$–$C_7$cycloalkyl-$C_1$–$C_4$alkyl, $C_1$–$C_4$alkoxy-$C_1$–$C_6$alkyl, aryl or heteroaryl; or a salt thereof.

The symbols and generic expressions used above are defined as below. Where radicals are combined from other sub-radicals, the definition of resulting new radical likewise follows from the combination of the definitions of said sub-radicals.

In this document "halogen" or the prefix "halo" shall include fluorine, chlorine, bromine and iodine. Preferably, this definition designates substitution with fluorine or chlorine.

Alkyl—as a group per se and as a structural element of hydroxyalkyl, aminoalkyl, dialkylamino, cycloalkylalkyl, alkoxy, alkoxyalkyl, alkylthio, alkylsulfinyl, alkylsulfonyl, alkenyl, alkynyl, alkenyloxy, alkynyloxy, alkylene, alkanoyl, alkanoyloxy, alkanoylamino, arylalkyl, heteroarylalkyl, haloalkyl or haloalkoxy—is preferably $C_1$–$C_6$alkyl, more preferably $C_1$–$C_4$alkyl. The alkyl, alkenyl and alkynyl radicals may be straight-chain or branched. This applies also to the alkyl, alkenyl or alkynyl parts of other alkyl-, alkenyl- or alkynyl-containing groups. Depending upon the number of carbon atoms mentioned, alkyl on its own or as part of another substituent is to be understood as being, for example, methyl, ethyl, propyl, butyl, pentyl, hexyl, heptyl, octyl and the isomers thereof, for example isopropyl, isobutyl, tert-butyl or sec-butyl, isopentyl or tert-pentyl. In many cases the short chain alkyl groups methyl or ethyl are preferred.

Alkoxy includes methoxy, ethoxy, propyloxy, isopropyloxy, butoxy, isobutyloxy, sec-butyloxy, tert-butyloxy, and the diverse pentyloxy and hexyloxy.

Depending upon the number of carbon atoms mentioned, alkenyl as a group or as a structural element of other groups is to be understood as being, for example, ethenyl, allyl, 1-propen-1-yl, 2-propen-1-yl, 1-propen-3-yl, 1-buten-2-yl, 1-buten-3-yl, 1-penten-1-yl, 2-penten-1-yl, 1-penten-3-yl, hexen-1-yl, 4-methyl-3-pentenyl or 4-methyl-3-hexenyl. Optionally substituted alkenyl groups carry one to four, preferably not more than two further substituents selected from the group halogen, $C_1$–$C_4$alkoxy, $C_1$–$C_4$alkylthio, phenyl, halophenyl, $C_1$–$C_4$alkylphenyl, benzyl, halobenzyl and $C_1$–$C_4$alkylbenzyl. Examples are stryryl, chloroallyl, dichloroallyl, trichlorovinyl, 4,4,4-trifluoro-2-butenyl.

Alkynyl as a group or as a structural element of other groups is for example, ethynyl, propyn-1-yl, propyn-2-yl, butyn-1-yl, butyn-2-yl, 1-methyl-2-butynyl, hexyn-1-yl, 1-ethyl-2-butynyl or octyn-1-yl. Optionally substituted alkynyl groups carry one to four, preferably not more than two further substituents selected from the group halogen, $C_1$–$C_4$alkoxy, $C_1$–$C_4$alkylthio, phenyl, halophenyl, $C_1$–$C_4$alkylphenyl, amino, $C_1$–$C_4$alkylamino, di-($C_1$–$C_4$alkyl)-amino, benzyl, halobenzyl and $C_1$–$C_4$alkylbenzyl. Examples are phenylethinyl, phenylpropargyl, chloropropargyl or 5,5,5-trifluoro-2-pentinyl.

Alkenyloxy and alkynyloxy have analogous designations, employing the exemplified alkenyl and alkynyl radicals.

Alkylene designates a bivalent bridge member, being linked at both ends of the hydrocarbon chain, which may be straight or branched. Typical examples are methylene, 1,2-ethylene, 1-methyl-1,2-ethylene, 1,2-dimethyl-1,2-ethylene, 1,1-dimethyl-1,2-ethylene, 1-ethyl-1,2-ethylene, 1-propyl-1,2-ethylene, 1-butyl-1,2-ethylene, 1,3-propylene, etc. Where alkylene is attached to two oxygen atoms at both ends, and both oxygen atoms are in turn bound to the same carbon atom as in the definition of $R_4$, then the functional group is that of a ketal.

Cycloalkyl is, depending upon the number of carbon atoms mentioned, cyclopropyl, cyclobutyl, cyclopentyl, cyclohexyl, bicyclopentyl, bicyclohexyl or cycloheptyl. Likewise, cycloalkyl-alkyl or alkyl-cycloalkyl-alkyl encompass cyclopropylmethyl, cyclopropylethyl, cyclopentylmethyl, cyclohexylmethyl, cyclopentylethyl, cyclohexylethyl, methyl-cyclopropylmethyl, methyl-cyclopropylethyl, dimethyl-cyclopropylmethyl, dimethyl-cyclopropylethyl, methyl-cyclopentylmethyl, methyl-cyclohexylmethyl, methyl-cyclopentylethyl, methyl-cyclohexylethyl, ethyl-cyclopentylmethyl, ethyl-cyclohexylmethyl, ethyl-cyclopentylethyl, ethyl-cyclohexylethyl, dimethyl-cyclopentylmethyl, dimethyl-cyclohexylmethyl, dimethyl-cyclopentylethyl or dimethyl-cyclohexylethyl, etc.

Hydroxyalkyl preferably encompasses hydroxymethyl, 1-hydroxyethyl, 1-hydroxypropyl, 2-hydroxyethyl, 2-hydroxypropyl, 2-hydroxy-2-methyl-ethyl, 3-hydroxypropyl and various hydroxybutyl radicals.

Alkoxyalkyl is meant to include without limiting the definition thereof: methoxymethyl, ethoxymethyl, propyloxymethyl, isopropyloxymethyl, butyloxymethyl, 2-methoxyethyl, 2-ethoxyethyl, 2-propyloxyethyl, 2-isopropyloxyethyl, 2-butyloxyethyl, 1-methoxyethyl, 1-ethoxyethyl, 1-propyloxyethyl, 1-isopropyloxyethyl, 1-butyloxyethyl, 1-methoxypropyl, 1-ethoxypropyl, 1-propyloxypropyl, 1-isopropyloxypropyl, 1-butyloxypropyl, 2-methoxypropyl, 2-ethoxypropyl, 2-propyloxypropyl, 2-isopyropyloxypropyl, 2-butyloxypropyl, 3-methoxypropyl, 3-ethoxypropyl, 3-propyloxypropyl, 3-isopropyloxypropyl, 3-butyloxypropyl, methoxybutyl, ethoxybutyl, propyloxybutyl, and butyloxybutyl.

Alkoxycarbonyl is for example: methoxycarbonyl, ethoxycarbonyl, propyloxycarbonyl, isopropyloxycarbonyl, butyloxycarbonyl, s-butyloxycarbonyl, or terbutyloxycarbonyl.

Within this document alkanoyl includes the aliphatic acyl radicals, e.g. formyl, acetyl, propionyl, isopropionyl, butyryl, isobutyryl, sec-butyryl, tert-butyryl, valeryl, isovaleryl, sec-valeryl and pivaloyl. These radicals are frequently employed in the alkanoyloxyalkyl and alkanoylaminoalkyl groups as defined for this invention.

Aminoalkyl includes aminomethyl, aminoethyl, aminopropyl, aminobutyl and the isomeric forms thereof. Likewise alkylaminoalkyl and dialkylaminoalkyl include for example methylaminomethyl, ethylaminomethyl, propylaminomethyl, methylaminoethyl, ethylaminoethyl, propylaminoethyl, methylaminopropyl, ethylaminopropyl, dimethylaminomethyl, dimethylaminoethyl, dimethylaminopropyl, ethyl-methylaminomethyl, ethyl-methylaminoethyl, ethyl-methylaminomethyl, ethyl-methylaminopropyl, etc.

Haloalkyl includes halogenated alkyl, preferably based on $C_1$–$C_6$haloalkyl, more preferably on $C_1$–$C_4$alkyl, which is linear or branched, and is substituted by one or more, for example in case of substitution with halogen atoms all hydrogens of the basic hydrocarbon structure may be replaced by halogen atoms, being all identical or different. Typical examples are $CHCl_2$, $CH_2F$, $CCl_3$, $CH_2Cl$, $CHF_2$, $CF_3$, $CH_2CH_2Br$, $C_2Cl_5$, $CH_2Br$, $CHClBr$, $CF_3CH_2$, $C_2F_5$, $C_3F_7$, $C_4F_9$, $C_5F_{11}$, $CH_2CH_2Cl$, $CH(CH_3)$—$CH_2$—$CH_2Cl$, $CH_2CH_2F$, $CH(CH_3)$—$CH_2$—$CH_2F$, $C(CH_3)_2$—$CH_2$—$Cl$, $C(CH_3)_2$—$CH_2$—$CF_3$, $C(CH_3)$—$CH_2$—$CH_2$—$CF_3$, etc.

Haloalkoxy includes halogenated alkoxy which preferably based on $C_1$–$C_6$alkoxy, more preferably on $C_1$–$C_4$alkoxy, which is linear or branched, and is substituted by one or more, for example in the case of halo-ethyl up to five halogen atoms. Especially fluorine is preferred as a halogen substituent in alkoxy groups, including trifluoromethoxy and 1,1,2,2-tetrafluoroethoxy as prominent members.

Cyanoalkyl includes without limiting the definition thereof: cyanomethyl, 1-cyanoethyl, 2-cyanoethyl, 1-cyanopropyl, 2-cyanopropyl, 3-cyanopropyl, 1-cyanoisopropyl, 2-cyanoisopropyl, the isomeric cyanobutyl, cyanopentyl and cyanohexyl. Cyanomethyl and cyanoethyl are preferred.

Aryl typically includes aromatic hydrocarbon rings such as phenyl, naphthyl, anthracenyl, phenanthrenyl and biphenyl, for example 1,3-biphenyl and 1,4-biphenyl, with phenyl being preferred. The same definition applies where aryl is part of arylalkyl.

The most prominent examples for arylalkyl are benzyl and phenethyl.

Heteroaryl includes aromatic ring systems comprising mono-, bi- or tricyclic systems wherein at least one oxygen, nitrogen or sulfur atom is present as a ring member. The same definition applies where heteroaryl is part of heteroarylalkyl. Examples are of heteroaryl rings are furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothiophenyl, benzofuranyl, benzimidazolyl, indazolyl, benzotriazolyl, benzothiazolyl, benzoxazolyl, quinolinyl, isoquinolinyl, phthalazinyl, quinoxalinyl, quinazolinyl, cinnolinyl and naphthyridinyl.

The heteroaryl group may be bonded to the basic molecular structure of formula I via a carbon or a nitrogen atom.

Heterocyclyl designates fully or partially hydrogenated heteroaryl ring system as outlined above. Typical examples include 2-tetrahydrofuranyl, 3-tetrahydrofuranyl, 5-hydroxy-tetrathydrofuran-2-yl, 2-isoxazolinyl, 3-isoxazolinyl, 4-isoxazolinyl, 5-isoxazolinyl, pyrrolidin-2-on-5-yl, N-pyrrolidinyl, 2-pyrrolidinyl, 2-pyrrolin-5-yl, etc.

Where the above aryl and heteroaryl groups may be optionally substituted, this means that they may carry one or more identical or different substituents. Normally not more than three substituents are present at the same time. Examples of substituents of aryl or heteroaryl groups are: amino, $C_1$–$C_4$alkylamino, di-$C_1$–$C_4$alkylamino, halogen, hydroxy, mercapto, cyano, $C_1$–$C_6$alkyl, $C_1$–$C_6$alkoxy, $C_1$–$C_6$alkylthio, $C_1$–$C_6$alkylsulfinyl, $C_1$–$C_6$alkylsulfonyl, $C_2$–$C_6$al-kenyloxy and $C_2$–$C_6$alkynyloxy.

Typical examples for substituted aryl include 4-chlorophenyl, 4-bromophenyl, 3,4-dichlorophenyl, 4-chloro-3-fluorophenyl, 3-chloro-4-fluorophenyl, 4-methylphenyl, 4-ethylphenyl, 4-propargyloxyphenyl, 4-allyloxyphenyl, 3,4-dioxomethylenyl-phenyl, 3,4-dioxoethylenyl-phenyl, 3-methylphenyl, 4-fluorophenyl, 4-ethenylphenyl, 4-ethynylphenyl, 4-propylphenyl, 4-isopropylphenyl, 4-tert.butylphenyl, 4-ethoxyphenyl, 4-ethynyloxyphenyl, 4-methylmercaptophenyl, 4-methylsulfonylphenyl, 4-cyanophenyl, 4-methoxycarbonyl-phenyl, 3-bromophenyl, 3-chlorophenyl, 2-chlorophenyl, 2,4-dichlorophenyl, 3,4,5-trichlorophenyl, 3,4-difluorophenyl, 3,4-dibromophenyl, 3,4-dimethoxyphenyl, 3,4-dimethylphenyl, 3-chloro-4-cyanophenyl, 4-chloro-3-cyanophenyl, 3-bromo-4-methylphenyl, 4-methoxy-3-methylphenyl, 3-fluoro-4-methoxyphenyl, 4-chloro-3-methylphenyl, 4-chloro-3-trifluoromethyl-phenyl, 4-bromo-3-chlorophenyl, 4-trifluoromethylphenyl, 4-trifluoromethoxyphenyl, 4-methoxyphenyl, etc. Typical examples for substituted heteroaryl include 5-methyl-2-thienyl, 5-chloro-2-thienyl, 3-chloro-2-thienyl, 5-methyl-2-furyl, 4-methyl-oxazol-5-yl, 5-hydroxy-pyrazol-1-yl, 5-hydroxy-3-methyl-pyrazol-1-yl, 5-amino-3-methyl-pyrazol-1-yl, 5-amino-pyrazol-1-yl, 5-methyl-[1,3,4]-oxadiazol-2-yl, 5-ethyl-[1,3,4]-oxadiazol-2-yl, 2-amino-thiazol-4-yl, 2-methyl-thiazol-4-yl, 6-chloro-pyridin-2-yl, 6-amino-pyridin-2-yl, etc.

The N-ring system, being defined for the combination of $R_1$ and $R_2$ includes primarily simple cyclic secondary amines like pyrrolidinyl, piperidinyl, morpholinyl, thiomorpholinyl and the alkyl-substituted derivatives, e.g. methyl-morpholinyl and dimethyl-morpholinyl.

The group —N=$CR_9$—$NR_{10}R_{11}$ includes the various combinations of substituents for $R_9$, $R_{10}$ and $R_{11}$ including simple structures such as —N=CH—N(CH$_3$)$_2$, —N=C(CH$_3$)—N(CH$_3$)$_2$ and —N=C(C$_2$H$_5$)—N(CH$_3$)$_2$.

The group —CO—$R_9$ represents an acyl radical which includes a very wide variation of the basic acid. It encompasses formic acid, the alkanoic acids as defined above and the aromatic acids. Typical examples in addition to the alkanoyl radicals are benzoyl, phenylacetyl, phenylpropionyl, á-methyl-phenylacetyl, nicotinoyl, isonicotinoyl, chlorobenzoyl, trifluoroacetyl, pentafluoropropionyl, heptafluorobutyryl, chloroacetyl, dichloroacetyl, trichloroacetyl, á,á-dimethyl-â-chloropropionyl, cyclopropylcarbonyl, etc. The same definitions apply where —CO—$R_9$ is part of —O—CO—$R_9$ or —NH—CO—$R_9$.

The group —CO—O—$R_{10}$ represents for example methoxycarbonyl, ethoxycarbonyl, etc. The group —CO—$NR_{10}R_{11}$ stands for example for methylaminocarbonyl, ethylaminocarbonyl, propylaminocarbonyl, dimethyl-aminocarbonyl, ethyl-methylaminocarbonyl, diethylaminocarbonyl, etc.

The presence of at least one asymmetric carbon atom in the compounds of formula I means that the compounds may occur in optically isomeric and enantiomeric forms. As a result of the presence of a possible aliphatic C=C double bond, geometric isomerism may also occur. Formula I is intended to include all those possible isomeric forms and mixtures thereof.

Certain compounds of formula I are capable of forming acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, maleic acid, tartaric acid, citric acid, oxalic acid or amino acids, such as argentine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxy-ethane-sulfonic acid, or aromatic sulfonic acids, for example benzene-, p-toluene- or naphthalene-2-sulfonic acid.

Formula I according to the invention shall include all the possible isomeric forms, as well as mixtures, e.g. racemic mixtures, and any mixtures of rotamers.

In view of the close relationship between the compounds of formula I in free form and in the form of their salts, including also salts that can be used as intermediates, for example in the purification of the compounds of formula I or in order to identify those compounds, herein-before and hereinafter any reference to the (free) compounds is to be understood as including also the corresponding salts, where appropriate and expedient.

Among the compounds of formula I according to the present invention the following groups of compounds are preferred. These groups are those wherein $R_1$ is hydrogen, $C_1$–$C_4$alkyl or is a group —CO—$R_9$; or $R_1$ is hydrogen, methyl, trifluoroacetyl, pentafluoropropionyl or heptafluorobutyryl; or $R_1$ is hydrogen or methyl; or $R_1$ is hydrogen, or $R_2$ is hydrogen or $C_1$–$C_4$alkyl; or $R_2$ is hydrogen or methyl; or $R_1$ and $R_2$ are both hydrogen, or $R_1$ and $R_2$ together form the group —N=$CR_9$—$NR_{10}R_{11}$; or $R_1$ and $R_2$ together form the groups —N=CH—N(CH$_3$)$_2$, —N=C(CH$_3$)—N(CH$_3$)$_2$ or —N=C(C$_2$H$_5$)—N(CH$_3$)$_2$; or $R_1$ and $R_2$ together form the groups —N=CH—N(CH$_3$)$_2$ or —N=C(CH$_3$)—N(CH$_3$)$_2$; or $R_3$ is hydrogen; or $R_4$ is hydrogen, hydroxy, amino, $C_1$–$C_4$alkyl, $C_1$–$C_4$haloalkyl, $C_1$–$C_4$cyanoalkyl, $C_1$–$C_6$alkylamino, di($C_1$–$C_4$alkyl)-amino, $C_1$–$C_6$aminoalkyl, halogen, mercapto, cyano, $C_1$–$C_6$alkoxy, $C_2$–$C_6$alkenyloxy, $C_2$–$C_6$alkynyloxy, $C_1$–$C_6$alkylthio, $C_1$–$C_6$alkylsulfinyl, $C_1$–$C_6$alkylsulfonyl, $C_1$–$C_6$hydroxyalkyl, $C_1$–$C_4$alkoxy-$C_1$–$C_6$alkyl, $C_1$–$C_4$alkyl-$C_1$–$C_6$aminoalkyl, $C_1$–$C_4$alkoxycarbonyl, di($C_1$–$C_4$alkyl)-$C_1$–$C_6$aminoalkyl, —CO—$R_9$, or —NH—CO—$R_9$; or $R_4$ is hydrogen, hydroxy, cyano, $C_1$–$C_4$alkyl, $C_1$–$C_4$alkoxy, $C_1$–$C_4$haloalkoxy, $C_1$–$C_4$haloalkyl, $C_1$–$C_4$cyanoalkyl, $C_1$–$C_4$alkanoyloxy, $C_1$–$C_4$hydroxyalkyl, $C_1$–$C_4$haloalkanoyloxy, $C_1$–$C_4$alkanoyl-$C_1$–$C_6$aminoalkyl, $C_1$–$C_4$alkanoyloxy-$C_1$–$C_4$alkyl, $C_1$–$C_4$alkanoyl, $C_1$–$C_4$alkylthio or $C_1$–$C_4$alkoxycarbonyl; or $R_4$ is hydrogen, hydroxy, cyano, fluorine, chlorine, bromine, methyl, tert. butyl, methylthio, trifluoromethyl, cyanomethyl, 2-cyanoethyl, hydroxymethyl, 1-hydroxyethyl, 2-hydroxyisopropyl, acetyl, 2-hydroximino-ethyl, 2-methoximino-ethyl, acetoxymethyl, methoxycarbonyl, methoxy, ethoxy or trifluoromethoxy; or $R_5$ is hydrogen, hydroxy, methoxy or methylthio; or $R_5$ is hydrogen or hydroxy; or $R_5$ is hydrogen; or $R_6$ is hydrogen, or methoxy; or $R_6$ is hydrogen; or $R_7$ is 4-pyridyl or optionally substituted aryl carrying one to three substituents independently selected from the group comprising halogen, $C_1$–$C_4$alkyl, $C_1$–$C_4$alkoxy, $C_1$–$C_4$haloalkyl and $C_1$–$C_4$haloalkoxy; or $R_7$ is phenyl or halophenyl; or $R_7$ is phenyl, 4-fluorophenyl or 4-chlorophenyl; or $R_8$ is hydrogen, $C_1$–$C_4$alkanoyl, $C_1$–$C_4$haloalkanoyl or $C_1$–$C_4$alkyl; or $R_8$ is hydrogen or $C_1$–$C_4$fluoroalkanoyl; or $R_8$ is hydrogen.

Further preferred subgroups of formula I are those compounds wherein:

a) $R_3$, $R_6$ and $R_8$ are all hydrogen, or b) $R_1$ is hydrogen, $C_1$–$C_4$alkyl, or is a group —CO—$R_9$; and $R_2$ is hydrogen or $C_1$–$C_4$alkyl; or $R_1$ and $R_2$ together form the group —N=$CR_9$—$NR_{10}R_{11}$; $R_3$ is hydrogen or methyl; and $R_4$ is hydrogen, hydroxy, amino, $C_1$–$C_4$alkyl, $C_1$–$C_4$haloalkyl, $C_1$–$C_4$cyanoalkyl, $C_1$–$C_6$alkylamino, di($C_1$–$C_4$alkyl)-amino, $C_1$–$C_6$aminoalkyl, halogen, mercapto, cyano, $C_1$–$C_6$alkoxy, $C_2$–$C_6$alkenyloxy, $C_2$–$C_6$alkynyloxy, $C_1$–$C_6$alkylthio, $C_1$–$C_6$alkylsulfinyl, $C_1$–$C_6$alkylsulfonyl, $C_1$–$C_6$hydroxyalkyl, $C_1$–$C_4$alkoxy-$C_1$–$C_6$alkyl, $C_1$–$C_4$alkyl-$C_1$–$C_6$aminoalkyl, di($C_1$–$C_4$alkyl)-$C_1$–$C_6$aminoalkyl, $C_1$–$C_4$alkoxycarbonyl; —CO—$R_9$, or —NH—CO—$R_9$; and $R_5$ is hydrogen, hydroxy, methoxy or methylthio; and $R_6$ is hydrogen or methoxy; and $R_7$ is 4-pyridyl or optionally substituted aryl carrying one to three substituents independently selected from the group comprising halogen, $C_1$–$C_4$alkyl, $C_1$–$C_4$alkoxy, $C_1$–$C_4$haloalkyl and $C_1$–$C_4$haloalkoxy; and $R_8$ is hydrogen, $C_1$–$C_4$alkanoyl, $C_1$–$C_4$haloalkanoyl or $C_1$–$C_4$alkyl; or c) $R_1$ is hydrogen, methyl, trifluoroacetyl, pentafluoropropionyl or heptafluorobutyryl; and $R_2$ is hydrogen or $C_1$–$C_4$alkyl; or $R_1$ and $R_2$ are both hydrogen, or $R_1$ and $R_2$ together form the groups —N=CH—N(CH$_3$)$_2$ or —N=C(CH$_3$)—N(CH$_3$)$_2$; and $R_3$ is hydrogen or methyl; and $R_4$ is hydrogen, hydroxy, $C_1$–$C_4$alkyl, $C_1$–$C_4$alkoxy, $C_1$–$C_4$haloalkoxy, $C_1$–$C_4$haloalkyl, $C_1$–$C_4$cyanoalkyl, $C_1$–$C_4$alkanoyloxy, $C_1$–$C_4$hydroxyalkyl, $C_1$–$C_4$haloalkanoyloxy, $C_1$–$C_4$alkanoyl-$C_1$–$C_6$aminoalkyl, $C_1$–$C_4$alkanoyloxy-$C_1$–$C_4$alkyl, $C_1$–$C_4$alkanoyl, $C_1$–$C_4$alkylthio or $C_1$–$C_4$alkoxycarbonyl; and $R_5$ is hydrogen or hydroxy; and $R_6$ is hydrogen; and $R_7$ is phenyl or halophenyl; and $R_8$ is hydrogen or $C_1$–$C_4$fluoroalkanoyl; or d) $R_1$ is acetyl; and $R_2$ is hydrogen or methyl; or $R_1$ and $R_2$ together form the groups —N=CH—N(CH$_3$)$_2$ or —N=C(CH$_3$)—N(CH$_3$)$_2$; and $R_3$ is hydrogen; and $R_4$ is hydrogen, hydroxy, cyano, fluorine, chlorine, bromine, methyl, tert. butyl, methylthio, trifluoromethyl, hydroxymethyl, cyanomthyl, 2-cyanoethyl, 1-hydroxyethyl, 2-hydroxyisopropyl, acetyl, 2-hydroximino-ethyl, 2-methoximino-ethyl, acetoxymethyl, methoxycarbonyl, methoxy, ethoxy or trifluoromethoxy; and $R_5$ and $R_6$ are hydrogen; and $R_7$ is phenyl, 4-fluorophenyl or 4-chlorophenyl; and $R_8$ is hydrogen or $C_1$–$C_4$fluoroalkanoyl; or e) $R_1$, $R_2$, $R_3$, $R_5$, $R_6$ and $R_8$ are all hydrogen, and $R_4$ is hydrogen, hydroxy, cyano, fluorine, chlorine, bromine, methyl, tert. butyl, methylthio, trifluoromethyl, cyanomethyl, 2-cyanoethyl, hydroxymethyl, 1-hydroxyethyl, 2-hydroxyisopropyl, acetyl, 2-hydroximino-ethyl, 2-methoximino-ethyl, acetoxymethyl, and $R_7$ is phenyl, 4-fluorophenyl or 4-chlorophenyl.

Other preferred subgroups are characterized by subformula IA

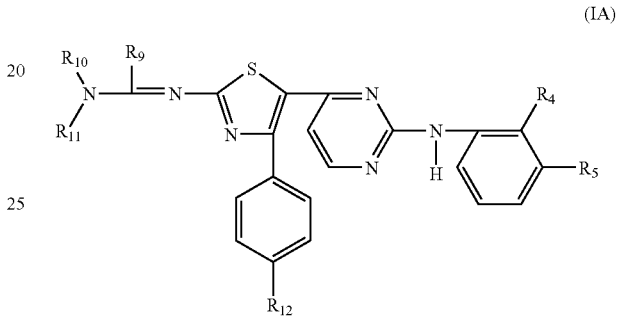

(IA)

wherein $R_4$ is hydrogen, cyano, hydroxy, $C_1$–$C_4$alkoxy, $C_1$–$C_6$aminoalkyl, $C_1$–$C_8$alkanoyloxy-$C_1$–$C_4$alkyl, $C_1$–$C_8$alkanoylamino-$C_1$–$C_4$alkyl, $C_1$–$C_4$alkoxy-$C_1$–$C_6$alkyl, $C_1$–$C_6$hydroxyalkyl or $C_1$–$C_4$cyanoalkyl; $R_5$ is hydrogen, hydroxy, halogen, $C_1$–$C_6$alkyl, $C_1$–$C_6$alkoxy or $C_1$–$C_6$haloalkyl; $R_9$ is hydrogen, $C_1$–$C_6$alkyl, $C_1$–$C_6$haloalkyl, $C_3$–$C_7$cycloalkyl, $C_3$–$C_7$cycloalkyl-$C_1$–$C_4$alkyl, $C_1$–$C_4$alkyl-$C_3$–$C_7$cycloalkyl-$C_1$–$C_4$alkyl, aryl, aryl-$C_1$–$C_4$alkyl, heteroaryl or heteroaryl-$C_1$–$C_4$alkyl; $R_{10}$ is $C_1$–$C_6$alkyl, $C_1$–$C_6$haloalkyl, $C_3$–$C_7$cycloalkyl-$C_1$–$C_4$alkyl or $C_1$–$C_4$alkoxy-$C_1$–$C_6$alkyl; $R_{11}$ is $C_1$–$C_6$alkyl, $C_3$–$C_7$cycloalkyl, $C_3$–$C_7$cycloalkyl-$C_1$–$C_4$alkyl, $C_1$–$C_4$alkoxy-$C_1$–$C_6$alkyl, aryl or heteroaryl; and $R_{12}$ is halogen, $C_1$–$C_4$alkyl, $C_1$–$C_4$alkoxy, $C_1$–$C_4$haloalkyl or $C_1$–$C_4$haloalkoxy; or $C_1$–$C_4$haloalkyl and $C_1$–$C_4$haloalkoxy, and $R_{13}$ is $C_1$–$C_4$alkyl; or by subformula IB

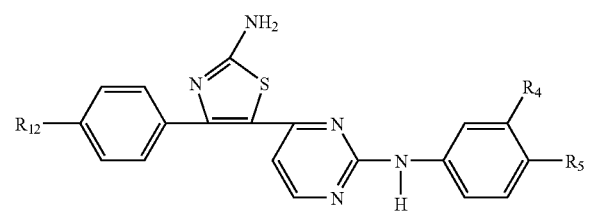

(IB)

wherein $R_4$ is hydrogen, hydroxy, cyano, $C_1$–$C_4$alkoxy, $C_1$–$C_6$aminoalkyl, $C_1$–$C_8$alkanoyloxy-$C_1$–$C_4$alkyl, $C_1$–$C_8$alkanoylamino-$C_1$–$C_4$alkyl, $C_1$–$C_4$alkoxy-$C_1$–$C_6$alkyl, $C_1$–$C_6$hydroxyalkyl or $C_1$–$C_4$cyanoalkyl, and $R_{12}$ is halogen, $C_1$–$C_4$alkyl, $C_1$–$C_4$alkoxy, $C_1$–$C_4$haloalkyl and $C_1$–$C_4$haloalkoxy.

Preferred individual compounds of the formula I

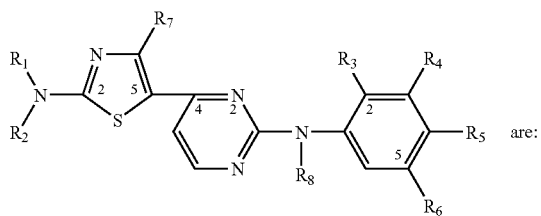

are:

N-[4-(2-amino-4-phenyl-thiazol-5-yl)-pyrimidin-2-yl]-N-phenyl-amine,
N-{4-[2-amino-4-(4-fluoro-phenyl)-thiazol-5-yl]-pyrimidin-2-yl}-N-phenyl-amine;
N-[4-(2-amino-4-phenyl-thiazol-5-yl)-pyrimidin-2-yl]-N-[3-(1-hydroxyethyl)-phenyl]-amine;
N-{4-[2-amino-4-(4-fluoro-phenyl)-thiazol-5-yl]-pyrimidin-2-yl}-N-[3 -(1-hydroxyethyl)-phenyl]-amine;
N-[4-(2-amino-4-phenyl-thiazol-5-yl)-pyrimidin-2-yl]-N-[3-(1-hydroxy-1-methylethyl)-phenyl]-amine;
N-{4-[2-amino-4-(4-fluoro-phenyl)-thiazol-5-yl]-pyrimidin-2-yl}-N-[3-(1-hydroxy-1-methylethyl)-phenyl]-amine;
N-[4-(2-amino-4-phenyl, thiazol-5-yl)-pyrimidin-2-yl]-N-(3-acetyl-phenyl)-amine;
N-{4-[2-amino-4-(4-fluoro-phenyl)-thiazol-5-yl]-pyrimidin-2-yl}-N-(3-acetyl-phenyl)-amine;
N-[4-(2-amino-4-thiazol-5-yl)-pyrimidin-2-yl]-N-(3-cyano-phenyl)-amine;
N-{4-[2-amino-4-(4-fluoro-phenyl)-thiazol-5-yl]-pyrimidin-2-yl}-(3-cyano-phenyl)-amine;
{4-[2-acetylamino-4-(4-fluoro-phenyl)-thiazol-5-yl]-pyrimidin-2-yl}-N-(3-acetoxymethyl-phenyl)-amine;
N-[4-(2-amino-4-phenyl-thiazol-5-yl)-pyrimidin-2-yl]-N-(3-methoxy-phenyl)-amine;
N-{4-[2-amino-4-(4-fluoro-phenyl)-thiazol-5-yl]-pyrimidin-2-yl}-N-(3-methoxy-phenyl)-amine;
N-[4-(2-amino-4-phenyl-thiazol-5-yl)-pyrimidin-2-yl]-N-(3-cyano-phenyl)-amine;
N-[4-(2-amino-4-phenyl-thiazol-5-yl)-pyrimidin-2-yl]-N-(4-fluoro-phenyl)-amine;
N-{4-[2-amino-4-(4-fluoro-phenyl)-thiazol-5-yl]-pyrimidin-2-yl}-N-(3-cyano-phenyl)-amine;
N-[4-(2-amino-4-phenyl-thiazol-5-yl)-pyrimidin-2-yl]-N-(3-cyanomethyl-phenyl)-amine; and
N-{4-[2-amino-4-(4-fluoro-phenyl)-thiazol-5-yl]-pyrimidin-2-yl}-N-(3-cyanomethyl-phenyl)-amine.

The compounds according to the invention may be prepared according to methods per se known in the art (this means that in spite of employing generally known types of organic reaction steps, that where novel compounds are produced, the respective process of manufacture and the sequence of steps is novel because it has not been known for be employable for the novel compound). The procedures for the preparation of compounds of formula I may be outlined as follows:

Scheme I: Employing the Hantzsch-synthesis for forming the thiazole ring:

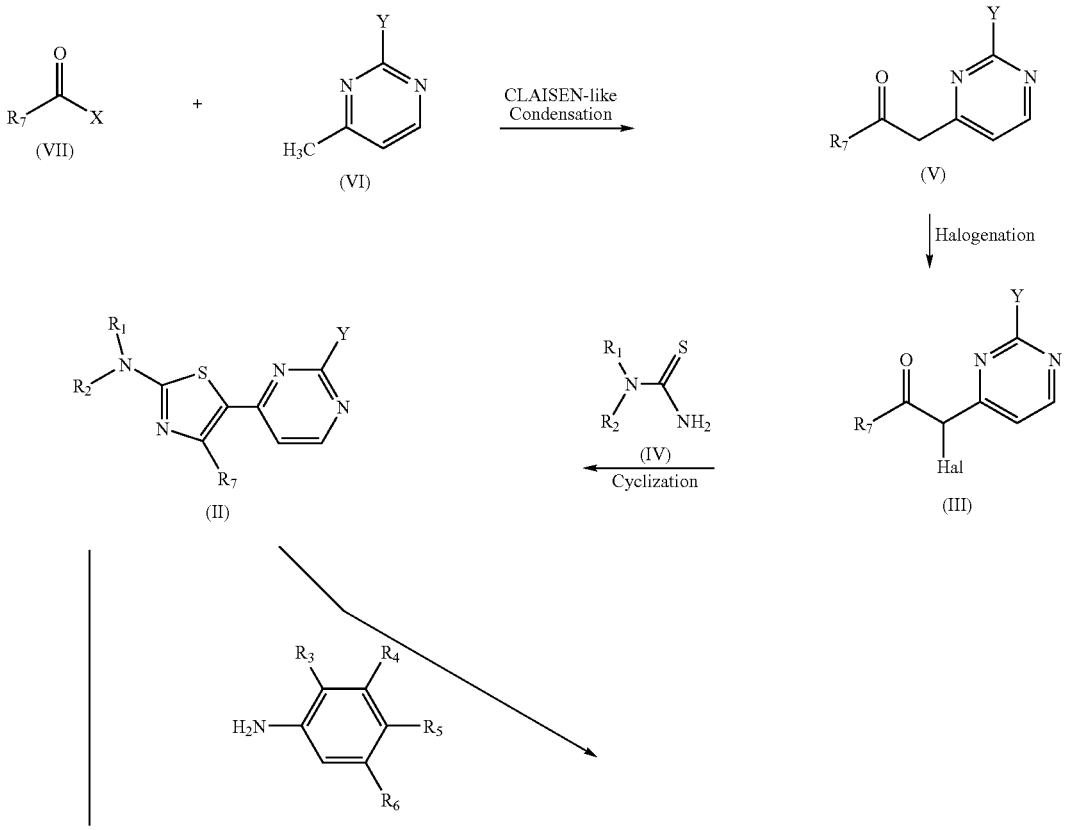

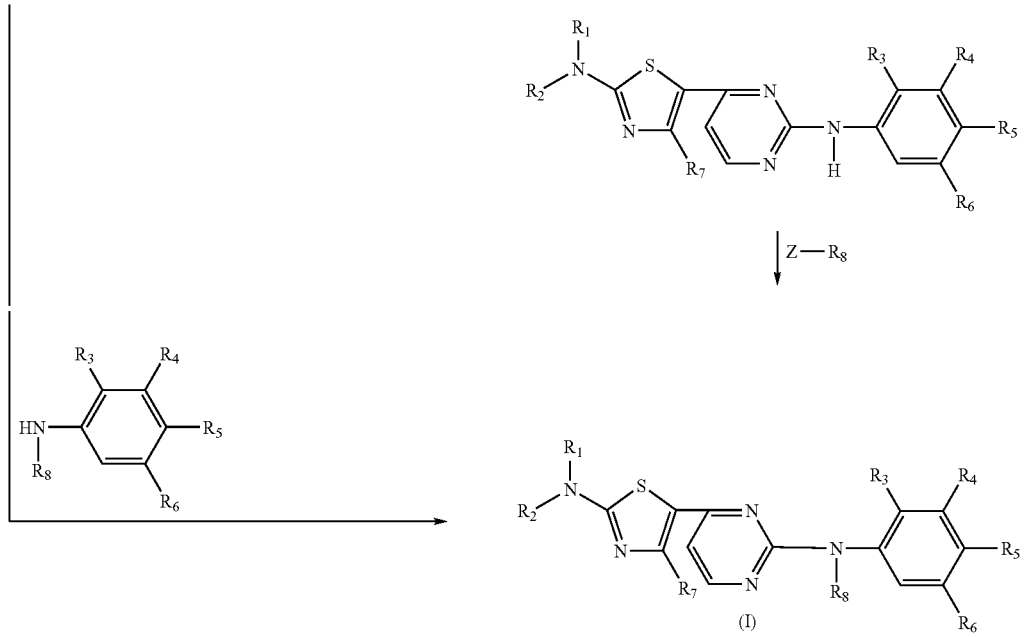

As shown in Scheme 1 the compounds of formula I may be obtained by reaction of compounds of formula II wherein $R_1$ and $R_2$ are as defined for formula I, Y stands for a leaving group such as halogen, alkylthio, alkylsulfinyl, alkylsulfonyl and Z is a leaving group such as halogen, $C_1$–$C_4$alkylthio, $C_1$–$C_4$alkylsulfinyl or $C_1$–$C_4$alkylsulfonyl, with an aniline of the displayed formula wherein $R_3$, $R_4$, $R_5$, $R_6$ and $R_8$ are as defined for formula I. In this reaction the leaving group Y is substituted with the aniline of the shown formula.

The anilines with substituents $R_3$, $R_4$, $R_5$, $R_6$ and $R_8$ are mostly commercially available or otherwise can easily be obtained from commercial products by per se known processes. The thiazolyl pyrimidines of formula II have especially been developed for the synthesis of the compounds of formula I and thus comprise another feature of the present invention.

The nucleophilic substitution of a group Y is typically conducted in the presence of a Lewis acid using an excess of aniline. Y stands for a leaving group, such as halogen, alkylthio, alkylsulfinyl or alkylsulfonyl. The reaction may be carried out in an inert solvent, such as ethers like tetrahydrofuran, dioxane, diglyme and the like. Appropriate reaction conditions are described for analogous reactions e.g. in U.S. Pat. Nos. 5,670,527 or 5,658,903.

Typical Lewis acids include boron trifluoride, zinc halogenides and sulfonic acids like benzenesulfonic, toluenesulfonic, methanesulfonic and ethanesulfonic acids. The reaction temperature may vary within wide ranges, e.g. from +20° C. to +220° C., but mostly is performed at the boiling point of the reaction mixture.

The leaving groups are the standard ones commonly used in organic synthesis. The relative reactivity of the leaving group X can for examples be modulated by oxidation of the alkylthio group to the corresponding more reactive sulfoxide or sulfone using standard conditions.

The compounds of formula II are novel and may be prepared by reacting a compound of the formula III with a thiourea IV. This reaction is in the literature referred to as Hantzsch thiazole synthesis and may be performed under reaction conditions described in the literature for this type of ring formation. The thioureas of formula IV are commercial products, or may be synthesized according to known processes.

The intermediate α-halogen-β-pyrimidinylacetyl derivatives of formula III are likewise novel and have been developed for the synthesis of the final active ingredients of this invention. The intermediates of formula III may be prepared by reacting an analogous β-pyrimidinylacetyl derivative of formula V with a halogenating agent. $R_7$ is as defined for formula I and Hal stands for a halogen atom, preferably bromine or chlorine. Typical halogenating agents include bromine and chlorine and its addition compounds with amines as well as copper bromide and the like. The reaction is preferably conducted in an organic solvent, such as acetic acid, alcohols or halogenated hydrocarbons, such as chloroform or methylene chloride. The reaction temperature may vary from –20° C. to boiling temperature of the reaction mixture, depending on the reactivity of the halogenated compound of formula V. It is typically close to room temperature.

Compounds of the general formula V wherein $R_7$ is as defined for formula I may be prepared by reacting a methylpyrimidine of the formula VI with a carbonic acid derivative of formula VII. The radical X in formula VII stands for a leaving group such as alkoxide, dialkylamine, dialkyl hydroxylamine, halogen and acyloxy. Many of the α-pyrimidinylacetyl derivatives of formula V are known, and the still novel ones can be obtained according to known methods. The starting materials VI and VII are known compounds.

The first reaction step of Scheme 1 is a type of Claisen type ester condensation. The condensation is achieved in the presence of strong bases, including alkoxides, such as potassium t-butoxide or sodium t-butoxide, lithiumamides, such as LDA or LiHMDS and metal hydrides, such as potassium or sodium hydride, and is preferably conducted in an inert solvent. Typical solvents are ethers, such as diethylether, glyme and THF. In certain cases the use of more polar solvents, such as DMF, DMSO and HMPT is preferred. The reaction is typically performed at temperatures ranging from −78° C. to the boiling point of the solvent.

For reasons of laboratory convenience and rationalization of work, a reasonable approach is to start the synthesis of compounds of formula I with thiourea (intermediate IV wherein $R_1$ and $R_2$ are hydrogen) and to modify the amino group $NR_1R_2$ on the stage of the intermediate of formula II by conducting a Sandmeyer replacement reaction according to Subscheme 1a followed by displacement of halogen by an amine $HNR_1R_2$.

Subscheme 1a: Modification of the amino function in intermediate of formula II:

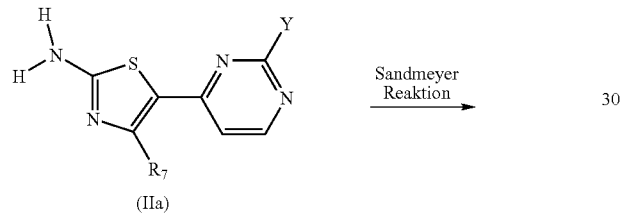

(IIa)

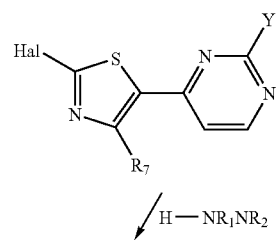

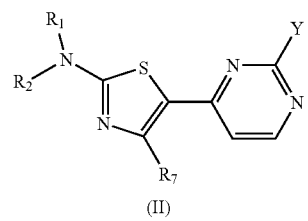

(II)

In Subscheme 1a the radicals are defined as in Scheme 1.

Alternatively, the compounds of formula I may be obtained according to Schemes 2 and 3.

Scheme 2: Route via an acetylthiazole:

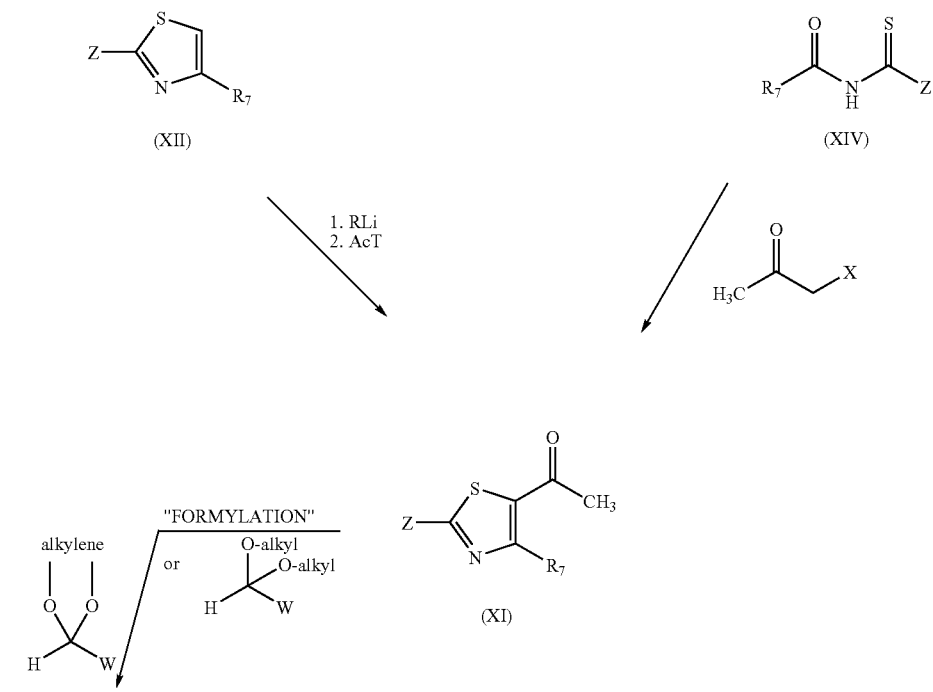

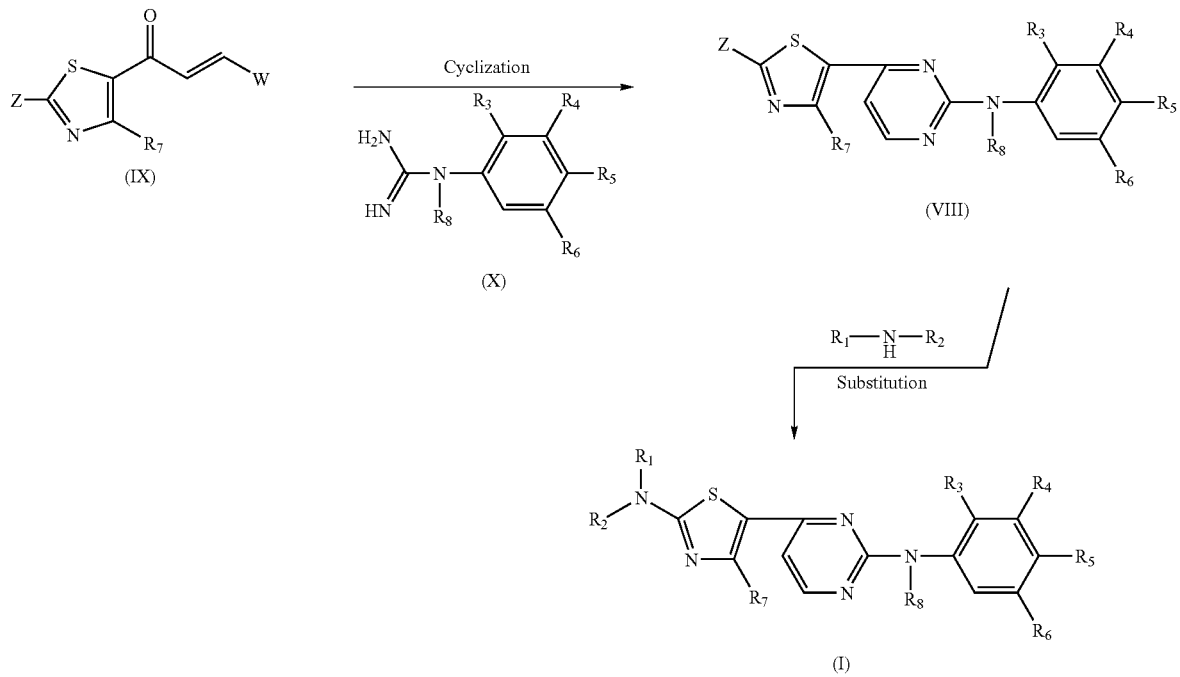

According to Scheme 2 the compounds of formula I may be obtained by reaction of compounds of formula VIII wherein $R_3$, $R_4$, $R_5$, $R_6$, $R_7$ and $R_8$ are as defined for formula I and Z is a leaving group such as halogen, $C_1$–$C_4$alkylthio, $C_1$–$C_4$alkylsulfinyl or $C_1$–$C_4$alkylsulfonyl with an amine $HNR_1R_2$. The intermediates of formula VIII represent another feature of the present invention.

This amination reaction with a secondary amine $HNR_1R_2$ is a typical nucleophilic substitution reaction and may be carried out under the conditions known as common for such reactions. The reaction may be carried out in an inert solvent, such as ethers, dimethylformamide, dimethylsulfoxide, alcohols, acetonitrile, and the like.

For the case that nucleophilic amines are used, this reaction will work without the presence of an additional base; however, when more acidic amines are employed a base may be required. Typical bases include alkaline carbonates, such as potassium carbonate and sodium carbonate or metal alcoholates, such as potassium tert-butoxide. The reaction temperature may vary within wide ranges, e.g. from room temperature to +150° C. In the case of Z being alkylthio the reactivity of the intermediate starting material VIII may be enhanced by oxidizing the leaving group W to the corresponding sulfoxide or sulfone using standard conditions for such transformations.

The intermediates of formula VIII may in turn be obtained by reacting a compound of formula IX wherein $R_7$ is defined as for formula I, W stands for a secondary amino group, wherein the two radicals are either $C_1$–$C_4$alkyl or together form an alkylene chain, with dimethylamino being the preferred embodiment, and Z is as defined for formula VIII, and with a guanidine of formula X wherein the substituents $R_3$, $R_4$, $R_5$, $R_6$ and $R_8$ are as defined for formula I.

The guanidines of formula X are known in the art, and are even commercially available. In contrast, the intermediates of formula IX are novel and yet stand for another feature of the present invention, and so is the preceding intermediate of formula XI which had to be especially created in order to enable this synthesis pathway of the active ingredients of formula I.

This cyclization reaction step (IX+X ? VIII) may be carried out in the presence or absence of a solvent. The presence of a solvent is preferred in laboratory scale, while technical scale production prefers the variants without use of solvents. Typical solvents for this step would include alcohols, such as ethanol, iso-propanol, iso-butanol and the like, dimethylformamide, ethers, such as dioxane and hydrocarbons, such as toluene. In case where the guanidine VIII is used in form of an addition salt other then a hydrogen carbonate the addition of an additional base as co-reagent is required. The reaction temperature may vary within narrow ranges, but is principally defined by the boiling temperature of the reaction mixture. Typically, such temperatures are between +80° C. and +150° C.

The compounds of the general formula IX as defined above may be obtained by reacting an acetyl thiazole compound of formula XI with a dialkyl-formamide acetal, such as dimethylformamide dimethyl acetal or dimethylacetamide acetal. Alkyl in Scheme 2 represents $C_1$–$C_4$alkyl, e.g. methyl while alkylene is a straight or branched $C_1$–$C_5$hydrocarbon bridge like methylene, ethylene, methylethylene, ethylethylene or dimethylethylene. Where desired a solvent may be used. Typical solvents include dimethylformamide and dioxane. The reaction temperature lies typically between +80° C. and +120° C.

Compounds of the general formula XI may be obtained by metallating a thiazole of the formula XII with a metallating agent such as alkyllithium and reacting it with an acetylating agent AcT wherein T is a leaving group being typically the N,O-dimethylhydroxylamino radical (Weinrebs amide), or otherwise preferably N,N-dimethylamino. Metallation is performed in a inert solvent, such as ethers like diethyl ether, tetrahydrofuran or alkanes and mixtures thereof. The metallating agent is typically butyllithium. The reaction temperature lies in the range of −78° C. to 0° C. The metallated transitional intermediate formed from the thiazole is in this reaction quenched with an acyl equivalent AcT. The thiazole compounds of formula XII is described in literature.

Alternatively compounds of formula XI, where Z stands for $C_1$–$C_4$alkylthio or optionally substituted amino can be prepared by reacting a compound of formula XIV with halogenated acetone, e.g. bromoacetone. The compounds of formula XIV are known in the art.

lithiated species is in-situ transmetallated using at least stoichiometric amounts of a zinc salt, such as zinc chloride or zinc bromide. The thus obtained zinc compound may then be reacted with 2,4-diiodopyrimidine in the presence of a palladium catalyst. Typical palladium catalysts include $Pd(PPh_3)_4$ or $Pd_2dba_3$. The reaction temperature of the coupling lies in the range of 0° C. to the boiling point of the reaction mixture.

Scheme 3: Route employing a Negishi-type coupling reaction:

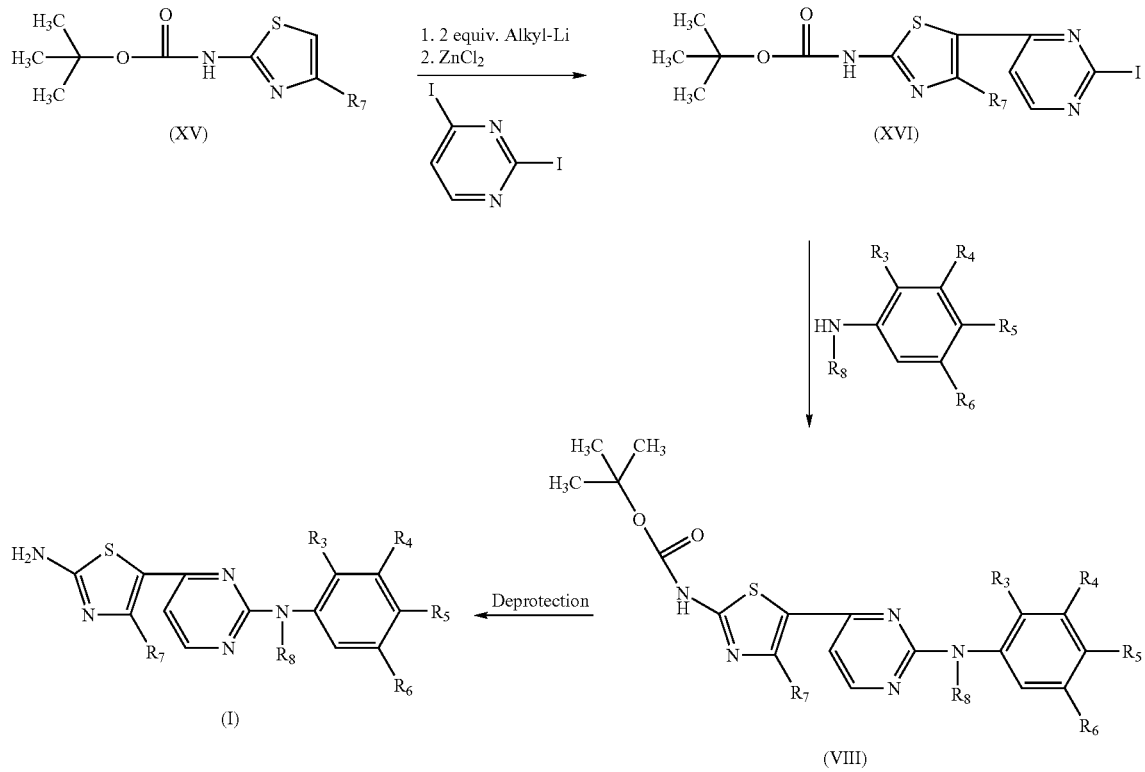

The Negishi type coupling reaction allows to build up the basic structure of the active ingredients of formula I in a different manner. This may have advantages for some specific substitution patterns in formula I.

In Scheme 3 the radicals are as defined above. The reaction conditions may in general correspond to the following:

Deprotection of compounds of the general formula VIII to form compounds of the formula I may be accomplished by treating a compound of the general formula VIII with an acid using standard conditions.

Compounds of the general formula VIII may be obtained in accordance to Scheme 1 by displacement of iodine by an aniline under reaction conditions already described above.

Compounds of the general formula XVI may be obtained by reacting an aminothiazole XV according to the method of Negishi. Thus a compound of formula XV is allowed to react with a metallating agent, such as n-hexyllithium or n-butyl-lithium, in an inert solvent, such as ethers like tetrahydro-furan, glyme, diethyl ether and the like, to give a dilithiated intermediate. The reaction temperature may vary within ranges. It typically lies between −78° C. to 0° C. The For various reasons it may also be desirable to transform one derivative of formula I into another one which is also within the general definition of formula I.

Thus, it is for example possible to acylate compounds of the subformula Ia wherein $R_1$ is hydrogen using acylating agents.

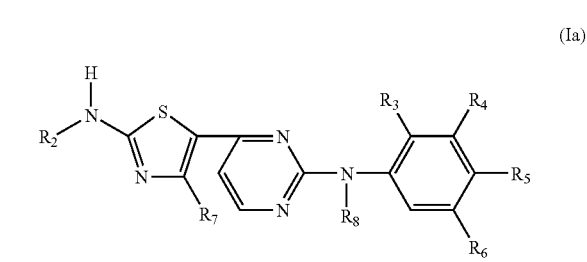

Typical acylation agents for this purpose include carboxylic acid chlorides, carboxylic acid anhydrides, chloroalkyl formiates, carbamoylchlorides and the like. The acylation may be carried out in the presence or absence of a base. The reaction temperature will suitably lie in the range from 0° C. to the boiling point of the reaction mixture. Inert solvents may be used where desired or indicated by the nature of the reagents. Examples of suitable bases include alkaline metal carbonates or bicarbonates, such as potassium carbonate or sodium hydrogen carbonate (referred to as Schotten-Baumann conditions) or tertiary amines, such as triethylamine or diisopropylethylamine. Examples of suitable solvents include aromatic hydrocarbons such as toluene; ethers such as diethyl ether, tetrahydrofuran and glyme or mixtures with water.

If in the compound of formula Ia $R_2$ is hydrogen, and depending on the nucleophilicity of the acylating agent and the reaction conditions not only mono- but also diacylated products can be obtained. Therein $R_1$ and $R_2$ independently of each other stand for identical or different —CO—$R_9$ moieties. Where the diacylated product appears as a by-product to the monoacylated compound of formula Ia, the product mixtures can be separated by crystallization or chromatography.

Derivatives of the subformula Ib

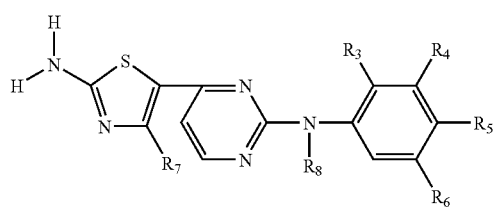

(Ib)

may be modified if desired
a) by reacting them with an amide acetal. Typical amide acetals include dimethylformamide acetal and dimethylacetamide acetal. The reaction is typically carried out with the pure reagents, i.e. without the presence of a solvent. Where desired, also inert solvents such as dimethylformamide or ethers, such as tetrahydrofuran, glyme or dioxane, or esters may be used. The reaction temperature lies in the range from about +50° C. to the boiling point of the mixture. or
b) by alkylating them in a reaction where the compound of formula Ib is treated with an aldehyde in the presence of a reducing agent (in the literature referred to as reductive alkylation). This reaction is with advantage performed in a solvent. Typical solvents include ethers, such as tetrahydrofuran, glyme, acetic acid or alcohols. Reducing agents include borohydrides, such as sodium borohydride and sodium cyanoborohydride. The reaction temperature lies in the range from 0° C. to the boiling point of the solvent.

Further derivatives of the formula I may be easily obtained from reacting the compounds of subformula Ic

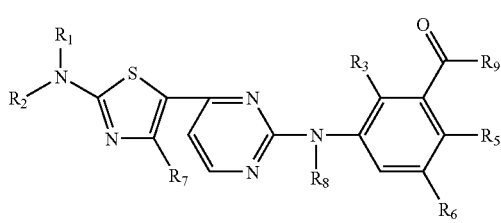

(Ic)

at the functional carbonylic group in $R_4$, e.g. with Grignard-reagents and other metallated radicals to yield the corresponding tertiary alcohols. The reaction of this type is routinely performed in inert solvents and with using an excess of metallated agent. Typical solvents are ethers such as diethyl ether, tetrahydrofuran, glyme and the like. The reaction temperature lies in the range of 0° C. to the boiling point of the solvent, but is normally kept under strict control by cooling and slow addition of the reactant of formula Ic. The standard work-up processes allow to isolate the compounds of formula I, wherein $R_4$ is hydroxyalkyl in high yields and as pure compounds.

When employing the functional intermediate of formula Id

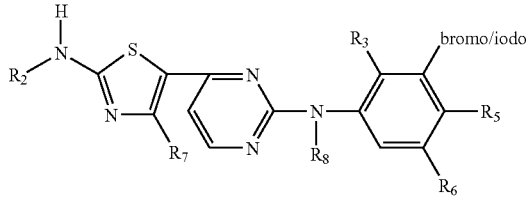

(Id)

additional transition metal catalyzed reactions, such as Sonogashira, Heck, Stille and Suzuki couplings, as well as Hartwig-Buchwald aminations offer further opportunities for derivatization of already prepared compounds of formula I. The indicated methods are known in the art and may be suitably adapted to the requirements of the envisaged derivatization.

In addition to the novel active fungicidal compounds the present invention also relates to novel starting materials and/or intermediates and to processes for the preparation thereof. The starting materials used and the reaction conditions chosen are preferably such that the compounds shown in this disclosure as being especially preferred or to be used preferably are obtained. Especially preferred among the process conditions are those described in the examples below, or analogous procedures.

The invention also relates to compositions which comprise the compounds of the formula I, or a salt thereof, as an active component, in particular plant-protecting compositions, and also to their use in the agricultural sector or related areas.

Active compounds of the formula I are customarily used in the form of compositions and may be added, simultaneously or successively, to the surface or plant to be treated together with additional active compounds. These additional active compounds may be either fertilizers, trace element-supplying agents or other preparations which influence plant growth. It is also possible, in this context, to use selective herbicides, such as insecticides, fungicides, bactericides, nematicides or molluscicides, or mixtures of several of these preparations, additionally, where appropriate, together with excipients, surfactants or other administration-promoting additives which are customary in formulation technology (designated collectively as carrier materials herein).

Suitable excipients and additives may be solid or liquid and are those substances which are appropriate in formulation technology, for example natural or regenerated minerals, solvents, dispersants, wetting agents, adhesives, thickening agents, binding agents or fertilizers.

A preferred method for applying a compound of formula I, or an agrochemical composition which comprises at least one of these compounds, is administration to the leaves (foliar application). The frequency and rate of administration depend upon the risk of infestation by the corresponding pathogen. The compounds of formula I can, however, also penetrate the plant through the roots via the soil (systemic action). If the locus of the plant is impregnated with a liquid formulation or if the substances are introduced in solid form into the soil, e.g. in the form of granules (soil application). In paddy rice crops, such granules can be applied in metered amounts to the flooded rice fields. In order to treat seeds, the compounds of formula I can, however, also be applied to the seeds (coating), either by impregnating the grains or tubers with a liquid formulation of the active ingredient, or by coating them with a solid formulation.

Advantageous rates of application are in normally from 5 g to 2 kg of active ingredient (a.i.) per hectare (ha), preferably from 10 g to 1 kg of a.i./ha, especially from 20 g to 600 g a.i./ha. When the compound are used as seed dressings, dosages of from 10 mg to 1 g of active ingredient per kg seed are advantageous employed. The agrochemical compositions generally comprise 0.1 to 99% by weight, preferably 0.1 to 95% by weight, of a compound of formula I, 99.9 to 1% by weight, preferably 99.8 to 5% by weight, of a solid or liquid adjuvant and 0 to 25% by weight, preferably 0.1 to 25% by weight, of a surfactant. Whereas commercial products will preferably be formulated as concentrates, the end user will normally employ dilute formulations.

The compositions may also comprise further auxiliaries, such as fertilizers and other active ingredients for obtaining special desirable biological effects.

The compounds of formula I may be used preventatively and/or curatively in the sector of agronomics and related technical areas as active ingredients for controlling plant pests. The active ingredients of formula I according to the invention are notable for their good activity even at low concentrations, for their good plant tolerance and for their environmentally friendly nature. They have very advantageous, especially systemic, properties and may be used to protect a plurality of cultivated plants. Using the active ingredients of formula I on plants or plant parts (fruit, flowers, leaves, stems, tubers, roots) of various crops, the pests appearing can be controlled or destroyed, whereby the parts of plants which grow later also remain protected, e.g. from phytopathogenic microorganisms.

The compounds I may additionally be used as a dressing to treat seeds (fruits, tubers, corns) and plant cuttings to protect against fungal infections and against phytopathogenic fungi occurring in the soil.

The compounds I are effective for example against the following classes of related phytopathogenic fungi: Fungi imperfecti (e.g. *Botrytis, Pyricularia, Helminthosporium, Fusarium, Septoria, Cercospora* and *Alternaria*); Basidiomycetes (e.g. *Rhizoctonia, Hemileia, Puccinia*); Ascomycetes (e.g. *Venturia* and *Erysiphe, Podosphaera, Monilinia, Uncinula*) and Oomycetes (e.g. *Phylophthora, Pythium, Plasmopara*).

Target crops for the plant-protecting usage in terms of the invention are for example the following plant cultivars: cereals (wheat, barley, rye, oats, rice, maize, sorghum and related species); beet (sugar beet and fodder beet); pome, stone and berry fruit (apples, pears, plums, peaches, almonds, cherries, strawberries, raspberries and blackberries); legumes (beans, lentils, peas, soya); oil crops (rape, mustard, poppy, olives, sunflowers, coconut, castor oil, cocoa, peanut); cucumber plants (squashes, cucumber, melons); citrus fruits (oranges, lemons, grapefruits, mandarines); vegetables (spinach, lettuce, asparagus, cabbage varieties, carrots, onions, tomatoes, potatoes, paprika); laurels (avocado, cinnamonium, camphor) and plants such as tobacco, nuts, coffee, aubergines, sugar cane, tea, pepper, vines, hops, bananas and natural rubber plants, as well as ornamental plants.

Further areas of application for the active ingredients according to the invention are the protection of stores and material, where the storage matter is protected against putrescence and mould.

The compounds I are used in unchanged form or preferably together with customary excipients in formulation techniques. To this end, they are conveniently processed in known manner e.g. into emulsion concentrates, coatable pastes, directly sprayable or diluable solutions, diluted emulsions, wettable powders, soluble powders, dusts or granules, e.g. by encapsulation into for example polymeric materials. As with the type of medium, the application processes, such as spraying, atomizing, dusting, scattering, coating or pouring are similarly chosen according to the desired aims and the prevailing conditions.

Suitable substrates and additives may be solid or liquid and are useful substances in formulation techniques, e.g. natural or regenerated mineral substances, dissolving aids, dispersants, wetting agents, tackifiers, thickeners or binding agents.

The compounds of formula I may be mixed with further active ingredients, e.g. fertilizers, ingredients providing trace elements or other active ingredients used in the plant protection science, especially further fungicides. In doing so, in some cases synergistic enhancement of the biological effects may occur.

Preferred active ingredients advantageous as additives to the compositions comprising the active ingredient of formula I are:

Azoles, such as azaconazole, BAY 14120, bitertanol, bromuconazole, cyproconazole, difenoconazole, diniconazole, epoxiconazole, fenbuconazole, fluquinconazole, flusilazole, flutriafol, hexaconazole, imazalil, imibenconazole, ipconazole, metconazole, myclobutanil, pefurazoate, penconazole, pyrifenox, prochloraz, propiconazole, simeconazole, tebuconazole, tetraconazole, triadimefon, triadimenol, triflumizole, triticonazole; pyrimidinyl carbinoles, such as ancymidol, fenarimol, nuarimol; 2-amino-pyrimidines, such as bupirimate, dimethirimol, ethirimol; morpholines, such as dodemorph, fenpropidine, fenpropimorph, spiroxamine, tridemorph; anilinopyrimidines, such as cyprodinil, mepanipyrim, pyrimethanil; pyrroles, such as fenpiclonil, fludioxonil; phenylamides, such as benalaxyl, furalaxyl, metalaxyl, R-metalaxyl, ofurace, oxadixyl; benzimidazoles, such as benomyl, carbendazim, debacarb, fuberidazole, thiabendazole; dicarboximides, such as chlozolinate, dichlozoline, iprodione, myclozoline, procymidone, vinclozoline; carboxamides, such as carboxin, fenfuram, flutolanil, mepronil, oxycarboxin, thifluzamide; guanidines, such as guazatine, dodine, iminoctadine; strobilurines, such as azoxystrobin, kresoxim-methyl, metominostrobin, SSF-129, trifloxystrobin, picoxystrobin, BAS 500F (proposed name pyraclostrobin), BAS 520; dithiocarbamates, such as ferbam, mancozeb, maneb, metiram, propineb, thiram, zineb, ziram; N-halomethylthiotetrahydrophthalimides, such as captafol, captan, dichlofluanid, fluoromides, folpet, tolyfluanid; Cu-compounds, such as Bordeaux mixture, copper hydroxide, copper oxychloride, copper sulfate, cuprous oxide, mancopper, oxine-copper; nitrophenol-derivatives, such as dinocap, nitrothal-isopropyl; organo-p-derivatives, such as edifenphos, iprobenphos, isoprothiolane, phosdiphen, pyrazophos, tolclofos-methyl; various others, such as acibenzolar-S-methyl, anilazine, benthiavalicarb, blasticidin-S, chinomethionate, chloroneb, chlorothalonil, cyflufenamid, cymoxanil, dichlone, diclomezine, dicloran, diethofencarb, dimethomorph, SYP-LI90 (proposed name: flumorph), dithianon, ethaboxam, etridiazole, famoxadone, fenamidone, fenoxanil, fentin, ferimzone, fluazinam, flusulfamide, fenhexamid, fosetyl-aluminium, hymexazol, iprovalicarb, IKF-916 (cyazofamid), kasugamycin, methasulfocarb, metrafenone, nicobifen, pencycuron, phthalide, polyoxins, probenazole, propamocarb, pyroquilon, quinoxyfen, quintozene, sulfur, triazoxide, tricyclazole, triforine, validamycin, zoxamide (RH7281).

One preferred method of application of an active ingredient of formula I or of an agrochemical composition containing at least one of these active ingredients is foliar application. The frequency and amount of application depend on the severity of the attack by the pathogen in question. However, the active ingredients I may also reach the plants through the root system via the soil (systemic action) by drenching the locus of the plant with a liquid preparation or by incorporating the substances into the soil in solid form, e.g. in the form of granules (soil application). In rice cultivations, these granules may be dispensed over the flooded paddy field. The compounds I may however also be applied to seed grain to treat seed material (coating), whereby the grains or tubers are either drenched in a liquid preparation of the active ingredient or coated with a solid preparation.

The compositions are produced in known manner, e.g. by intimately mixing and/or grinding the active ingredient with extenders such as solvents, solid carriers and optionally surfactants.

Favorable application rates are in general 1 g to 2 kg of active substance (AS) per hectare (ha), preferably 10 g to 1 kg AS/ha, especially 20 g to 600 g AS/ha. For usage as a seed dressing, it is advantageous to use dosages of 10 mg to 1 g active substance per kg of seed grain.

While concentrated compositions are preferred for commercial usage, the end user normally uses diluted compositions.

Formulations may be prepared analogously to those described for example in WO 97/33890.

EXAMPLES

The subsequent examples are intended to illustrate the invention, without however limiting the scope thereof.

Synthesis Example 1

N-{4-[2-(1-Dimethylamino-ethylimino)-4-phenyl-thiazol-5-yl]-pyrimidin-2-yl}-N-phenyl-amine

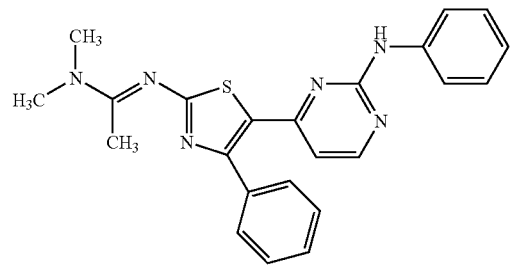

a) 2-(2-Methylthio-pyrimidin-4-yl)-1-phenyl-ethanone

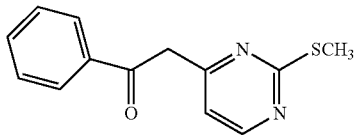

A mixture of 4-methyl-2-methylthio-pyrimidine (30 g, 0.21 mol) and methyl benzoate (30 g, 0.21 mol) is added to a solution of potassium tert-butoxide (54 g, 0.48 mol) in tetrahydrofuran (350 ml) with cooling in such a way that the reaction temperature does not exceed +20° C. After stirring the mixture for additional 20 minutes the solution is poured onto crushed ice. The resulting solution is acidified with concentrated hydrochloric acid and extracted with ethyl acetate. Drying of the organic phase, filtering and evaporation of the solvent under reduced pressure gives the 2-(2-methylthio-pyrimidin-4-yl)-1-phenyl-ethanone in form of a mixture of tautomers.

b) 2-Bromo-2-(2-methylthio-primidin-4-yl)-1-phenyl-ethanone

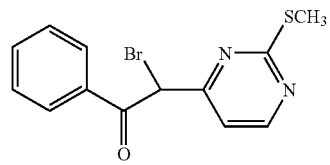

Bromine (24.1 g, 0.15 mol) is added with stirring to 2-(2-methylthio-pyrimidin-4-yl)-1-phenyl-ethanone (36.8 g, 0.15 mol) in acetic acid (300 ml) in such a way that the reaction temperature does not exceed +25° C. and the color of the bromine is discharged immediately. After the addition of the bromine solution the solvent is removed by evaporation under vacuum. The pH of the resulting oil is adjusted to 8 using an aqueous saturated sodium bicarbonate solution and the product is extracted several times with diethylther.

Drying the combined extracts with magnesium sulfate, filtering and evaporation of the solvent gives the crude 2-bromo-2-(2-methylthio-pyrimidin-4-yl)-1-phenyl-ethanone in form of an oil of sufficient purity for the following step.

c) 4-(2-Amino-4-phenyl-thiazol-5-yl)-2-methylthio-pyrimidine

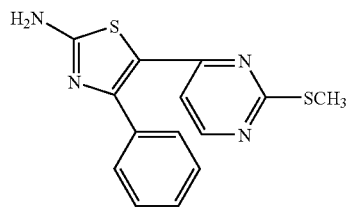

A solution of 2-bromo-2-(2-methylthio-pyrimidin-4-yl)-1-phenyl-ethanone (45 g, 0.14 mol) and thiourea (21.2 g, 0.28 mol) in ethanol (300 ml) is heated at reflux for 4 hours. On cooling the product starts to crystallize as salt. It is filtered with suction and washed with ether. The free amine is obtained by partitioning of the product between an aqueous solution of sodium bicarbonate and a 1:1 mixture of ethyl acetate and tetrahydrofuran, followed by drying of the organic phase over magnesium sulfate, filtering and evaporation of the solvents. The 4-(2-amino-4-phenyl-thiazol-5-yl)-2-methylthio-pyrimidine is obtained in crystalline form, m.p. 208–209° C.

d) 4-(2-Amino-4-phenyl-thiazol-5-yl)-2-methylsulfinyl-pyrimidine

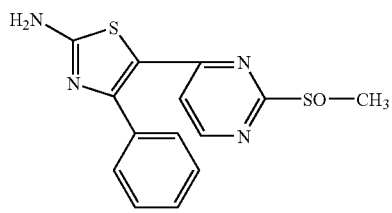

A suspension of 4-(2-amino-4-phenyl-thiazol-5-yl)-2-methylthio-pyrimidine (16.5 g, 0.055 mol) in methylene chloride (350 ml) is cooled to 0° C. After the addition of m-chloro perbenzoic acid (14.9 g, content of 70% peracid, 0.06 mol) in 5 portions the resulting solution is stirred for an additional hour. The reaction mixture is neutralized by addition of a saturated aqueous solution of sodium bicarbonate yielding a crystalline suspension of the product. After addition of hexane the precipitated 4-(2-amino-4-phenyl-thiazol-5-yl)-2-methylsulfinyl-pyrimidine is filtered with suction, washed with water and diethyl ether and finally dried at +50° C. under high vacuum.

e) N-[4-(2-Amino-4-phenyl-thiazol-5-yl)-pyrimidin-2-yl]-N-phenyl-amine

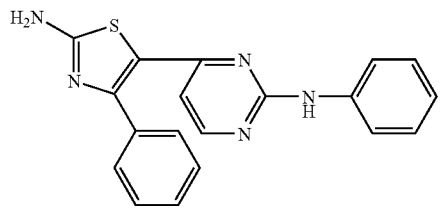

A mixture of 4-(2-amino-4-phenyl-thiazol-5-yl)-2-methylsulfinyl-pyrimidine (0.5 g, 1.58 mmol) and aniline (1.5 g, 15.8 mmol) is heated at +100° C. After the addition of boron trifluoride diethyl etherate (3 drops) the solution is heated at +150° C. for half an hour. On cooling the product starts to crystallize. The crystals are filtered and washed thoroughly with diethyl ether to give the N-[4-(2-amino-4-phenyl-thiazol-5-yl)-pyrimidin-2-yl]-N-phenyl-amine in pure form, having a m.p. of 244–245° C.

f) A suspension of [4-(2-amino-4-phenyl-thiazol-5-yl)-pyrimidin-2-yl]-phenyl-amine (0.28 g, 0.81 mmol) in dimethylacetamide dimethylacetal (0.22 g, 1.62 mmol) and dimethylformamide (10 ml) is heated at 140° C. for 4 hours. After distilling off all volatile compounds the residue is purified by chromatography on silicagel (eluent: ethyl acetate/hexane) to give in form of a yellow powder, m.p. 196–197° C.

Synthesis Example 2

N-[4-(2-Acetylamino-4-phenyl-thiazol-5-yl)-pyrimidin-2-yl]-N phenyl-amine

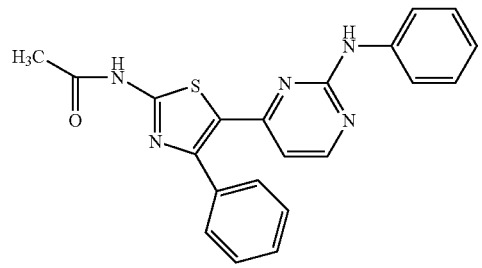

A suspension of N-[4-(2-amino-4-phenyl-thiazol-5-yl)-pyrimidin-2-yl]-N-phenyl-amine (0.25 g, 0.7 mmol), acetic acid anhydride (0.11 mg, 1.1 mmol), triethylamine (0.11 mg, 1.1 mmol) and a catalytic amount of N,N-dimethylaminopyridine is heated at reflux for 18 hours. The volatiles are evaporated under reduced pressure and the product is crystallized by the addition of diethyl ether. Filtering and drying gives the N-[4-(2-acetylamino-4-phenyl-thiazol-5-yl)-pyrimidin-2-yl]-N-phenyl-amine, m.p. >260° C.

Synthesis Example 3

N-{4-[2-(3-Methylbutyl-amino)-4-phenyl-thiazol-5-yl]-pyrimidin-2-yl}-N-phenyl-amine

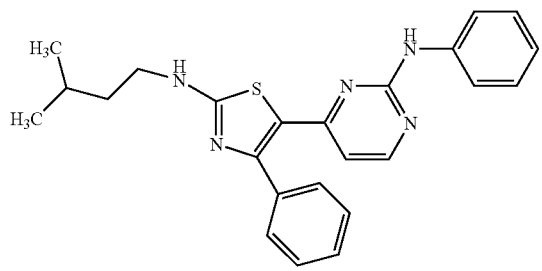

Sodium cyanoborohydride (92 mg, 1.3 mmol) is added at room temperature to a suspension of N-[4-(2-amino-4-phenyl-thiazol-5-yl)-pyrimidin-2-yl]-N-phenyl-amine (150 mg, 0.4 mmol) and isovalerianaldehyde (113 mg, 1.3 mmol) in a mixture of methanol (13 ml), acetic acid (0.3 ml) and water (0.05 ml). The reaction mixture is stirred at room temperature for 18 hours. Partitioning of the mixture between water and ethyl acetate, drying over magnesium sulfate, filtering and evaporating of the solvents under reduced pressure gives the crude product. After crystallization from a mixture of diethyl ether and hexane the N-{4-[2-(3-methylbutyl-amino)-4-phenyl-thiazol-5-yl]-pyrimidin-2-yl}-N-phenyl-amine has a m.p. of 170–172° C.

Synthesis Example 4

N-[4-(2-Amino-4-phenyl-thiazol-5-yl)-primidin-2-yl]-N-[3-(3-hydroxy-3-methyl-1-butynyl)-phenyl]-amine

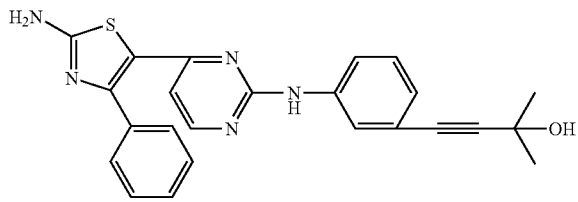

a) N-[4-(2-Amino-4-phenyl-thiazol-5-yl)-pyrimidin-2-yl]-N-(3-iodo-phenyl)-amine

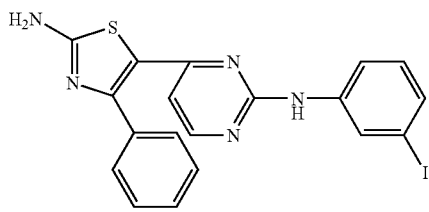

A mixture of 5-(2-methylsulfinyl-pyrimidin-4-yl)-4-phenyl-2-amino-thiazole (2.0 g, 6.3 mmol) and m-iodoaniline (7.0 g, 31.6 mmol) is heated at +100° C. After the addition of boron trifluoride diethyl etherate (3 drops) the solution is heated at +150° C. for half an hour. On cooling the product starts to crystallize. The N-[4-(2-amino-4-phenyl-thiazol-5-yl)-pyrimidin-2-yl]-N-(3-iodo-phenyl)-amine after chromatography (eluent: 2:1 mixture of ethyl acetate/hexane) has a m.p. of 243–244° C.

b) A suspension of N-[4-(2-amino-4-phenyl-thiazol-5-yl)-pyrimidin-2-yl]-N-(3-iodo-phenyl)-amine (300 mg, 0.64 mmol) and 2-methyl-3-butyn-2-ol (110 mg, 1.3 mmol) in dimethylformamide (20 ml) and diisopropylamine (5 ml) are stirred in the presence of bis triphenylphosphine palladium-dichloride (20 mg), triphenylphosphine (20 mg) and copper iodide under a nitrogen atmosphere for 16 hours. After an aqueous work-up the residue is purified by chromatography (eluent: 1:2 mixture of ethyl acetate/hexane) to give the N-[4-(2-amino-4-phenyl-thiazol-5-yl)-pyrimidin-2-yl]-N-[3-(3-hydroxy-3-methyl-1-butynyl)-phenyl]-amine, m.p. 262–263° C.

Synthesis Example 5

N-[4-(2-Amino-4-phenyl-thiazol-5-yl)-pyrimidin-2-yl]-N-(3',4'-dimethoxy-biphenyl-3-yl)-amine

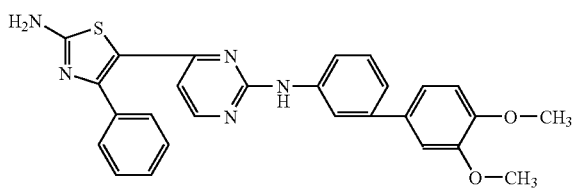

A solution of N-[4-(2-amino-4-phenyl-thiazol-5-yl)-pyrimidin-2-yl]-N-(3-iodo-phenyl)-amine (300 mg, 0.64 mmol) and 3,4-dimethoxyphenylboronic acid (122 mg, 0.66 mmol) in dimethoxyethane (8 ml) and aqueous potassium carbonate (13 ml) are stirred in the presence of tetrakis triphenylphosphine palladium (15 mg) under a nitrogen atmosphere at reflux for 1 hour. After an aqueous work-up the residue is purified by chromatography (eluent: 2:1 mixture of ethyl acetate/hexane) to give the N-[4-(2-amino-4-phenyl-thiazol-5-yl)-pyrimidin-2-yl]-N-(3',4'-dimethoxy-biphenyl-3-yl)-amine, m.p. 236–237° C.

Synthesis Example 6

N-[4-(2-Amino-4-phenyl-thiazol-5-yl)-pyrimidin-2-yl]-N-[3-(2-hydroxy-2-methyl-ethyl)-phenyl]-amine

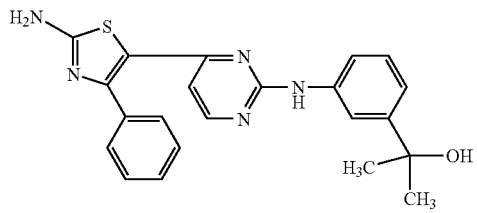

a) N-[4-(2-Amino-4-phenyl-thiazol-5-yl)-pyrimidin-2-yl]-N-(3-methoxycarbonyl-phenyl)-amine A mixture of 2-amino-4-phenyl-5-(2-methylsulfinyl-pyrimidin-4-yl)-thiazole (2.0 g, 6.3 mmol) and m-amino benzoic acid methyl ester (13.0 g, 90 mmol) is heated at +100° C. After the addition of boron trifluoride diethyl etherate (3 drops) the solution is heated at +150° C. for half an hour. After chromatography (eluent: ethyl acetate/hexane) the N-[4-(2-amino-4-phenyl-thiazol-5-yl)-pyrimidin-2-yl]-N-(3-methoxycarbonyl-phenyl)-amine has a m.p. of 223–225° C.

b) To a suspension of N-[4-(2-amino-4-phenyl-thiazol-5-yl)-pyrimidin-2-yl]-N-(3-methoxycarbonyl-phenyl)-amine (800 mg, 2.0 mmol) in tetrahydrofuran (30 ml) is added a solution of methyl magnesium chloride (6 ml of a 20% THF solution) without cooling. The temperature of the reaction mixture rises to about +45° C. and the starting material dissolves immediately yielding a yellow clear solution. After an additional hour the solution is poured onto crushed ice and ammonium chloride. The colorless precipitate is filtered and washed with ethyl acetate and tetrahydrofuran. The organic phases are pooled, dried and concentrated under reduced pressure. Chromatography of the resulting solid gives the N-[4-(2-amino-4-phenyl-thiazol-5-yl)-pyrimidin-2-yl]-N-[3-(2-hydroxy-2-methyl-ethyl)-phenyl]-amine, m.p. 219–220° C.

Synthesis Example 7

N-[4-(2-Amino-4-phenyl-thiazol-5-yl)-pyrimidin-2-yl]-N-(3-hydroxymethyl-phenyl)-amine

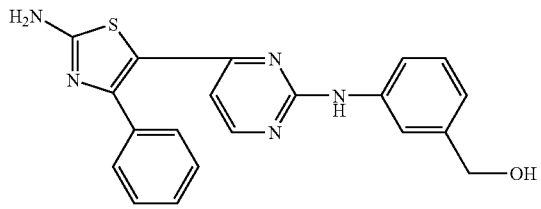

To a suspension of N-[4-(2-amino-4-phenyl-thiazol-5-yl)-pyrimidin-2-yl]-N-(3-methoxycarbonyl-phenyl)-amine (800 mg, 2.0 mmol) in tetrahydrofuran (25 ml) is added a solution of sodium dihydro-bis(2-methoxyethoxy)aluminate in toluene (3 ml of a 3.5M solution) without cooling. The temperature of the reaction mixture rises to about +40° C. and the starting material dissolves immediately yielding a yellow clear solution. After an additional hour the solution is poured onto crushed ice and ammonium chloride. The colorless precipitate is filtered and washed with ethyl acetate and tetrahydrofuran. The organic phases are pooled, dried and concentrated under reduced pressure. Chromatography of the resulting solid gives the N-[4-(2-amino-4-phenyl-thiazol-5-yl)-pyrimidin-2-yl]-N-(3-hydroxymethyl-phenyl)-amine, m.p. 214–215° C.

Synthesis Example 8

N-[4-(2-Amino-4-phenyl-thiazol-5-yl)-pyrimidin-2-yl]-N-phenyl-amine

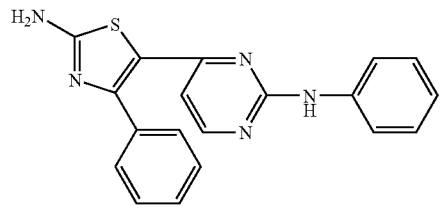

a) 2-[N,N-bis(2,2-Dimethylethoxycarbonyl)]-amino]-4-phenyl-thiazole

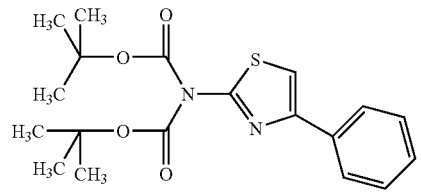

2-Amino-4-phenyl-thiazole (5.0 g, 28.4 mmol) is solved in 200 ml of dry THF and a solution of di-tert-butyl pyrocarbonate (13.6 g, 62.5 mmol) in THF is slowly (dropwise) added. A catalytic amount of DMAP is added to the reaction mixture before heating it to reflux for 12 hours. Work-up: after cooling to +25° C. the reaction solution is poured on ice, acidified with 2N HCl and extracted with diethylether. The organic phase is separated, dried with $Na_2SO_4$, filtered and the solvent is evaporated. The residue is purified by chromatography over silica gel (eluent: PE/EE=20:1). The 2-[N,N-bis(2,2-dimethylethoxycarbonyl)-amino]-4-phenyl-thiazole is obtained in form of a highly viscous oil.
$^1$H-NMR (CDCl$_3$): 1.48 (s, 18H, CH$_3$), 7.18 (s, 1H, H-5), 7.22–7.35 (m, 3H, H-3',4'), 7.79 (d, 2H, H-2')

b) 2-(2,2-Dimethylethoxycarbonyl-amino)-4-phenyl-thiazole

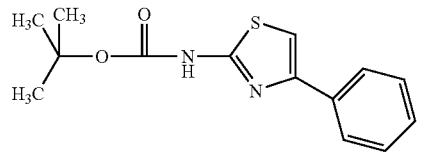

The 2-[N,N-bis(2,2-dimethylethoxycarbonyl)-amino]-4-phenyl-thiazole (10.7 g, 28.4 mmol) is suspended in 100 mL of dry $CH_2Cl_2$ and 5 equivalents of trifluoroacetic acid are added. The mixture is stirred at +25° C. while test samples are taken and analyzed by TLC until no starting material is left.

Work-up: The reaction mixture is poured into water, basified with saturated aqueous $Na_2CO_3$-solution and extracted with $CH_2Cl_2$. The organic phases are combined, washed with saturated aqueous $NaHCO_3$-solution and saturated brine, dried with $Na_2SO_4$. The solvent is evaporated and the residue is dried in high vacuum. This quantitative obtained crude intermediate 2-[N,N-bis(2,2-dimethyl-ethoxycarbonyl)-amino-4-phenylthiazole is directly used for the following reaction step.

Yield: yellow highly viscous residue that builds a foam and solidifies when the last traces of solvent are evaporated, having a m.p.: 65–70° C.

$^1$H-NMR (CDCl$_3$): 1.20 (s, 9H, C(CH$_3$)$_3$), 7.04 (s, 1H, H-5), 7.20–7.38 (m, 3H, H-3',4'), 7.70–7.80 (d, 2H, H-2', $J_{2'3'}$=20 Hz)

c) 4-[2-(2,2-Dimethylethoxycarbonyl-amino)-4-phenyl-thiazol-5-yl]-2-iodo-pyrimidine

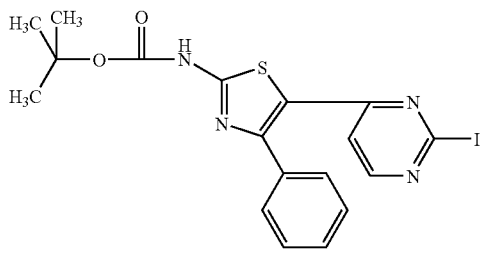

The 2-[N,N-bis(2,2-dimethylethoxycarbonyl)-amino-4-phenyl-thiazole (0.50 g, 1.89 mmol) is solved under a nitrogen atmosphere in 35 mL of dry THF. The solution is cooled to –78° C. and a solution of n-BuLi in hexane (4.16 mmol) is added. The mixture is allowed to warm to –20° C. and stirred for 1.5 hours at this temperature. Then the mixture is again cooled to –78° C. and pre-dried ZnCl$_2$ (0.28 g, 2.08 mmol) in a small volume of dry THF is added dropwise at a rate which allows to keep the temperature of the mixture below –60° C. During the following 1.5 hours the mixture is warmed to +25° C., Pd(PPh$_3$)$_4$ (0.011 g) and 2,4-diiodopyrimidine (0.63 g, 1.89 mmol) are added. The mixture is heated to reflux for 3 hours.

Work-up: The reaction mixture is poured on aqueous solution of EDTA, basified with saturated aqueous Na$_2$CO$_3$-solution and extracted with diethyl ether. The crude 4-[2-(2,2-dimethylethoxycarbonyl-amino)-4-phenyl-thiazol-5-yl]-2-iodo-pyrimidine is purified by column chromatography on silica gel (eluent: PE/EE=4:1).

Yield: brownish crystals; m.p.: 135–138° C.

$^1$H-NMR (CDCl$_3$): 1.49 (s, 9H, CH$_3$), 6.98 (d, 1H, H-5", $J_{5''6''}$=5 Hz), 7.35–7.57 (m, 5H, phenyl), 8.03 (d, 1H, H-6"), 9.00 (bs, 1H, NH).

d) N-{4-[2-(2,2-Dimethylethoxycarbonyl-amino)-4-phenyl-thiazol-5-yl]-pyrimidin-2-yl}-N-phenyl-amine

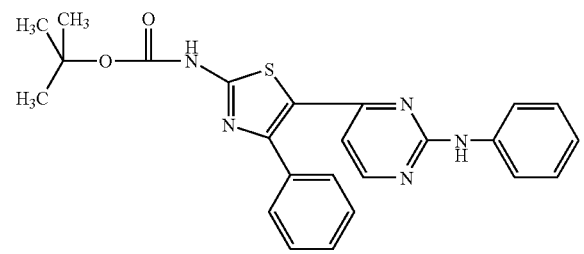

The 4-[2-(2,2-dimethylethoxycarbonyl-amino)-4-phenyl-thiazol-5-yl]-2-iodo-pyrimidine (0.082 g, 0.17 mmol) is heated to reflux with aniline (0.032 g, 0.34 mmol) and dry p-toluene sulfonic acid (0.026 g, 0.136 mmol) in dry dioxane for five hours.

Work-up: after cooling to room temperature the mixture is concentrated until nearly no solvent is present, poured into water, basified with saturated aqueous Na$_2$CO$_3$-solution and extracted with ethyl acetate. The combined organic extracts are washed with brine, dried and the solvent is evaporated. The crude N-{4-[2-(2,2-dimethylethoxycarbonyl-amino)-4-phenyl-thiazol-5-yl]-pyrimidin-2-yl}-N-phenyl-amine is purified by chromatography (silica gel, PE/EE 4:1), yield the pure product as brownish crystals, having the m.p.: 290–292° C.

$^1$H-NMR (DMSO-d$_6$): 1.55 (s, 9H, CH$_3$), 6.42 (d, 1H, H-5", $J_{5''6''}$=5 Hz), 6.90 (t, 1H, H-4a, $J_{4a3a}$=10 Hz), 7.28 (t, 2H, H-3a, $J_{2a3a}$=10 Hz), 7.40–7.60 (m, 5H, phenyl), 7.73 (d, 2H, H-2a), 8.20 (d, 1H, H-6"), 9.60 (s, 1H, NH), 11.79 (s, 1H, NHCO)

$^{13}$C-NMR (DMSO-d$_6$): 27.8 (q, CH$_3$), 81.7 (s, $\underline{C}$(CH$_3$)$_3$), 107.8 (d), 118.8 (d), 121.4 (d), 124.9 (s), 128.4 (d, 2C), 128.6 (d, 2C), 128.9 (d), 129.0 (d, 2C), 135.2 (s), 140.3 (s), 150.6 (s), 152.8 (s), 157.8 (d), 158.6 (s), 159.6 (s), 160.6 (s)

e) The N-{4-[2-(2,2-dimethylethoxycarbonyl-amino)-4-phenyl-thiazol-5-yl]-pyrimidin-2-yl}-N-phenyl-amine (0.12 g, 0.27 mmol) is suspended in 5 mL of dry CH$_2$Cl$_2$ and treated with 5 equivalents of trifluoroacetic acid. The reaction mixture is stirred for 12 hours at +25° C., then poured into water, basified with saturated aqueous Na$_2$CO$_3$-solution and extracted with ethyl acetate. The combined organic extracts are concentrated to dryness and the last traces of solvent are evaporated in high vacuum.

Yield: pure N-[4-(2-amino-4-phenyl-thiazol-5-yl)-pyrimidin-2-yl]-N-phenyl-amine in form of yellow crystals of low solubility having a m.p. of 247–250° C., $^1$H-NMR (DMSO-d$_6$): 6.25 (d, 1H, H-5", $J_{5''6''}$=5 Hz), 6.92 (t, 1H, H-4a, $J_{4a5a}$=7 Hz), 7.25 (t, 2H, H-3a, $J_{2a3a}$=8 Hz), 7.40–7.53 (m, 5H, phenyl), 7.60 (s, 2H, NH$_2$), 7.73 (d, 2H, H-2a), 8.06 (d, 1H, H-6"), 9.45 (s, 1H, NH).

$^{13}$C-NMR (DMSO-d$_6$): 106.8 (d), 118.7 (d, 2C), 119.4 (s), 121.2 (d), 128.3 (d, 2C), 128.5 (d), 128.7 (d, 2C), 128.9 (d, 2C), 135.9 (s), 140.5 (s), 153.3 (s), 157.0 (d), 158.7 (s), 159.5 (s), 169.1 (s)

Synthesis Example 9

N-[4-(2-Amino-4-phenyl-thiazol-5-yl)-pyrimidin-2-yl]-N-(3-chloro-phenyl)-amine

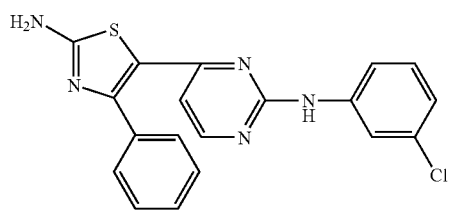

a) N-{4-[2-(2,2-Dimethylethoxycarbonyl-amino)-4-(3-chloro-phenyl)-thiazol-5-yl]-pyrimidin-2-yl}-N-phenyl-amine

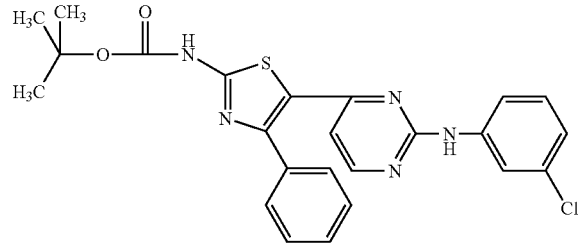

The 4-[2-(2,2-dimethylethoxycarbonyl-amino)-4-phenyl-thiazol-5-yl]-2-iodo-pyrimidine (0.20 g, 0.416 mmol) is heated to reflux with 3-chloro-aniline (0.106 g, 0.833 mmol) and dry p-toluene sulfonic acid (0.064 g, 0.33 mmol) in dry dioxane for five hours.

Work-up: after cooling to room temperature the mixture is concentrated until nearly no solvent is present, poured into water, basified with saturated aqueous $Na_2CO_3$-solution and extracted with ethyl acetate. The combined organic extracts are washed with brine, dried and the solvent is evaporated. The crude N-{4-[2-(2,2-dimethylethoxycarbonyl-amino)-4-(3-chloro-phenyl)-thiazol-5-yl)]-pyrimidin-2-yl}-N-phenyl-amine is purified by chromatography (silica gel, PE/EE=2:1), yield the pure product as yellow crystals, having the m.p.: 295–298° C.

$^1$H-NMR (DMSO-$d_6$): 1.52 (s, 9H, $CH_3$), 6.46 (d, 1H, H-5", $J_{5''6''}$=5 Hz), 6.97 (d, 1H, H-4a, $J_{4a5a}$=10 Hz), 7.29 (t, 1H, H-5a, $J_{5a6a}$=10 Hz), 7.40–7.60 (m, 5H, phenyl), 7.63 (d, 1H, H-6a), 8.05 (s, 1H, H-2a), 8.23 (d, 1H, H-6"), 9.85 (s, 1H, NH), 11.80 (s, 1H, NHCO)

$^{13}$C-NMR (DMSO-$d_6$): 27.8 (q, $CH_3$), 81.7 (s, $\underline{C}(CH_3)_3$), 108.2 (d), 117.0 (d), 117.9 (d), 120.8 (d), 124.7 (s), 128.6 (d, 2C), 128.9 (d, 2C), 130.0 (d), 133.0 (s), 135.1 (s), 141.9 (s), 150.9 (s), 152.8 (s), 157.8 (d), 158.7 (s), 159.3 (s), 160.8 (s).

b) The N-{4-[2-(2,2-dimethylethoxycarbonyl-amino)-4-(3-chloro-phenyl)-thiazol-5-yl]-pyrimidin-2-yl}-N-phenyl-amine (0.05 g, 0.11 mmol) is suspended in 5 mL of dry $CH_2Cl_2$ and treated with 2 equivalents of trifluoroacetic acid. The reaction mixture is stirred for 48 hours at +25° C., then poured into water, basified with saturated aqueous $Na_2CO_3$-solution and extracted with ethyl acetate. The combined organic extracts are concentrated to dryness and the last traces of solvent are evaporated in high vacuum.

Yield: pure N-[4-(2-amino-4-phenyl-thiazol-5-yl)-pyrimidin-2-yl]-N-(3-chloro-phenyl)-amine in form of yellow crystals of low solubility having a m.p. of 243–245° C.

$^1$H-NMR (DMSO-$d_6$): 6.28 (d, 1H, H-5", $J_{5''6''}$=5 Hz), 6.97 (d, 1H, H-4a, $J_{4a5a}$=7 Hz), 7.27 (t, 1H, H-5a, $J_{5a6a}$=8 Hz), 7.40–7.55 (m, 5H, phenyl), 7.55–7.75 (m, 1H, H-6a), 7.65 (s, 2H, $NH_2$), 8.00 (t, 1H, H-2a, long-dist.-J=1 Hz), 8.10 (d, 1H, H-6"), 9.70 (s, 1H, NH)

Synthesis Example 10

N-[4-(2-Amino-4-phenyl-thiazol-5-yl)-pyrimidin-2-yl]-N-(3-fluoro-phenyl)-amine

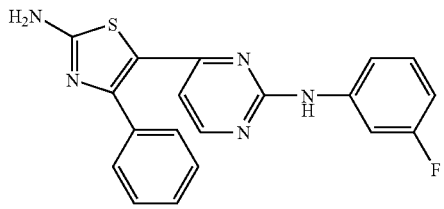

a) N-{4-[2-(2,2-Dimethylethoxycarbonyl-amino)-4-(3-fluoro-phenyl)-thiazol-5-yl]-pyrimidin-2-yl}-N-phenyl-amine

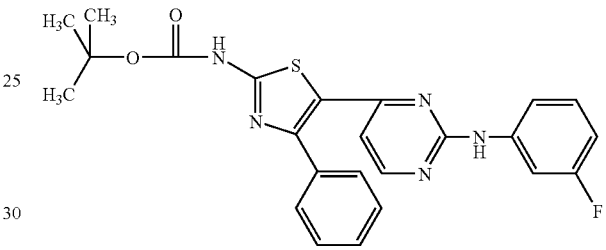

The 4-[-2-(2,2-dimethylethoxycarbonyl-amino)-4-phenyl-thiazol-5-yl]-2-iodo-pyrimidine (0.40 g, 0.83 mmol) is heated to reflux with 3-fluoro-aniline (0.185 g, 1.66 mmol) and dry p-toluene sulfonic acid (0.127 g, 0.66 mmol) in dry dioxane for four hours.

Work-up: after cooling to room temperature the mixture is concentrated until nearly no solvent is present, poured into water, basified with saturated aqueous $Na_2CO_3$-solution and extracted with ethyl acetate. The combined organic extracts are washed with brine, dried and the solvent is evaporated. The crude N-{4-[2-(2,2-dimethylethoxycarbonyl-amino)-4-(3-fluoro-phenyl)-thiazol-5-yl)]-pyrimidin-2-yl}-N-phenyl-amine is purified by chromatography (silica gel, PE/EE=2:1), yield the pure product as brownish crystals, having the m.p.: 294–297° C.

$^1$H-NMR (DMSO-$d_6$): 1.52 (s, 9H, $CH_3$), 6.48 (d, 1H, H-5", $J_{5''6''}$=5 Hz), 6.78 (t, 1H, H-4a, $J_{4a5a}$=10 Hz, $J_{4aF}$=10 Hz), 7.30 (q, 1H, H-5a, $J_{5a6a}$=10 Hz, $J_{5aF}$=10 Hz), 7.40–7.60 (m, 6H, phenyl, H-6a), 7.82 (dt, 1H, H-2a, $J_{2aF}$=14 Hz, long-dist.-J=2 Hz), 8.25 (d, 1H, H-6"), 9.85 (s, 1H, NH), 11.80 (s, 1H, NHCO).

$^{13}$C-NMR (DMSO-$d_6$): 27.8 (q, $CH_3$), 81.7 (s, $\underline{C}(CH_3)_3$), 105.2 (dd, C-2a, $J_{2aF}$=27 Hz), 107.5 (dd, C-4a, $J_{4aF}$=21 Hz), 108.3 (d), 114.4 (d, C-6a), 124.7 (s), 128.6 (d, 2C), 129.0 (d, 2C), 129.7 (d), 129.9 (d), 135.1 (s), 142.2 (d, C-1a, $J_{1aF}$=11 Hz), 150.9 (s), 152.8 (s), 157.8 (d), 158.7 (s), 159.4 (s), 160.8 (s), 162.3 (d, C-3a, $J_{3aF}$=240 Hz)

b) The N-{4-[2-(2,2-dimethylethoxycarbonyl-amino)-4-(3-fluoro-phenyl)-thiazol-5-yl]-pyrimidin-2-yl}-N-phenyl-amine (0.05 g, 0.11 mmol) is suspended in 5 mL of dry $CH_2Cl_2$ and treated with 5 equivalents of trifluoroacetic acid.

The reaction mixture is stirred for 12 hours at +25° C., then poured into water, basified with saturated aqueous Na$_2$CO$_3$-solution and extracted with ethyl acetate. The combined organic extracts are concentrated to dryness and the last traces of solvent are evaporated in high vacuum.

Yield: pure N-[4-(2-amino-4-phenyl-thiazol-5-yl)-pyrimidin-2-yl]-N-(3-fluoro-phenyl)-amine in form of yellow crystals of low solubility having a m.p. of 243–245° C.

$^1$H-NMR (DMSO-d$_6$): 6.31 (d, 1H, H-5", J$_{5''6''}$=5 Hz), 6.75 (t, 1H, H-4a, J$_{4a5a}$=8 Hz, J$_{4aF}$=8 Hz), 7.28 (q, 1H, H-5a, J$_{5a6a}$=8 Hz, J$_{5aF}$=8 Hz), 7.38–7.60 (m, 6H, phenyl, H-6a), 7.19 (s, 2H, NH$_2$), 7.83 (d, 1H, H-2a, J$_{2aF}$=12 Hz), 8.12 (d, 1H, H-6"), 9.23 (s, 1H, NH)

$^{13}$C-NMR (DMSO-d$_6$): 105.1 (dd, J$_{CF}$=27 Hz), 107.3 (dd, J$_{CF}$=21 Hz), 107.4 (d), 114.4 (d), 119.2 (s), 128.6 (d, 2C), 128.8 (d, C-4'), 128.9 (d, 2C), 129.8 (dd, C-5a, J$_{5aF}$=10 Hz), 135.9 (s), 142.4 (d, C-1a, J$_{1aF}$=11 Hz), 153.7 (s), 157.0 (d), 158.8 (s), 159.3 (s), 162.4 (d, C-3a, J$_{3aF}$=240 Hz), 169.2 (s, C-2).

Synthesis Example 11

N-[4-(2-Amino-4-phenyl-thiazol-5-yl)-pyrimidin-2-yl]-N-(3-methoxy-phenyl)-amine

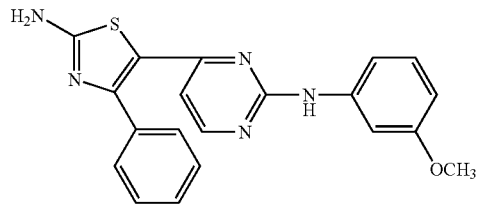

The 4-[2-(2,2-dimethylethoxycarbonyl-amino)-4-phenyl-thiazol-5-yl]-2-iodo-pyrimidine (1.0 g, 2.1 mmol) is heated to reflux with 3-methoxy-aniline (0.32 g, 0.29 mL) and p-toluene sulfonic acid-mono hydrate (0.34 g, 1.8 mmol) in dioxane for four hours.

Work-up: when TLC-control indicates quantitative conversion (but still 2-spots at R$_f$=0.23 and 0.09, PE/EE 2:1) and after cooling to room temperature the mixture is concentrated until nearly no solvent is present, poured into a mixture ethyl acetate and water, basified with saturated aqueous Na$_2$CO$_3$-solution and extracted with ethyl acetate. The combined organic extracts are dried with Na$_2$SO$_4$ and the solvent is evaporated. 0.87 g of a brown residue remains. According to NMR-check this raw product contains about 67% of the desired N-[4-(2-amino-4-phenyl-thiazol-5-yl)-pyrimidin-2-yl]-N-(3-methoxy-phenyl)-amine and a more polar product. The amount necessary for the NMR is easily solved in CDCl$_3$ while larger quantities of are difficult to solve in CHCl$_3$, ethyl acetate or DMSO, whereby the desired title product resolves easier than the main by-product. The raw product-mixture is digerated with a small quantity of CHCl$_3$ in order to separate it from the darkly colored impurities. The CHCl$_3$-phase which contains most of the title product is decanted rapidly. 100 mg of the so-obtained raw-product-mixture is stirred in 1 ml of TFA/CH$_2$Cl$_2$ (1:1) for 12 hours.

Work-up: TLC control of the solution reveals only one spot at R$_f$=0.09. The reaction solution is transferred to a separation funnel with ethyl acetate, neutralized with saturated aqueous NaHCO$_3$-solution and extracted with ethyl acetate. The combined organic phase is dried with Na$_2$SO$_4$ and the solvent is evaporated. The pure N-[4-(2-amino-4-phenyl-thiazol-5-yl)-pyrimidin-2-yl]-N-(3-methoxy-phenyl)-amine is obtained as yellow crystals in quantitative yield having a m.p. of 115–117° C.

$^1$H-NMR (DMSO-d$_6$): 3.76 (s, 3H, CH$_3$), 6.24 (d, 1H, H-5", J$_{5''6''}$=5 Hz), 6.52 (d, 1H, J=8 Hz), 7.14 (t, 1H, J=8 Hz), 7.29 (d, 1H, J=8 Hz), 7.40–7.55 (m, 6H, phenyl+1H), 7.63 (s, 2H, NH$_2$), 8.06 (d, 1H, H-6"), 8.10 (d, 1H, H-6"), 9.44 (s, 1H, NH).

Synthesis Example 12

N-{4-[2-(4-Methylpiperazin-1-yl)-4-phenyl-thiazol-5-yl]-pyrimidin-2-yl}-N-phenyl-amine

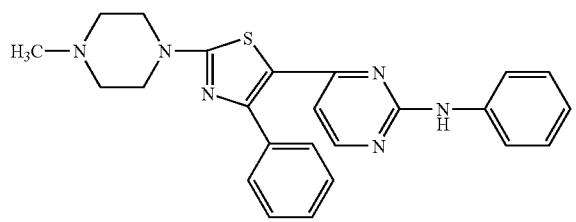

a) 4-(2-Chloro-4-phenyl-thiazol-5-yl)-2-methylsulfinyl-pyrimidine

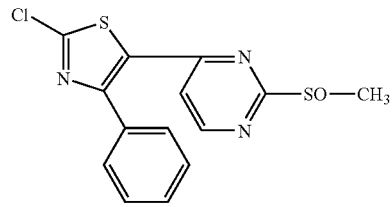

To a suspension of copper-II-chloride (3.2 g, 23.5 mmol) and t-butylnitrite (2.9 g, 27.5 mmol) in acetonitrile (300 ml) is added 4-(2-amino-4-phenyl-thiazol-5-yl)-2-methylsulfinyl-pyrimidine (6.2 g, 19.6 mmol) in small portions at room temperature. After stirring for three hours at room temperature the reaction mixture is diluted with ethyl acetate and washed repeatedly with water. Drying over magnesium sulfate, filtering, evaporating the solvents and purification by chromatography gives the 4-(2-chloro-4-phenyl-thiazol-5-yl)-2-methylsulfinyl-pyrimidine as a yellow colored solid.

b) 4-[2-(4-Methylpiperazin-1-yl)-4-phenyl-thiazol-5-yl]-2-methylsulfinyl-pyrimidine

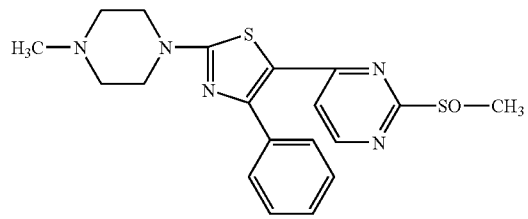

A solution of N-methylpiperazine (0.6 g, 6.0 mmol) in tetrahydrofuran (5 ml) is added to a well stirred solution of 4-(2-chloro-4-phenyl-thiazol-5-yl)-2-methylsulfinyl-pyrimidine (1.0 g, 3.0 mmol) in tetrahydrofuran (20 ml) at +5° C. The reaction mixture is allowed to warm to room temperature over night. Evaporation of the solvent leaves a crystalline residue that is suspended in water, filtered with suction, washed with diethyl ether and dried under vacuum. The product 4-[2-(4-methylpiperazin-1-yl)-4-phenyl-thiazol-5-yl]-2-methylsulfinyl-pyrimidine shows a m.p. of 166–169° C.

c) A mixture of 4-[2-(4-methylpiperazin-1-yl)-4-phenyl-thiazol-5-yl]-2-methylsulfinyl-pyrimidine (0.5 g, 1.25 mmol) and aniline (1.5 g, 15.8 mmol) is heated at +100° C. After the addition of boron trifluoride diethyl etherate (3 drops) the solution is heated at +150° C. for half an hour. After the reaction mixture is cooled to room temperature water and diethylether is added sequentially to precipitate the product. The crystals are filtered and washed thoroughly with diethyl ether to give the N-{4-[2-(4-methylpiperazin-1-yl)-4-phenyl-thiazol-5-yl]-pyrimidin-2-yl}-N-phenyl-amine in pure form, having a m.p. of 239–240° C.

Using analogous procedures to the above described working examples the compounds of the following tables may be obtained.

TABLE 01

Compounds of the general structure I.01, wherein each individual species corresponds to the combination of the definitions $R_1$, $R_2$, $R_3$, $R_4$, $R_5$, und $R_6$ of the lines of table A.

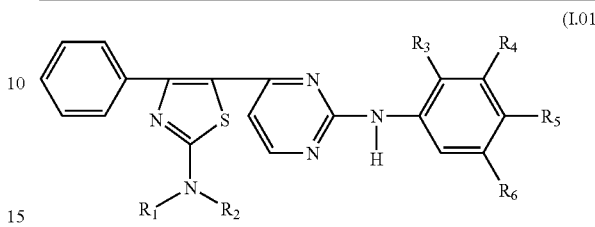

(I.01)

TABLE 02

Compounds of the general structure I.02, wherein each individual species corresponds to the combination of the definitions $R_1$, $R_2$, $R_3$, $R_4$, $R_5$, und $R_6$ of the lines of table A.

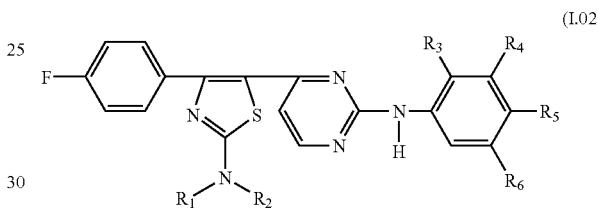

(I.02)

TABLE 03

Compounds of the general structure I.03, wherein each individual species corresponds to the combination of the definitions $R_1$, $R_2$, $R_3$, $R_4$, $R_5$, und $R_6$ of the lines of table A.

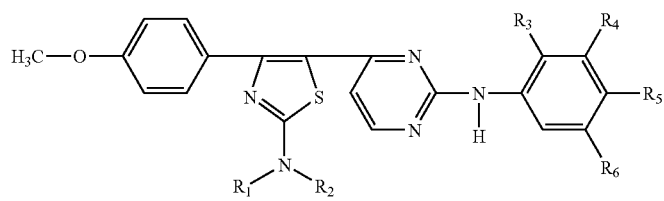

(I.03)

TABLE 04

Compounds of the general structure I.04, wherein each individual species corresponds to the combination of the definitions $R_1$, $R_2$, $R_3$, $R_4$, $R_5$, und $R_6$ of the lines of table A.

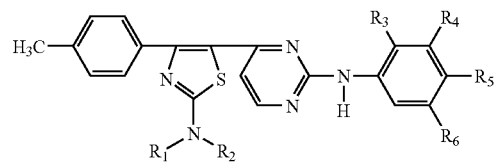

(I.04)

TABLE 05

Compounds of the general structure I.05, wherein each individual species corresponds to the combination of the definitions $R_1$, $R_2$, $R_3$, $R_4$, $R_5$, und $R_6$ of the lines of table A.

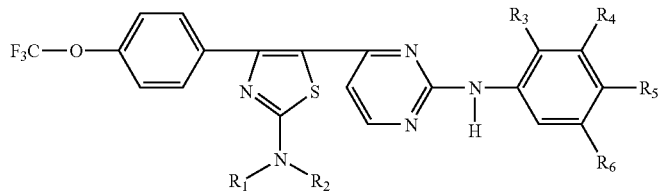

(I.05)

TABLE 06

Compounds of the general structure I.06, wherein each individual species corresponds to the combination of the definitions $R_1$, $R_2$, $R_3$, $R_4$, $R_5$, und $R_6$ of the lines of table A.

(I.06)

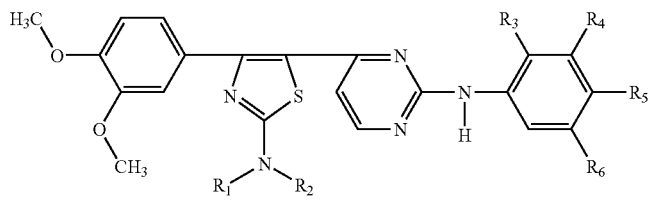

TABLE 07

Compounds of the general structure I.07, wherein each individual species corresponds to the combination of the definitions $R_1$, $R_2$, $R_3$, $R_4$, $R_5$, and $R_6$ of the lines of table A.

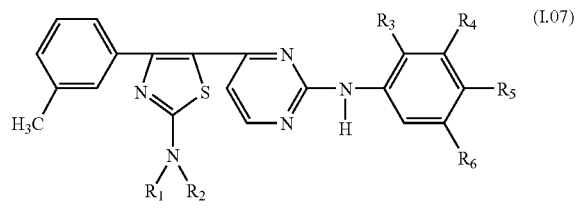
(I.07)

TABLE 08

Compounds of the general structure I.08, wherein each individual species corresponds to the combination of the definitions $R_1$, $R_2$, $R_3$, $R_4$, $R_5$, und $R_6$ of the lines of table A.

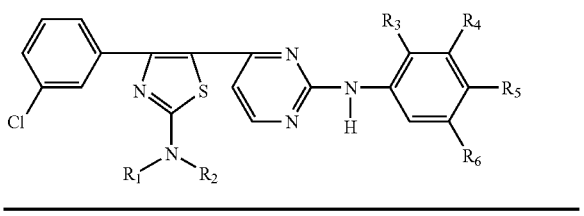
(I.08)

TABLE 09

Compounds of the general structure I.09, wherein each individual species corresponds to the combination of the definitions $R_1$, $R_2$, $R_3$, $R_4$, $R_5$, und $R_6$ of the lines of table A.

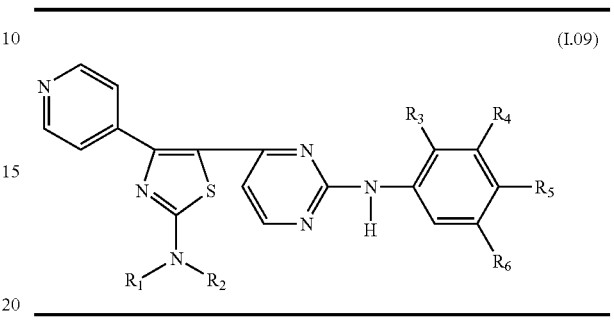
(I.09)

TABLE 10

Compounds of the general structure I.10, wherein each individual species corresponds to the combination of the definitions $R_1$, $R_2$, $R_3$, $R_4$, $R_5$, und $R_6$ of the lines of table A.

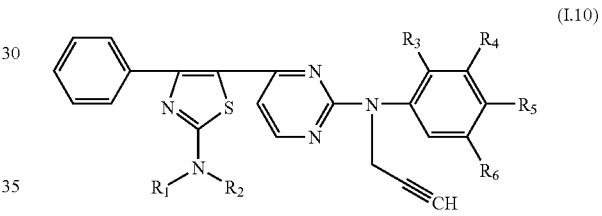
(I.10)

TABLE A

| Comp-No. | $R_1$ | $R_2$ | $R_3$ | $R_4$ | $R_5$ | $R_6$ |
|---|---|---|---|---|---|---|
| 0001 | H | H | H | —CH$_2$—O—CH$_3$ | H | H |
| 0002 | H | H | H | —NH—CO—CH$_3$ | H | H |
| 0003 | H | H | H | —CH$_2$—NH—CO—CH$_3$ | H | H |
| 0004 | H | H | H | —CH(CH$_3$)—NH—CO—CH$_3$ | H | H |
| 0005 | H | H | H | —C(CH$_3$)$_2$—NH—CO—CH$_3$ | H | H |
| 0006 | H | H | H | —CH(CH$_3$)—O—CH$_3$ | H | H |
| 0007 | H | H | H | —C(CH$_3$)$_2$—O—CH$_3$ | H | H |
| 0008 | H | H | H | —CH(CH$_3$)—O—CO—CH$_3$ | H | H |
| 0009 | H | H | H | —CH$_2$—O—CO—CH$_3$ | H | H |
| 0010 | H | H | H | —C(CH$_3$)$_2$—O—CO—CH$_3$ | H | H |
| 0011 | H | H | H | —CH$_2$—CH$_2$—O—H | H | H |
| 0012 | H | H | H | —CH$_2$—CH$_2$—O—CH$_3$ | H | H |
| 0013 | H | H | H | —CH$_2$-(oxiranyl) | H | H |
| 0014 | H | H | H | -(oxiranyl)-CH$_3$ | H | H |
| 0015 | H | H | H | -(2,2-dimethyloxiranyl) | H | H |

TABLE A-continued

| Comp-No. | R₁ | R₂ | R₃ | R₄ | R₅ | R₆ |
|---|---|---|---|---|---|---|
| 0016 | H | H | H | 1,3-dioxolan-2-yl | H | H |
| 0017 | H | H | H | oxazol-2-yl | H | H |
| 0018 | H | H | H | furan-2-yl | H | H |
| 0019 | H | H | H | thiophen-2-yl | H | H |
| 0020 | H | H | H | 4-methylpiperazin-1-yl | H | H |
| 0021 | H | H | H | morpholin-4-yl | H | H |
| 0022 | H | H | H | 2,6-dimethylmorpholin-4-yl | H | H |
| 0023 | H | H | H | piperidin-1-yl | H | H |
| 0024 | H | H | H | pyrrolidin-1-yl | H | H |
| 0025 | H | H | H | H | H | H |
| 0026 | H | H | H | CN | H | H |
| 0027 | H | H | H | —C(CH₃)₂—OH | H | H |
| 0028 | H | H | H | —CH₂—OH | H | H |
| 0029 | H | H | H | —CO—CH₃ | H | H |
| 0030 | H | H | H | —C(=NOH)—CH₃ | H | H |
| 0031 | H | H | H | —CH(OH)—CH₃ | H | H |
| 0032 | H | H | H | (3) —CO—O—CH₂— (4) | | H |
| 0033 | H | H | H | —CH₂—CN | H | H |
| 0034 | H | H | H | —C(=NO—CH₃)—CH₃ | H | H |
| 0035 | H | H | H | —CO—O—CH₃ | H | H |
| 0036 | H | H | H | —NH—CO—C₃H₅-cycl. | H | H |
| 0037 | H | H | H | —CO—CH₃ | Cl | H |
| 0038 | H | H | H | —OH | H | H |
| 0039 | H | H | H | —OH | —OCH₃ | H |
| 0040 | H | H | H | —OCH₃ | H | —OCH₃ |
| 0041 | H | H | H | —SCH₃ | H | H |
| 0042 | H | H | H | —OCH₃ | H | H |
| 0043 | H | H | H | —OCH₃ | —OCH₃ | —OCH₃ |
| 0044 | H | H | H | —OH | —OCH₃ | —OCH₃ |
| 0045 | H | H | H | H | —SCH₃ | H |
| 0046 | H | H | —OCH₃ | H | —OCH₃ | H |
| 0047 | H | H | H | —OCH₃ | —OH | H |
| 0048 | H | H | —OCH₃ | H | H | H |
| 0049 | H | H | H | —CH₂—CH₃ | H | H |
| 0050 | H | H | —OCH₃ | —CH(CH₃)₂ | H | H |
| 0051 | H | H | H | —C₃H₇-n | H | H |

TABLE A-continued

| Comp-No. | $R_1$ | $R_2$ | $R_3$ | $R_4$ | $R_5$ | $R_6$ |
|---|---|---|---|---|---|---|
| 0052 | H | H | H | —OCH$_2$—CH$_3$ | H | H |
| 0053 | H | H | H | Cl | H | H |
| 0054 | H | H | H | Br | H | H |
| 0055 | H | H | H | Cl | Cl | H |
| 0056 | H | H | H | OH | OH | OH |
| 0057 | H | H | Cl | Cl | H | Cl |
| 0058 | H | H | H | —CF$_3$ | H | H |
| 0059 | H | H | H | —OCF$_3$ | H | H |
| 0060 | H | H | H | —C$_2$F$_5$ | H | H |
| 0061 | H | H | H | —C$_4$H$_9$-tert | H | H |
| 0062 | H | H | H | —OC$_3$H$_7$-i | H | H |
| 0063 | H | H | H | CH$_3$ | H | H |
| 0064 | H | H | H | —SO$_2$—CH$_3$ | H | H |
| 0065 | H | H | H | —NH—CH$_2$—CH$_3$ | H | H |
| 0066 | H | H | H | —O—CH$_2$—CH=CH$_2$ | H | H |
| 0067 | H | H | H | —O—CH$_2$—C≡CH | H | H |
| 0068 | H | H | H | —NH—CH$_2$—CH$_2$—NH—CH$_3$ | H | H |
| 0069 | H | H | H | —SO$_2$—C$_2$H$_5$ | H | H |
| 0070 | H | H | H | —SO$_2$—CH$_3$ | Cl | H |
| 0071 | C$_2$H$_5$ | H | H | —CH$_2$—O—CH$_3$ | H | H |
| 0072 | C$_2$H$_5$ | H | H | —NH—CO—CH$_3$ | H | H |
| 0073 | C$_2$H$_5$ | H | H | —CH$_2$—NH—CO—CH$_3$ | H | H |
| 0074 | C$_2$H$_5$ | H | H | —CH(CH$_3$)—NH—CO—CH$_3$ | H | H |
| 0075 | C$_2$H$_5$ | H | H | —C(CH$_3$)$_2$—NH—CO—CH$_3$ | H | H |
| 0076 | C$_2$H$_5$ | H | H | —CH(CH$_3$)—O—CH$_3$ | H | H |
| 0077 | C$_2$H$_5$ | H | H | —C(CH$_3$)$_2$—O—CH$_3$ | H | H |
| 0078 | C$_2$H$_5$ | H | H | —CH(CH$_3$)—O—CO—CH$_3$ | H | H |
| 0079 | C$_2$H$_5$ | H | H | —CH$_2$—O—CO—CH$_3$ | H | H |
| 0080 | C$_2$H$_5$ | H | H | —C(CH$_3$)$_2$—O—CO—CH$_3$ | H | H |
| 0081 | C$_2$H$_5$ | H | H | —CH$_2$—CH$_2$—O—H | H | H |
| 0082 | C$_2$H$_5$ | H | H | —CH$_2$—CH$_2$—O—CH$_3$ | H | H |
| 0083 | C$_2$H$_5$ | H | H | 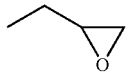 | H | H |
| 0084 | C$_2$H$_5$ | H | H |  | H | H |
| 0085 | C$_2$H$_5$ | H | H |  | H | H |
| 0086 | C$_2$H$_5$ | H | H | 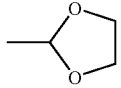 | H | H |
| 0087 | C$_2$H$_5$ | H | H | 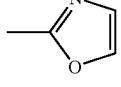 | H | H |
| 0088 | C$_2$H$_5$ | H | H | 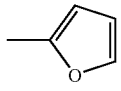 | H | H |
| 0089 | C$_2$H$_5$ | H | H | 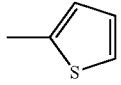 | H | H |
| 0090 | C$_2$H$_5$ | H | H | 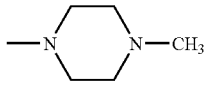 | H | H |
| 0091 | C$_2$H$_5$ | H | H | 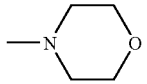 | H | H |

TABLE A-continued

| Comp-No. | $R_1$ | $R_2$ | $R_3$ | $R_4$ | $R_5$ | $R_6$ |
|---|---|---|---|---|---|---|
| 0092 | $C_2H_5$ | H | H | 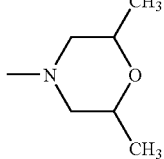 | H | H |
| 0093 | $C_2H_5$ | H | H | 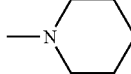 | H | H |
| 0094 | $C_2H_5$ | H | H | 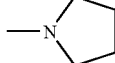 | H | H |
| 0095 | $C_2H_5$ | H | H | H | H | H |
| 0096 | $C_2H_5$ | H | H | CN | H | H |
| 0097 | $C_2H_5$ | H | H | —C(CH$_3$)$_2$—OH | H | H |
| 0098 | $C_2H_5$ | H | H | —CH$_2$—OH | H | H |
| 0099 | $C_2H_5$ | H | H | —CO—CH$_3$ | H | H |
| 0100 | $C_2H_5$ | H | H | —C(=NOH)—CH$_3$ | H | H |
| 0101 | $C_2H_5$ | H | H | —CH(OH)—CH$_3$ | H | H |
| 0102 | $C_2H_5$ | H | H | (3) —CO—O—CH$_2$— (4) | | H |
| 0103 | $C_2H_5$ | H | H | —CH$_2$—O—CO—CH$_3$ | H | H |
| 0104 | $C_2H_5$ | H | H | —C(=NO—CH$_3$)—CH$_3$ | H | H |
| 0105 | $C_2H_5$ | H | H | —CO—O—CH$_3$ | H | H |
| 0106 | $C_2H_5$ | H | H | —NH—CO—C$_3$H$_5$-cycl. | H | H |
| 0107 | $C_2H_5$ | H | H | —CO—CH$_3$ | Cl | H |
| 0108 | $C_2H_5$ | H | H | —OH | H | H |
| 0109 | $C_2H_5$ | H | H | —OH | —OCH$_3$ | H |
| 0110 | $C_2H_5$ | H | H | —OCH$_3$ | H | —OCH$_3$ |
| 0111 | $C_2H_5$ | H | H | —SCH$_3$ | H | H |
| 0112 | $C_2H_5$ | H | H | —OCH$_3$ | H | H |
| 0113 | $C_2H_5$ | H | H | —OCH$_3$ | —OCH$_3$ | —OCH$_3$ |
| 0114 | $C_2H_5$ | H | H | —OH | —OCH$_3$ | —OCH$_3$ |
| 0115 | $C_2H_5$ | H | H | H | —SCH$_3$ | H |
| 0116 | $C_2H_5$ | H | H | H | —OCH$_3$ | H |
| 0117 | $C_2H_5$ | H | H | —OCH$_3$ | —OH | H |
| 0118 | $C_2H_5$ | H | —OCH$_3$ | —CH$_3$ | H | H |
| 0119 | $C_2H_5$ | H | H | —CH$_2$—CH$_3$ | H | H |
| 0120 | $C_2H_5$ | H | —OCH$_3$ | —CH(CH$_3$)$_2$ | H | H |
| 0121 | $C_2H_5$ | H | H | —C$_3$H$_7$-n | H | H |
| 0122 | $C_2H_5$ | H | H | —OCH$_2$—CH$_3$ | H | H |
| 0123 | $C_2H_5$ | H | H | F | H | H |
| 0124 | $C_2H_5$ | H | H | Cl | H | H |
| 0125 | $C_2H_5$ | H | H | Br | H | H |
| 0126 | $C_2H_5$ | H | H | Cl | Cl | H |
| 0127 | $C_2H_5$ | H | H | OH | OH | OH |
| 0128 | $C_2H_5$ | H | Cl | Cl | H | Cl |
| 0129 | $C_2H_5$ | H | H | —CF$_3$ | H | H |
| 0130 | $C_2H_5$ | H | H | —OCF$_3$ | H | H |
| 0131 | $C_2H_5$ | H | H | —C$_2$F$_5$ | H | H |
| 0132 | $C_2H_5$ | H | H | —C$_4$H$_9$-tert | H | H |
| 0133 | $C_2H_5$ | H | H | —OC$_3$H$_7$-i | H | H |
| 0134 | $C_2H_5$ | H | H | —SO—C$_3$ | H | H |
| 0135 | $C_2H_5$ | H | H | —SO$_2$—CH$_3$ | H | H |
| 0136 | $C_2H_5$ | H | H | —NH—CH$_2$—CH$_3$ | H | H |
| 0137 | $C_2H_5$ | H | H | —O—CH$_2$—CH=CH$_2$ | H | H |
| 0138 | $C_2H_5$ | H | H | —O—CH$_2$—C≡CH | H | H |
| 0139 | $C_2H_5$ | H | H | —NH—CH$_2$—CH$_2$—NH—CH$_3$ | H | H |
| 0140 | $C_2H_5$ | H | H | —SO$_2$—C$_2$H$_5$ | H | H |
| 0141 | $C_2H_5$ | H | H | —SO$_2$—CH$_3$ | Cl | H |
| 0142 | $CH_3$ | H | H | —CH$_2$—O—CH$_3$ | H | H |
| 0143 | $CH_3$ | H | H | —NH—CO—CH$_3$ | H | H |
| 0144 | $CH_3$ | H | H | —CH$_2$—NH—CO—CH$_3$ | H | H |
| 0145 | $CH_3$ | H | H | —CH(CH$_3$)—NH—CO—CH$_3$ | H | H |
| 0146 | $CH_3$ | H | H | —C(CH$_3$)$_2$—NH—CO—CH$_3$ | H | H |
| 0147 | $CH_3$ | H | H | —CH(CH$_3$)—O—CH$_3$ | H | H |
| 0148 | $CH_3$ | H | H | —C(CH$_3$)$_2$—O—CH$_3$ | H | H |
| 0149 | $CH_3$ | H | H | —CH(CH$_3$)—O—CO—CH$_3$ | H | H |
| 0150 | $CH_3$ | H | H | —CH$_2$—O—CO—CH$_3$ | H | H |
| 0151 | $CH_3$ | H | H | —C(CH$_3$)$_2$—O—CO—CH$_3$ | H | H |

TABLE A-continued
| Comp-No. | R₁ | R₂ | R₃ | R₄ | R₅ | R₆ |
|---|---|---|---|---|---|---|
| 0152 | CH₃ | H | H | —CH₂—CH₂—O—H | H | H |
| 0153 | CH₃ | H | H | 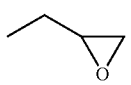 | H | H |
| 0154 | CH₃ | H | H |  | H | H |
| 0155 | CH₃ | H | H |  | H | H |
| 0156 | CH₃ | H | H | 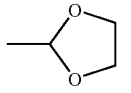 | H | H |
| 0157 | CH₃ | H | H | 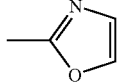 | H | H |
| 0158 | CH₃ | H | H | 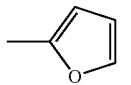 | H | H |
| 0159 | CH₃ | H | H | 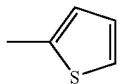 | H | H |
| 0160 | CH₃ | H | H | 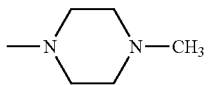 | H | H |
| 0161 | CH₃ | H | H | 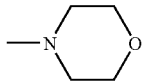 | H | H |
| 0162 | CH₃ | H | H | 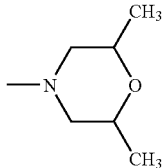 | H | H |
| 0163 | CH₃ | H | H | 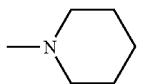 | H | H |
| 0164 | CH₃ | H | H | 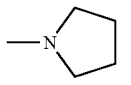 | H | H |
| 0165 | CH₃ | H | H | H | H | H |
| 0166 | CH₃ | H | H | CN | H | H |
| 0167 | CH₃ | H | H | —C(CH₃)₂—OH | H | H |
| 0168 | CH₃ | H | H | —CH₂—OH | H | H |
| 0169 | CH₃ | H | H | —CO—CH₃ | H | H |
| 0170 | CH₃ | H | H | —C(=NOH)—CH₃ | H | H |
| 0171 | CH₃ | H | H | —CH(OH)—CH₃ | H | H |
| 0172 | CH₃ | H | H | (3) —CO—O—CH₂— (4) | H | H |
| 0173 | CH₃ | H | H | —CH₂—O—CO—CH₃ | H | H |
| 0174 | CH₃ | H | H | —C(=NO—CH₃)—CH₃ | H | H |
| 0175 | CH₃ | H | H | —CO—O—CH₃ | H | H |
| 0176 | CH₃ | H | H | —NH—CO—C₃H₅-cycl. | H | H |

TABLE A-continued

| Comp-No. | R₁ | R₂ | R₃ | R₄ | R₅ | R₆ |
|---|---|---|---|---|---|---|
| 0177 | CH₃ | H | H | —CO—CH₃ | Cl | H |
| 0178 | CH₃ | H | H | —OH | H | H |
| 0179 | CH₃ | H | H | —OH | —OCH₃ | H |
| 0180 | CH₃ | H | H | —OCH₃ | H | —OCH₃ |
| 0181 | CH₃ | H | H | —SCH₃ | H | H |
| 0182 | CH₃ | H | H | —OCH₃ | H | H |
| 0183 | CH₃ | H | H | —OCH₃ | —OCH₃ | —OCH₃ |
| 0184 | CH₃ | H | H | —OH | —OCH₃ | —OCH₃ |
| 0185 | CH₃ | H | H | H | —SCH₃ | H |
| 0186 | CH₃ | H | H | H | —OCH₃ | H |
| 0187 | CH₃ | H | H | —OCH₃ | —OH | H |
| 0188 | CH₃ | H | —OCH₃ | —CH₃ | H | H |
| 0189 | CH₃ | H | H | —CH₂—CH₃ | H | H |
| 0190 | CH₃ | H | —OCH₃ | —CH(CH₃)₂ | H | H |
| 0191 | CH₃ | H | H | —C₃H₇-n | H | H |
| 0192 | CH₃ | H | H | —OCH₂—CH₃ | H | H |
| 0193 | CH₃ | H | H | F | H | H |
| 0194 | CH₃ | H | H | Cl | H | H |
| 0195 | CH₃ | H | H | Br | H | H |
| 0196 | CH₃ | H | H | Cl | Cl | H |
| 0197 | CH₃ | H | H | OH | OH | OH |
| 0198 | CH₃ | H | Cl | Cl | H | Cl |
| 0199 | CH₃ | H | H | —CF₃ | H | H |
| 0200 | H | H | H | —OCH₂—CF₃ | H | H |
| 0201 | CH₃ | H | H | —C₂F₅ | H | H |
| 0202 | CH₃ | H | H | —C₄H₉-tert | H | H |
| 0203 | CH₃ | H | H | —OC₃H₇-i | H | H |
| 0204 | CH₃ | H | H | —SO—CH₃ | H | H |
| 0205 | CH₃ | H | H | —SO₂—CH₃ | H | H |
| 0206 | CH₃ | H | H | —NH—CH₂—CH₃ | H | H |
| 0207 | CH₃ | H | H | —O—CH₂—CH=CH₂ | H | H |
| 0208 | CH₃ | H | H | —O—CH₂—C≡CH | H | H |
| 0209 | CH₃ | H | H | —NH—CH₂—CH₂—NH—CH₃ | H | H |
| 0210 | CH₃ | H | H | —SO₂—C₂H₅ | H | H |
| 0211 | CH₃ | H | H | —SO₂—CH₃ | Cl | H |
| 0212 | CH₃ | CH₃ | H | —CH₂—O—CH₃ | H | H |
| 0213 | CH₃ | CH₃ | H | —NH—CO—CH₃ | H | H |
| 0214 | CH₃ | CH₃ | H | —CH₂—NH—CO—CH₃ | H | H |
| 0215 | CH₃ | CH₃ | H | —CH(CH₃)—NH—CO—CH₃ | H | H |
| 0216 | CH₃ | CH₃ | H | —C(CH₃)₂—NH—CO—CH₃ | H | H |
| 0217 | CH₃ | CH₃ | H | —CH(CH₃)—O—CH₃ | H | H |
| 0218 | CH₃ | CH₃ | H | —C(CH₃)₂—O—CH₃ | H | H |
| 0219 | CH₃ | CH₃ | H | —CH(CH₃)—O—CO—CH₃ | H | H |
| 0220 | CH₃ | CH₃ | H | —CH₂—O—CO—CH₃ | H | H |
| 0221 | CH₃ | CH₃ | H | —C(CH₃)₂—O—CO—CH₃ | H | H |
| 0222 | CH₃ | CH₃ | H | —CH₂—CH₂—O—H | H | H |
| 0223 | CH₃ | CH₃ | H | —CH₂—CH₂—O—CH₃ | H | H |
| 0224 | CH₃ | CH₃ | H | ![epoxide -CH2-CH(-O-)CH2 ring] | H | H |
| 0225 | CH₃ | CH₃ | H | ![epoxide -CH(-O-)CH2 ring] | H | H |
| 0226 | CH₃ | CH₃ | H | ![2-methyloxirane] | H | H |
| 0227 | CH₃ | CH₃ | H | ![1,3-dioxolan-2-yl] | H | H |
| 0228 | CH₃ | CH₃ | H | ![oxazole] | H | H |
| 0229 | CH₃ | CH₃ | H | ![furan] | H | H |

TABLE A-continued

| Comp-No. | R₁ | R₂ | R₃ | R₄ | R₅ | R₆ |
|---|---|---|---|---|---|---|
| 0230 | CH₃ | CH₃ | H | 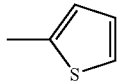 | H | H |
| 0231 | CH₃ | CH₃ | H | 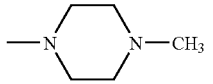 | H | H |
| 0232 | CH₃ | CH₃ | H |  | H | H |
| 0233 | CH₃ | CH₃ | H | 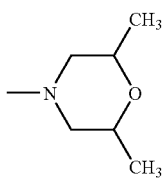 | H | H |
| 0234 | CH₃ | CH₃ | H | 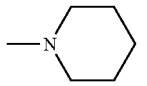 | H | H |
| 0235 | CH₃ | CH₃ | H | 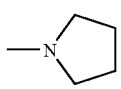 | H | H |
| 0236 | CH₃ | CH₃ | H | H | H | H |
| 0237 | CH₃ | CH₃ | H | CN | H | H |
| 0238 | CH₃ | CH₃ | H | —C(CH₃)₂—OH | H | H |
| 0239 | CH₃ | CH₃ | H | —CH₂—OH | H | H |
| 0240 | CH₃ | CH₃ | H | —CO—CH₃ | H | H |
| 0241 | CH₃ | CH₃ | H | —C(═NOH)—CH₃ | H | H |
| 0242 | CH₃ | CH₃ | H | —CH(OH)—CH₃ | H | H |
| 0243 | CH₃ | CH₃ | H | (3) —CO—O—CH₂— (4) | | H |
| 0244 | CH₃ | CH₃ | H | —CH₂—O—CO—CH₃ | H | H |
| 0245 | CH₃ | CH₃ | H | —C(═NO—CH₃)—CH₃ | H | H |
| 0246 | CH₃ | CH₃ | H | —CO—O—CH₃ | H | H |
| 0247 | CH₃ | CH₃ | H | —NH—CO—C₃H₅-cycl. | H | H |
| 0248 | CH₃ | CH₃ | H | —NH—CO—C₆H₁₁-cycl. | H | H |
| 0249 | CH₃ | CH₃ | H | —CO—CH₃ | Cl | H |
| 0250 | CH₃ | CH₃ | H | —OH | H | H |
| 0251 | CH₃ | CH₃ | H | —OH | —OCH₃ | H |
| 0252 | CH₃ | CH₃ | H | —OCH₃ | H | —OCH₃ |
| 0253 | CH₃ | CH₃ | H | —OCH₃ | H | H |
| 0254 | CH₃ | CH₃ | H | —OCH₃ | —OCH₃ | —OCH₃ |
| 0255 | CH₃ | CH₃ | H | —OH | —OCH₃ | —OCH₃ |
| 0256 | CH₃ | CH₃ | H | H | —SCH₃ | H |
| 0257 | CH₃ | CH₃ | H | H | —OCH₃ | H |
| 0258 | CH₃ | CH₃ | H | —OCH₃ | —OH | H |
| 0259 | CH₃ | CH₃ | —OCH₃ | —CH₃ | H | H |
| 0260 | CH₃ | CH₃ | H | —CH₂—CH₃ | H | H |
| 0261 | CH₃ | CH₃ | —OCH₃ | —CH(CH₃)₂ | H | H |
| 0262 | CH₃ | CH₃ | H | —C₃H₇-n | H | H |
| 0263 | CH₃ | CH₃ | H | —OCH₂—CH₃ | H | H |
| 0264 | CH₃ | CH₃ | H | F | H | H |
| 0265 | CH₃ | CH₃ | H | Cl | H | H |
| 0266 | CH₃ | CH₃ | H | Br | H | H |
| 0267 | CH₃ | CH₃ | H | Cl | Cl | H |
| 0268 | CH₃ | CH₃ | H | OH | OH | OH |
| 0269 | CH₃ | CH₃ | Cl | Cl | H | Cl |
| 0270 | CH₃ | CH₃ | H | —CF₃ | H | H |
| 0271 | CH₃ | CH₃ | H | —OCF₃ | H | H |
| 0272 | CH₃ | CH₃ | H | —C₂F₅ | H | H |
| 0273 | CH₃ | CH₃ | H | —C₄H₉-tert | H | H |
| 0274 | CH₃ | CH₃ | H | —OC₃H₇-i | H | H |
| 0275 | CH₃ | CH₃ | H | —SO—CH₃ | H | H |
| 0276 | CH₃ | CH₃ | H | —SO₂—CH₃ | H | H |

TABLE A-continued

| Comp-No. | $R_1$ | $R_2$ | $R_3$ | $R_4$ | $R_5$ | $R_6$ |
|---|---|---|---|---|---|---|
| 0277 | $CH_3$ | $CH_3$ | H | $-NH-CH_2-CH_3$ | H | H |
| 0278 | $CH_3$ | $CH_3$ | H | $-O-CH_2-CH=CH_2$ | H | H |
| 0279 | $CH_3$ | $CH_3$ | H | $-O-CH_2-C\equiv CH$ | H | H |
| 0280 | $CH_3$ | $CH_3$ | H | $-NH-CH_2-CH_2-NH-CH_3$ | H | H |
| 0281 | $CH_3$ | $CH_3$ | H | $-SO_2-C_2H_5$ | H | H |
| 0282 | $CH_3$ | $CH_3$ | H | $-SO_2-CH_3$ | Cl | H |
| 0283 | $-CO-CH_3$ | H | H | $-CH_2-O-CH_3$ | H | H |
| 0284 | $-CO-CH_3$ | H | H | $-NH-CO-CH_3$ | H | H |
| 0285 | $-CO-CH_3$ | H | H | $-CH_2-NH-CO-CH_3$ | H | H |
| 0286 | $-CO-CH_3$ | H | H | $-CH(CH_3)-NH-CO-CH_3$ | H | H |
| 0287 | $-CO-CH_3$ | H | H | $-C(CH_3)_2-NH-CO-CH_3$ | H | H |
| 0288 | $-CO-CH_3$ | H | H | $-CH(CH_3)-O-CH_3$ | H | H |
| 0289 | $-CO-CH_3$ | H | H | $-C(CH_3)_2-O-CH_3$ | H | H |
| 0290 | $-CO-CH_3$ | H | H | $-CH(CH_3)-O-CO-CH_3$ | H | H |
| 0291 | $-CO-CH_3$ | H | H | $-CH_2-O-CO-CH_3$ | H | H |
| 0292 | $-CO-CH_3$ | H | H | $-C(CH_3)_2-O-CO-CH_3$ | H | H |
| 0293 | $-CO-CH_3$ | H | H | $-CH_2-CH_2-O-H$ | H | H |
| 0294 | $-CO-CH_3$ | H | H | $-CH_2-CH_2-O-CH_3$ | H | H |
| 0295 | $-CO-CH_3$ | H | H | 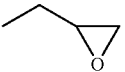 | H | H |
| 0296 | $-CO-CH_3$ | H | H |  | H | H |
| 0297 | $-CO-CH_3$ | H | H |  | H | H |
| 0298 | $-CO-CH_3$ | H | H | 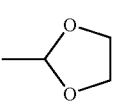 | H | H |
| 0299 | $-CO-CH_3$ | H | H | 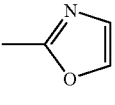 | H | H |
| 0300 | $-CO-CH_3$ | H | H | 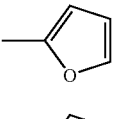 | H | H |
| 0301 | $-CO-CH_3$ | H | H | 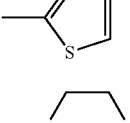 | H | H |
| 0302 | $-CO-CH_3$ | H | H | 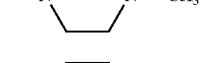 | H | H |
| 0303 | $-CO-CH_3$ | H | H | 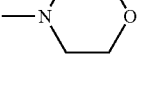 | H | H |
| 0304 | $-CO-CH_3$ | H | H | 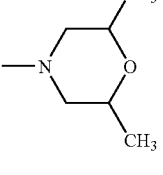 | H | H |
| 0305 | $-CO-CH_3$ | H | H | 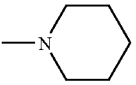 | H | H |

TABLE A-continued

| Comp-No. | R$_1$ | R$_2$ | R$_3$ | R$_4$ | R$_5$ | R$_6$ |
|---|---|---|---|---|---|---|
| 0306 | —CO—CH$_3$ | H | H | (N-pyrrolidinyl) | H | H |
| 0307 | —CO—CH$_3$ | H | H | H | H | H |
| 0308 | —CO—CH$_3$ | H | H | CN | H | H |
| 0309 | —CO—CH$_3$ | H | H | —C(CH$_3$)$_2$—OH | H | H |
| 0310 | —CO—CH$_3$ | H | H | —CH$_2$—OH | H | H |
| 0311 | —CO—CH$_3$ | H | H | —CO—CH$_3$ | H | H |
| 0312 | —CO—CH$_3$ | H | H | —C(=NOH)—CH$_3$ | H | H |
| 0313 | —CO—CH$_3$ | H | H | —CH(OH)—CH$_3$ | H | H |
| 0314 | —CO—CH$_3$ | H | H | (3) —CO—O—CH$_2$— (4) | | H |
| 0315 | —CO—CH$_3$ | H | H | —CH$_2$—O—CO—CH$_3$ | H | H |
| 0316 | —CO—CH$_3$ | H | H | —C(=NO—CH$_3$)—CH$_3$ | H | H |
| 0317 | —CO—CH$_3$ | H | H | —CO—O—CH$_3$ | H | H |
| 0318 | —CO—CH$_3$ | H | H | —NH—CO—C$_3$H$_5$-cycl. | H | H |
| 0319 | —CO—CH$_3$ | H | H | —CO—CH$_3$ | Cl | H |
| 0320 | —CO—CH$_3$ | H | H | —OH | H | H |
| 0321 | —CO—CH$_3$ | H | H | —OH | —OCH$_3$ | H |
| 0322 | —CO—CH$_3$ | H | H | —OCH$_3$ | H | —OCH$_3$ |
| 0323 | —CO—CH$_3$ | H | H | —SCH$_3$ | H | H |
| 0324 | —CO—CH$_3$ | H | H | —OCH$_3$ | H | H |
| 0325 | —CO—CH$_3$ | H | H | —OCH$_3$ | —OCH$_3$ | —OCH$_3$ |
| 0326 | —CO—CH$_3$ | H | H | —OH | —OCH$_3$ | —OCH$_3$ |
| 0327 | —CO—CH$_3$ | H | H | H | —SCH$_3$ | H |
| 0328 | —CO—CH$_3$ | H | H | H | —OCH$_3$ | H |
| 0329 | —CO—CH$_3$ | H | H | —OCH$_3$ | —OH | H |
| 0330 | —CO—CH$_3$ | H | —OCH$_3$ | —CH$_3$ | H | H |
| 0331 | —CO—CH$_3$ | H | H | —CH$_2$—CH$_3$ | H | H |
| 0332 | —CO—CH$_3$ | H | —OCH$_3$ | —CH(CH$_3$)$_2$ | H | H |
| 0333 | —CO—CH$_3$ | H | H | —C$_3$H$_7$-n | H | H |
| 0334 | —CO—CH$_3$ | H | H | —OCH$_2$—CH$_3$ | H | H |
| 0335 | —CO—CH$_3$ | H | H | F | H | H |
| 0336 | —CO—CH$_3$ | H | H | Cl | H | H |
| 0337 | —CO—CH$_3$ | H | H | Br | H | H |
| 0338 | —CO—CH$_3$ | H | H | Cl | Cl | H |
| 0339 | —CO—CH$_3$ | H | H | OH | OH | OH |
| 0340 | —CO—CH$_3$ | H | Cl | Cl | H | Cl |
| 0341 | —CO—CH$_3$ | H | H | —CF$_3$ | H | H |
| 0342 | —CO—CH$_3$ | H | H | —OCF$_3$ | H | H |
| 0343 | —CO—CH$_3$ | H | H | —C$_2$F$_5$ | H | H |
| 0344 | —CO—CH$_3$ | H | H | —C$_4$H$_9$-tert | H | H |
| 0345 | —CO—CH$_3$ | H | H | —OC$_3$H$_7$-i | H | H |
| 0346 | —CO—CH$_3$ | H | H | —SO—CH$_3$ | H | H |
| 0347 | —CO—CH$_3$ | H | H | —SO$_2$—CH$_3$ | H | H |
| 0348 | —CO—CH$_3$ | H | H | —NH—CH$_2$—CH$_3$ | H | H |
| 0349 | —CO—CH$_3$ | H | H | —O—CH$_2$—CH=CH$_2$ | H | H |
| 0350 | —CO—CH$_3$ | H | H | —O—CH$_2$—C≡CH | H | H |
| 0351 | —CO—CH$_3$ | H | H | —NH—CH$_2$—CH$_2$—NH—CH$_3$ | H | H |
| 0352 | —CO—CH$_3$ | H | H | —SO$_2$—C$_2$H$_5$ | H | H |
| 0353 | —CO—C$_2$H$_5$ | H | H | —CH$_2$—O—CH$_3$ | H | H |
| 0354 | —CO—C$_2$H$_5$ | H | H | —NH—CO—CH$_3$ | H | H |
| 0355 | —CO—C$_2$H$_5$ | H | H | —CH$_2$—NH—CO—CH$_3$ | H | H |
| 0356 | —CO—C$_2$H$_5$ | H | H | —CH(CH$_3$)—NH—CO—CH$_3$ | H | H |
| 0357 | —CO—C$_2$H$_5$ | H | H | —C(CH$_3$)$_2$—NH—CO—CH$_3$ | H | H |
| 0358 | —CO—C$_2$H$_5$ | H | H | —CH(CH$_3$)—O—CH$_3$ | H | H |
| 0359 | —CO—C$_2$H$_5$ | H | H | —C(CH$_3$)$_2$—O—CH$_3$ | H | H |
| 0360 | —CO—C$_2$H$_5$ | H | H | —CH(CH$_3$)—O—CO—CH$_3$ | H | H |
| 0361 | —CO—C$_2$H$_5$ | H | H | —CH$_2$—O—CO—CH$_3$ | H | H |
| 0362 | —CO—C$_2$H$_5$ | H | H | —C(CH$_3$)$_2$—O—CO—CH$_3$ | H | H |
| 0363 | —CO—C$_2$H$_5$ | H | H | —CH$_2$—CH$_2$—O—H | H | H |
| 0364 | —CO—C$_2$H$_5$ | H | H | —CH$_2$—CH$_2$—O—CH$_3$ | H | H |
| 0365 | —CO—C$_2$H$_5$ | H | H | (oxiranyl) | H | H |
| 0366 | —CO—C$_2$H$_5$ | H | H | (oxiranyl) | H | H |

TABLE A-continued

| Comp-No. | R₁ | R₂ | R₃ | R₄ | R₅ | R₆ |
|---|---|---|---|---|---|---|
| 0367 | —CO—C₂H₅ | H | H | 2-methyloxiranyl | H | H |
| 0368 | —CO—C₂H₅ | H | H | 2-methyl-1,3-dioxolanyl | H | H |
| 0369 | —CO—C₂H₅ | H | H | 2-methyloxazolyl | H | H |
| 0370 | —CO—C₂H₅ | H | H | 2-methylfuranyl | H | H |
| 0371 | —CO—C₂H₅ | H | H | 2-methylthienyl | H | H |
| 0372 | —CO—C₂H₅ | H | H | 4-methylpiperazin-1-yl | H | H |
| 0373 | —CO—C₂H₅ | H | H | morpholin-4-yl | H | H |
| 0374 | —CO—C₂H₅ | H | H | 2,6-dimethylmorpholin-4-yl | H | H |
| 0375 | —CO—C₂H₅ | H | H | piperidin-1-yl | H | H |
| 0376 | —CO—C₂H₅ | H | H | pyrrolidin-1-yl | H | H |
| 0377 | —CO—C₂H₅ | H | H | H | H | H |
| 0378 | —CO—C₂H₅ | H | H | CN | H | H |
| 0379 | —CO—C₂H₅ | H | H | —C(CH₃)₂—OH | H | H |
| 0380 | —CO—C₂H₅ | H | H | —CH₂—OH | H | H |
| 0381 | —CO—C₂H₅ | H | H | —CO—CH₃ | H | H |
| 0382 | —CO—C₂H₅ | H | H | —C(=NOH)—CH₃ | H | H |
| 0383 | —CO—C₂H₅ | H | H | —CH(OH)—CH₃ | H | H |
| 0384 | —CO—C₂H₅ | H | H | (3) —CO—O—CH₂— (4) | | H |
| 0385 | —CO—C₂H₅ | H | H | —CH₂—O—CO—CH₃ | H | H |
| 0386 | —CO—C₂H₅ | H | H | —C(=NO—CH₃)—CH₃ | H | H |
| 0387 | —CO—C₂H₅ | H | H | —CO—O—CH₃ | H | H |
| 0388 | —CO—C₂H₅ | H | H | —NH—CO—C₃H₅-cycl. | H | H |
| 0389 | —CO—C₂H₅ | H | H | —CO—CH₃ | Cl | H |
| 0390 | —CO—C₂H₅ | H | H | —OH | H | H |
| 0391 | —CO—C₂H₅ | H | H | —OH | —OCH₃ | H |
| 0392 | —CO—C₂H₅ | H | H | —OCH₃ | H | —OCH₃ |
| 0393 | —CO—C₂H₅ | H | H | —SCH₃ | H | H |
| 0394 | —CO—C₂H₅ | H | H | —OCH₃ | H | H |
| 0395 | —CO—C₂H₅ | H | H | —OCH₃ | —OCH₃ | —OCH₃ |
| 0396 | —CO—C₂H₅ | H | H | —OH | —OCH₃ | —OCH₃ |
| 0397 | —CO—C₂H₅ | H | H | H | —SCH₃ | H |
| 0398 | —CO—C₂H₅ | H | H | H | —OCH₃ | H |

TABLE A-continued

| Comp-No. | R₁ | R₂ | R₃ | R₄ | R₅ | R₆ |
|---|---|---|---|---|---|---|
| 0399 | —CO—C₂H₅ | H | H | —OCH₃ | —OH | H |
| 0400 | —CO—C₂H₅ | H | —OCH₃ | —CH₃ | H | H |
| 0401 | —CO—C₂H₅ | H | H | —CH₂—CH₃ | H | H |
| 0402 | —CO—C₂H₅ | H | —OCH₃ | —CH(CH₃)₂ | H | H |
| 0403 | —CO—C₂H₅ | H | H | —C₃H₇-n | H | H |
| 0404 | —CO—C₂H₅ | H | H | —OCH₂—CH₃ | H | H |
| 0405 | —CO—C₂H₅ | H | H | F | H | H |
| 0406 | —CO—C₂H₅ | H | H | Cl | H | H |
| 0407 | —CO—C₂H₅ | H | H | Br | H | H |
| 0408 | —CO—C₂H₅ | H | H | Cl | Cl | H |
| 0409 | —CO—C₂H₅ | H | H | OH | OH | OH |
| 0410 | —CO—C₂H₅ | H | Cl | Cl | H | Cl |
| 0411 | —CO—C₂H₅ | H | H | —CF₃ | H | H |
| 0412 | —CO—C₂H₅ | H | H | —OCF₃ | H | H |
| 0413 | —CO—C₂H₅ | H | H | —C₂F₅ | H | H |
| 0414 | —CO—C₂H₅ | H | H | —C₄H₉-tert | H | H |
| 0415 | —CO—C₂H₅ | H | H | —OC₃H₇-i | H | H |
| 0416 | —CO—C₂H₅ | H | H | —SO—CH₃ | H | H |
| 0417 | —CO—C₂H₅ | H | H | —SO₂—CH₃ | H | H |
| 0418 | —CO—C₂H₅ | H | H | —NH—CH₂—CH₃ | H | H |
| 0419 | —CO—C₂H₅ | H | H | —O—CH₂—CH=CH₂ | H | H |
| 0420 | —CO—C₂H₅ | H | H | —O—CH₂—C≡CH | H | H |
| 0421 | —CO—C₂H₅ | H | H | —NH—CH₂—CH₂—NH—CH₃ | H | H |
| 0422 | —CO—C₂H₅ | H | H | —SO₂—C₂H₅ | H | H |
| 0423 | —CO—C₂H₅ | H | H | —SO₂—CH₃ | Cl | H |
| 0424 | —CO—CH(CH₃)—C₂H₅ | H | H | —CH₂—O—CH₃ | H | H |
| 0425 | —CO—CH(CH₃)—C₂H₅ | H | H | —NH—CO—CH₃ | H | H |
| 0426 | —CO—CH(CH₃)—C₂H₅ | H | H | —CH₂—NH—CO—CH₃ | H | H |
| 0427 | —CO—CH(CH₃)—C₂H₅ | H | H | —CH(CH₃)—NH—CO—CH₃ | H | H |
| 0428 | —CO—CH(CH₃)—C₂H₅ | H | H | —C(CH₃)₂—NH—CO—CH₃ | H | H |
| 0429 | —CO—CH(CH₃)—C₂H₅ | H | H | —CH(CH₃)—O—CH₃ | H | H |
| 0430 | —CO—CH(CH₃)—C₂H₅ | H | H | —C(CH₃)₂—O—CH₃ | H | H |
| 0431 | —CO—CH(CH₃)—C₂H₅ | H | H | —CH(CH₃)—O—CO—CH₃ | H | H |
| 0432 | —CO—CH(CH₃)—C₂H₅ | H | H | —CH₂—O—CO—CH₃ | H | H |
| 0433 | —CO—CH(CH₃)—C₂H₅ | H | H | —C(CH₃)₂—O—CO—CH₃ | H | H |
| 0434 | —CO—CH(CH₃)—C₂H₅ | H | H | —CH₂—CH₂—O—H | H | H |
| 0435 | —CO—CH(CH₃)—C₂H₅ | H | H | —CH₂—CH₂—O—CH₃ | H | H |
| 0436 | —CO—CH(CH₃)—C₂H₅ | H | H | ![epoxide-CH2-] (glycidyl) | H | H |
| 0437 | —CO—CH(CH₃)—C₂H₅ | H | H | (oxiranyl) | H | H |
| 0438 | —CO—CH(CH₃)—C₂H₅ | H | H | (2-methyloxiranyl) | H | H |
| 0439 | —CO—CH(CH₃)—C₂H₅ | H | H | (1,3-dioxolan-2-yl) | H | H |
| 0440 | —CO—CH(CH₃)—C₂H₅ | H | H | (oxazol-2-yl) | H | H |
| 0441 | —CO—CH(CH₃)—C₂H₅ | H | H | (furan-2-yl) | H | H |
| 0442 | —CO—CH(CH₃)—C₂H₅ | H | H | (thiophen-2-yl) | H | H |
| 0443 | —CO—CH(CH₃)—C₂H₅ | H | H | (4-methylpiperazin-1-yl) | H | H |

TABLE A-continued

| Comp-No. | R₁ | R₂ | R₃ | R₄ | R₅ | R₆ |
|---|---|---|---|---|---|---|
| 0444 | —CO—CH(CH₃)—C₂H₅ | H | H | N-morpholinyl | H | H |
| 0445 | —CO—CH(CH₃)—C₂H₅ | H | H | 2,6-dimethyl-N-morpholinyl | H | H |
| 0446 | —CO—CH(CH₃)—C₂H₅ | H | H | N-piperidinyl | H | H |
| 0447 | —CO—CH(CH₃)—C₂H₅ | H | H | N-pyrrolidinyl | H | H |
| 0448 | —CO—CH(CH₃)—C₂H₅ | H | H | H | H | H |
| 0449 | —CO—CH(CH₃)—C₂H₅ | H | H | CN | H | H |
| 0450 | —CO—CH(CH₃)—C₂H₅ | H | H | —C(CH₃)₂—OH | H | H |
| 0451 | —CO—CH(CH₃)—C₂H₅ | H | H | —CH₂—OH | H | H |
| 0452 | —CO—CH(CH₃)—C₂H₅ | H | H | —CO—CH₃ | H | H |
| 0453 | —CO—CH(CH₃)—C₂H₅ | H | H | —CH(OH)—CH₃ | H | H |
| 0454 | —CO—CH(CH₃)—C₂H₅ | H | H | (3) —CO—O—CH₂— (4) | | H |
| 0455 | —CO—CH(CH₃)—C₂H₅ | H | H | —CH₂—O—CO—CH₃ | H | H |
| 0456 | —CO—CH(CH₃)—C₂H₅ | H | H | —C(=NO—CH₃)—CH₃ | H | H |
| 0457 | —CO—CH(CH₃)—C₂H₅ | H | H | —CO—O—CH₃ | H | H |
| 0458 | —CO—CH(CH₃)—C₂H₅ | H | H | —NH—CO—C₃H₅-cycl. | H | H |
| 0459 | —CO—CH(CH₃)—C₂H₅ | H | H | —CO—CH₃ | Cl | H |
| 0460 | —CO—CH(CH₃)—C₂H₅ | H | H | —OH | H | H |
| 0461 | —CO—CH(CH₃)—C₂H₅ | H | H | —OH | —OCH₃ | H |
| 0462 | —CO—CH(CH₃)—C₂H₅ | H | H | —OCH₃ | H | —OCH₃ |
| 0463 | —CO—CH(CH₃)—C₂H₅ | H | H | —SCH₃ | H | H |
| 0464 | —CO—CH(CH₃)—C₂H₅ | H | H | —OCH₃ | H | H |
| 0465 | —CO—CH(CH₃)—C₂H₅ | H | H | —OCH₃ | —OCH₃ | —OCH₃ |
| 0466 | —CO—CH(CH₃)—C₂H₅ | H | H | —OH | —OCH₃ | —OCH₃ |
| 0467 | —CO—CH(CH₃)—C₂H₅ | H | H | H | —SCH₃ | H |
| 0468 | —CO—CH(CH₃)—C₂H₅ | H | H | H | —OCH₃ | H |
| 0469 | —CO—CH(CH₃)—C₂H₅ | H | H | —OCH₃ | —OH | H |
| 0470 | —CO—CH(CH₃)—C₂H₅ | H | —OCH₃ | —CH₃ | H | H |
| 0471 | —CO—CH(CH₃)—C₂H₅ | H | H | —CH₂—CH₃ | H | H |
| 0472 | —CO—CH(CH₃)—C₂H₅ | H | —OCH₃ | —CH(CH₃)₂ | H | H |
| 0473 | —CO—CH(CH₃)—C₂H₅ | H | H | —C₃H₇-n | H | H |
| 0474 | —CO—CH(CH₃)—C₂H₅ | H | H | —OCH₂—CH₃ | H | H |
| 0475 | —CO—CH(CH₃)—C₂H₅ | H | H | F | H | H |
| 0476 | —CO—CH(CH₃)—C₂H₅ | H | H | Cl | H | H |
| 0477 | —CO—CH(CH₃)—C₂H₅ | H | H | Br | H | H |
| 0478 | —CO—CH(CH₃)—C₂H₅ | H | H | Cl | Cl | H |
| 0479 | —CO—CH(CH₃)—C₂H₅ | H | H | OH | OH | OH |
| 0480 | —CO—CH(CH₃)—C₂H₅ | H | Cl | Cl | H | Cl |
| 0481 | —CO—CH(CH₃)—C₂H₅ | H | H | —CF₃ | H | H |
| 0482 | —CO—CH(CH₃)—C₂H₅ | H | H | —OCF₃ | H | H |
| 0483 | —CO—CH(CH₃)—C₂H₅ | H | H | —C₂F₅ | H | H |
| 0484 | —CO—CH(CH₃)—C₂H₅ | H | H | —C₄H₉-tert | H | H |
| 0485 | —CO—CH(CH₃)—C₂H₅ | H | H | —OC₃H₇-i | H | H |
| 0486 | —CO—CH(CH₃)—C₂H₅ | H | H | —SO—CH₃ | H | H |
| 0487 | —CO—CH(CH₃)—C₂H₅ | H | H | —SO₂—CH₃ | H | H |
| 0488 | —CO—CH(CH₃)—C₂H₅ | H | H | —NH—CH₂—CH₃ | H | H |
| 0489 | —CO—CH(CH₃)—C₂H₅ | H | H | —O—CH₂—CH=CH₂ | H | H |
| 0490 | —CO—CH(CH₃)—C₂H₅ | H | H | —O—CH₂—C≡CH | H | H |
| 0491 | —CO—CH(CH₃)—C₂H₅ | H | H | —NH—CH₂—CH₂—NH—CH₃ | H | H |
| 0492 | —CO—CH(CH₃)—C₂H₅ | H | H | —SO₂—C₂H₅ | H | H |
| 0493 | —CO—CH(CH₃)—C₂H₅ | H | H | —SO₂—CH₃ | Cl | H |
| 0494 | —CO—C₃F₇-n | H | H | —CH₂—O—CH₃ | H | H |
| 0495 | —CO—C₃F₇-n | H | H | —NH—CO—CH₃ | H | H |
| 0496 | —CO—C₃F₇-n | H | H | —CH₂—NH—CO—CH₃ | H | H |
| 0497 | —CO—C₃F₇-n | H | H | —CH(CH₃)—NH—CO—CH₃ | H | H |
| 0498 | —CO—C₃F₇-n | H | H | —C(CH₃)₂—NH—CO—CH₃ | H | H |

TABLE A-continued

| Comp-No. | R1 | R2 | R3 | R4 | R5 | R6 |
|---|---|---|---|---|---|---|
| 0499 | —CO—C3F7-n | H | H | —CH(CH3)—O—CH3 | H | H |
| 0500 | —CO—C3F7-n | H | H | —C(CH3)2—O—CH3 | H | H |
| 0501 | —CO—C3F7-n | H | H | —CH(CH3)—O—CO—CH3 | H | H |
| 0502 | —CO—C3F7-n | H | H | —CH2—O—CO—CH3 | H | H |
| 0503 | —CO—C3F7-n | H | H | —C(CH3)2—O—CO—CH3 | H | H |
| 0504 | —CO—C3F7-n | H | H | —CH2—CH2—O—H | H | H |
| 0505 | —CO—C3F7-n | H | H | —CH2—CH2—O—CH3 | H | H |
| 0506 | —CO—C3F7-n | H | H | 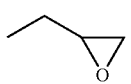 | H | H |
| 0507 | —CO—C3F7-n | H | H |  | H | H |
| 0508 | —CO—C3F7-n | H | H |  | H | H |
| 0509 | —CO—C3F7-n | H | H | 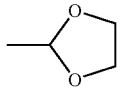 | H | H |
| 0510 | —CO—C3F7-n | H | H | 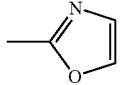 | H | H |
| 0511 | —CO—C3F7-n | H | H | 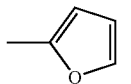 | H | H |
| 0512 | —CO—C3F7-n | H | H | 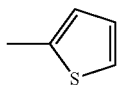 | H | H |
| 0513 | —CO—C3F7-n | H | H | 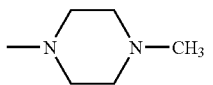 | H | H |
| 0514 | —CO—C3F7-n | H | H | 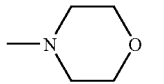 | H | H |
| 0515 | —CO—C3F7-n | H | H | 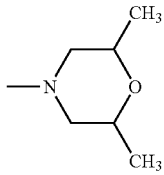 | H | H |
| 0516 | —CO—C3F7-n | H | H | 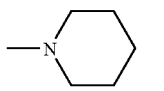 | H | H |
| 0517 | —CO—C3F7-n | H | H | 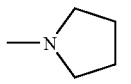 | H | H |
| 0518 | —CO—C3F7-n | H | H | H | H | H |
| 0519 | —CO—C3F7-n | H | H | CN | H | H |
| 0520 | —CO—C3F7-n | H | H | —C(CH3)2—OH | H | H |
| 0521 | —CO—C3F7-n | H | H | —CH2—OH | H | H |
| 0522 | —CO—C3F7-n | H | H | —CO—CH3 | H | H |
| 0523 | —CO—C3F7-n | H | H | —C(=NOH)—CH3 | H | H |

TABLE A-continued

| Comp-No. | $R_1$ | $R_2$ | $R_3$ | $R_4$ | $R_5$ | $R_6$ |
|---|---|---|---|---|---|---|
| 0524 | —CO—$C_3F_7$-n | H | H | —CH(OH)—$CH_3$ | H | H |
| 0525 | —CO—$C_3F_7$-n | H | H | (3) —CO—O—$CH_2$— (4) | | |
| 0526 | —CO—$C_3F_7$-n | H | H | —$CH_2$—O—CO—$CH_3$ | H | H |
| 0527 | —CO—$C_3F_7$-n | H | H | —C(=NO—$CH_3$)—$CH_3$ | H | H |
| 0528 | —CO—$C_3F_7$-n | H | H | —CO—O—$CH_3$ | H | H |
| 0529 | —CO—$C_3F_7$-n | H | H | —NH—CO—$C_3H_5$-cycl. | H | H |
| 0530 | —CO—$C_3F_7$-n | H | H | —CO—$CH_3$ | Cl | H |
| 0531 | —CO—$C_3F_7$-n | H | H | —OH | H | H |
| 0532 | —CO—$C_3F_7$-n | H | H | —OH | —$OCH_3$ | H |
| 0533 | —CO—$C_3F_7$-n | H | H | —$OCH_3$ | H | —$OCH_3$ |
| 0534 | —CO—$C_3F_7$-n | H | H | —$SCH_3$ | H | H |
| 0535 | —CO—$C_3F_7$-n | H | H | —$OCH_3$ | H | H |
| 0536 | —CO—$C_3F_7$-n | H | H | —$OCH_3$ | —$OCH_3$ | —$OCH_3$ |
| 0537 | —CO—$C_3F_7$-n | H | H | —OH | —$OCH_3$ | —$OCH_3$ |
| 0538 | —CO—$C_3F_7$-n | H | H | H | —$SCH_3$ | H |
| 0539 | —CO—$C_3F_7$-n | H | H | H | —$OCH_3$ | H |
| 0540 | —CO—$C_3F_7$-n | H | H | —$OCH_3$ | —OH | H |
| 0541 | —CO—$C_3F_7$-n | H | —$OCH_3$ | —$CH_3$ | H | H |
| 0542 | —CO—$C_3F_7$-n | H | H | —$CH_2$—$CH_3$ | H | H |
| 0543 | —CO—$C_3F_7$-n | H | —$OCH_3$ | —CH($CH_3$)$_2$ | H | H |
| 0544 | —CO—$C_3F_7$-n | H | H | —$C_3H_7$-n | H | H |
| 0545 | —CO—$C_3F_7$-n | H | H | —$OCH_2$—$CH_3$ | H | H |
| 0546 | —CO—$C_3F_7$-n | H | H | F | H | H |
| 0547 | —CO—$C_3F_7$-u | H | H | Cl | H | H |
| 0548 | —CO—$C_3F_7$-n | H | H | Br | H | H |
| 0549 | —CO—$C_3F_7$-n | H | H | Cl | Cl | H |
| 0550 | —CO—$C_3F_7$-n | H | H | OH | OH | OH |
| 0551 | —CO—$C_3F_7$-n | H | Cl | Cl | H | Cl |
| 0552 | —CO—$C_3F_7$-n | H | H | —$CF_3$ | H | H |
| 0553 | —CO—$C_3F_7$-n | H | H | —$C_2F_5$ | H | H |
| 0554 | —CO—$C_3F_7$-n | H | H | —$C_4H_9$-tert | H | H |
| 0555 | —CO—$C_3F_7$-n | H | H | —$OC_3H_7$-i | H | H |
| 0556 | —CO—$C_3F_7$-n | H | H | —SO—$CH_3$ | H | H |
| 0557 | —CO—$C_3F_7$-n | H | H | —$SO_2$—$CH_3$ | H | H |
| 0558 | —CO—$C_3F_7$-n | H | H | —NH—$CH_2$—$CH_3$ | H | H |
| 0559 | —CO—$C_3F_7$-n | H | H | —O—$CH_2$—CH=$CH_2$ | H | H |
| 0560 | —CO—$C_3F_7$-n | H | H | —O—$CH_2$—C≡CH | H | H |
| 0561 | —CO—$C_3F_7$-n | H | H | —NH—$CH_2$—$CH_2$—NH—$CH_3$ | H | H |
| 0562 | —CO—$C_3F_7$-n | H | H | —$SO_2$—$C_2H_5$ | H | H |
| 0563 | —CO—$C_3F_7$-n | H | H | —$SO_2$—$CH_3$ | Cl | H |
| 0564 | —CO—$CH_2$—O—CO—$CH_3$ | H | H | —$CH_2$—O—$CH_3$ | H | H |
| 0565 | —CO—$CH_2$—O—CO—$CH_3$ | H | H | —NH—CO—$CH_3$ | H | H |
| 0566 | —CO—$CH_2$—O—CO—$CH_3$ | H | H | —$CH_2$—NH—CO—$CH_3$ | H | H |
| 0567 | —CO—$CH_2$—O—CO—$CH_3$ | H | H | —CH($CH_3$)—NH—CO—$CH_3$ | H | H |
| 0568 | —CO—$CH_2$—O—CO—$CH_3$ | H | H | —C($CH_3$)$_2$—NH—CO—$CH_3$ | H | H |
| 0569 | —CO—$CH_2$—O—CO—$CH_3$ | H | H | —CH($CH_3$)—O—$CH_3$ | H | H |
| 0570 | —CO—$CH_2$—O—CO—$CH_3$ | H | H | —C($CH_3$)$_2$—O—$CH_3$ | H | H |
| 0571 | —CO—$CH_2$—O—CO—$CH_3$ | H | H | —CH($CH_3$)—O—CO—$CH_3$ | H | H |
| 0572 | —CO—$CH_2$—O—CO—$CH_3$ | H | H | —$CH_2$—O—CO—$CH_3$ | H | H |
| 0573 | —CO—$CH_2$—O—CO—$CH_3$ | H | H | —C($CH_3$)$_2$—O—CO—$CH_3$ | H | H |
| 0574 | —CO—$CH_2$—O—CO—$CH_3$ | H | H | —$CH_2$—$CH_2$—O—H | H | H |
| 0575 | —CO—$CH_2$—O—CO—$CH_3$ | H | H | —$CH_2$—$CH_2$—O—$CH_3$ | H | H |
| 0576 | —CO—$CH_2$—O—CO—$CH_3$ | H | H | ![epoxide -CH2-CH(-O-)] (glycidyl) | H | H |
| 0577 | —CO—$CH_2$—O—CO—$CH_3$ | H | H | ![epoxide CH(CH3)-CH(-O-)] | H | H |
| 0578 | —CO—$CH_2$—O—CO—$CH_3$ | H | H | ![2-methyloxirane substituent] | H | H |
| 0579 | —CO—$CH_2$—O—CO—$CH_3$ | H | H | ![1,3-dioxolan-2-yl] | H | H |
| 0580 | —CO—$CH_2$—O—CO—$CH_3$ | H | H | ![oxazol-2-yl] | H | H |

TABLE A-continued

| Comp-No. | R₁ | R₂ | R₃ | R₄ | R₅ | R₆ |
|---|---|---|---|---|---|---|
| 0581 | —CO—CH₂—O—CO—CH₃ | H | H | 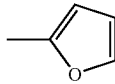 | H | H |
| 0582 | —CO—CH₂—O—CO—CH₃ | H | H | 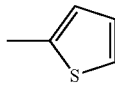 | H | H |
| 0583 | —CO—CH₂—O—CO—CH₃ | H | H | 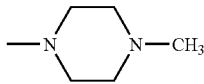 | H | H |
| 0584 | —CO—CH₂—O—CO—CH₃ | H | H | 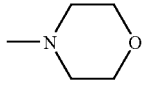 | H | H |
| 0585 | —CO—CH₂—O—CO—CH₃ | H | H | 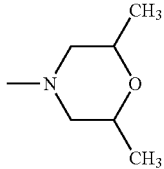 | H | H |
| 0586 | —CO—CH₂—O—CO—CH₃ | H | H | 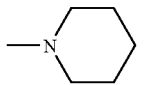 | H | H |
| 0587 | —CO—CH₂—O—CO—CH₃ | H | H | 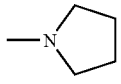 | H | H |
| 0588 | —CO—CH₂—O—CO—CH₃ | H | H | H | H | H |
| 0589 | —CO—CH₂—O—CO—CH₃ | H | H | CN | H | H |
| 0590 | —CO—CH₂—O—CO—CH₃ | H | H | —C(CH₃)₂—OH | H | H |
| 0591 | —CO—CH₂—O—CO—CH₃ | H | H | —CH₂—OH | H | H |
| 0592 | —CO—CH₂—O—CO—CH₃ | H | H | —CO—CH₃ | H | H |
| 0593 | —CO—CH₂—O—CO—CH₃ | H | H | —C(=NOH)—CH₃ | H | H |
| 0594 | —CO—CH₂—O—CO—CH₃ | H | H | —CH(OH)—CH₃ | H | H |
| 0595 | —CO—CH₂—O—CO—CH₃ | H | H | (3) —CO—O—CH₂— (4) | | H |
| 0596 | —CO—CH₂—O—CO—CH₃ | H | H | —CH₂—O—CO—CH₃ | H | H |
| 0597 | —CO—CH₂—O—CO—CH₃ | H | H | —C(=NO—CH₃)—CH₃ | H | H |
| 0598 | —CO—CH₂—O—CO—CH₃ | H | H | —CO—O—CH₃ | H | H |
| 0599 | —CO—CH₂—O—CO—CH₃ | H | H | —NH—CO—C₃H₅-cycl. | H | H |
| 0600 | —CO—CH₂—O—CO—CH₃ | H | H | —CO—CH₃ | Cl | H |
| 0601 | —CO—CH₂—O—CO—CH₃ | H | H | —OH | H | H |
| 0602 | —CO—CH₂—O—CO—CH₃ | H | H | —OH | —OCH₃ | H |
| 0603 | —CO—CH₂—O—CO—CH₃ | H | H | —OCH₃ | H | —OCH₃ |
| 0604 | —CO—CH₂—O—CO—CH₃ | H | H | —SCH₃ | H | H |
| 0605 | —CO—CH₂—O—CO—CH₃ | H | H | —OCH₃ | H | H |
| 0606 | —CO—CH₂—O—CO—CH₃ | H | H | —OCH₃ | —OCH₃ | —OCH₃ |
| 0607 | —CO—CH₂—O—CO—CH₃ | H | H | —OH | —OCH₃ | —OCH₃ |
| 0608 | —CO—CH₂—O—CO—CH₃ | H | H | H | —SCH₃ | H |
| 0609 | —CO—CH₂—O—CO—CH₃ | H | H | H | —OCH₃ | H |
| 0610 | —CO—CH₂—O—CO—CH₃ | H | H | —OCH₃ | —OH | H |
| 0611 | —CO—CH₂—O—CO—CH₃ | H | —OCH₃ | —CH₃ | H | H |
| 0612 | —CO—CH₂—O—CO—CH₃ | H | H | —CH₂—CH₃ | H | H |
| 0613 | —CO—CH₂—O—CO—CH₃ | H | —OCH₃ | —CH(CH₃)₂ | H | H |
| 0614 | —CO—CH₂—O—CO—CH₃ | H | H | —C₃H₇-n | H | H |
| 0615 | —CO—CH₂—O—CO—CH₃ | H | H | —OCH₂—CH₃ | H | H |
| 0616 | —CO—CH₂—O—CO—CH₃ | H | H | F | H | H |
| 0617 | —CO—CH₂—O—CO—CH₃ | H | H | Cl | H | H |
| 0618 | —CO—CH₂—O—CO—CH₃ | H | H | Br | H | H |
| 0619 | —CO—CH₂—O—CO—CH₃ | H | H | Cl | Cl | H |
| 0620 | —CO—CH₂—O—CO—CH₃ | H | H | OH | OH | OH |
| 0621 | —CO—CH₂—O—CO—CH₃ | H | Cl | Cl | H | Cl |
| 0622 | —CO—CH₂—O—CO—CH₃ | H | H | —CF₃ | H | H |
| 0623 | —CO—CH₂—O—CO—CH₃ | H | H | —OCF₃ | H | H |

TABLE A-continued

| Comp-No. | R$_1$ | R$_2$ | R$_3$ | R$_4$ | R$_5$ | R$_6$ |
|---|---|---|---|---|---|---|
| 0624 | —CO—CH$_2$—O—CO—CH$_3$ | H | H | —C$_2$F$_5$ | H | H |
| 0625 | —CO—CH$_2$—O—CO—CH$_3$ | H | H | —C$_4$H$_9$-tert | H | H |
| 0626 | —CO—CH$_2$—O—CO—CH$_3$ | H | H | —OC$_3$H$_7$-i | H | H |
| 0627 | —CO—CH$_2$—O—CO—CH$_3$ | H | H | —SO—CH$_3$ | H | H |
| 0628 | —CO—CH$_2$—O—CO—CH$_3$ | H | H | —SO$_2$—CH$_3$ | H | H |
| 0629 | —CO—CH$_2$—O—CO—CH$_3$ | H | H | —NH—CH$_2$—CH$_3$ | H | H |
| 0630 | —CO—CH$_2$—O—CO—CH$_3$ | H | H | —O—CH$_2$—CH=CH$_2$ | H | H |
| 0631 | —CO—CH$_2$—O—CO—CH$_3$ | H | H | —O—CH$_2$—C≡CH | H | H |
| 0632 | —CO—CH$_2$—O—CO—CH$_3$ | H | H | —NH—CH$_2$—CH$_2$—NH—CH$_3$ | H | H |
| 0633 | —CO—CH$_2$—O—CO—CH$_3$ | H | H | —SO$_2$—C$_2$H$_5$ | H | H |
| 0634 | —CO—CH$_2$—O—CO—CH$_3$ | H | H | —SO$_2$—CH$_3$ | Cl | H |
| 0635 | —CO—C$_2$F$_5$ | H | H | —CH$_2$—O—CH$_3$ | H | H |
| 0636 | —CO—C$_2$F$_5$ | H | H | —NH—CO—CH$_3$ | H | H |
| 0637 | —CO—C$_2$F$_5$ | H | H | —CH$_2$—NH—CO—CH$_3$ | H | H |
| 0638 | —CO—C$_2$F$_5$ | H | H | —CH(CH$_3$)—NH—CO—CH$_3$ | H | H |
| 0639 | —CO—C$_2$F$_5$ | H | H | —C(CH$_3$)$_2$—NH—CO—CH$_3$ | H | H |
| 0640 | —CO—C$_2$F$_5$ | H | H | —CH(CH$_3$)—O—CH$_3$ | H | H |
| 0641 | —CO—C$_2$F$_5$ | H | H | —C(CH$_3$)$_2$—O—CH$_3$ | H | H |
| 0642 | —CO—C$_2$F$_5$ | H | H | —CH(CH$_3$)—O—CO—CH$_3$ | H | H |
| 0643 | —CO—C$_2$F$_5$ | H | H | —CH$_2$—O—CO—CH$_3$ | H | H |
| 0644 | —CO—C$_2$F$_5$ | H | H | —C(CH$_3$)$_2$—O—CO—CH$_3$ | H | H |
| 0645 | —CO—C$_2$F$_5$ | H | H | —CH$_2$—CH$_2$—O—H | H | H |
| 0646 | —CO—C$_2$F$_5$ | H | H | —CH$_2$—CH$_2$—O—CH$_3$ | H | H |
| 0647 | —CO—C$_2$F$_5$ | H | H | 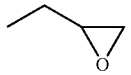 | H | H |
| 0648 | —CO—C$_2$F$_5$ | H | H | 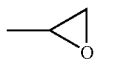 | H | H |
| 0649 | —CO—C$_2$F$_5$ | H | H | 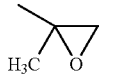 | H | H |
| 0650 | —CO—C$_2$F$_5$ | H | H | 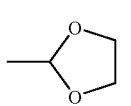 | H | H |
| 0651 | —CO—C$_2$F$_5$ | H | H | 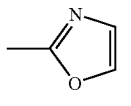 | H | H |
| 0652 | —CO—C$_2$F$_5$ | H | H | 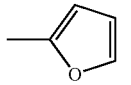 | H | H |
| 0653 | —CO—C$_2$F$_5$ | H | H | 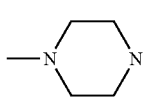 | H | H |
| 0654 | —CO—C$_2$F$_5$ | H | H | 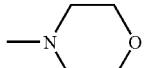 | H | H |
| 0655 | —CO—C$_2$F$_5$ | H | H | 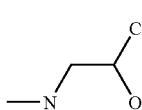 | H | H |
| 0656 | —CO—C$_2$F$_5$ | H | H | 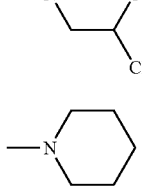 | H | H |

TABLE A-continued

| Comp-No. | R₁ | R₂ | R₃ | R₄ | R₅ | R₆ |
|---|---|---|---|---|---|---|
| 0657 | —CO—C₂F₅ | H | H | pyrrolidin-1-yl | H | H |
| 0658 | —CO—C₂F₅ | H | H | H | H | H |
| 0659 | —CO—C₂F₅ | H | H | CN | H | H |
| 0660 | —CO—C₂F₅ | H | H | —C(CH₃)₂—OH | H | H |
| 0661 | —CO—C₂F₅ | H | H | —CH₂—OH | H | H |
| 0662 | —CO—C₂F₅ | H | H | —CO—CH₃ | H | H |
| 0663 | —CO—C₂F₅ | H | H | —C(=NOH)—CH₃ | H | H |
| 0664 | —CO—C₂F₅ | H | H | —CH(OH)—CH₃ | H | H |
| 0665 | —CO—C₂F₅ | H | H | (3) —CO—O—CH₂— (4) |  | H |
| 0666 | —CO—C₂F₅ | H | H | —CH₂—O—CO—CH₃ | H | H |
| 0667 | —CO—C₂F₅ | H | H | —C(=NO—CH₃)—CH₃ | H | H |
| 0668 | —CO—C₂F₅ | H | H | —CO—O—CH₃ | H | H |
| 0669 | —CO—C₂F₅ | H | H | —NH—CO—C₃H₅-cycl. | H | H |
| 0670 | —CO—C₂F₅ | H | H | —CO—CH₃ | Cl | H |
| 0671 | —CO—C₂F₅ | H | H | —OH | H | H |
| 0672 | —CO—C₂F₅ | H | H | —OH | —OCH₃ | H |
| 0673 | —CO—C₂F₅ | H | H | —OCH₃ | H | —OCH₃ |
| 0674 | —CO—C₂F₅ | H | H | —SCH₃ | H | H |
| 0675 | —CO—C₂F₅ | H | H | —OCH₃ | H | H |
| 0676 | —CO—C₂F₅ | H | H | —OCH₃ | —OCH₃ | —OCH₃ |
| 0677 | —CO—C₂F₅ | H | H | —OH | —OCH₃ | —OCH₃ |
| 0678 | —CO—C₂F₅ | H | H | H | —SCH₃ | H |
| 0679 | —CO—C₂F₅ | H | H | H | —OCH₃ | H |
| 0680 | —CO—C₂F₅ | H | H | —OCH₃ | —OH | H |
| 0681 | —CO—C₂F₅ | H | —OCH₃ | —CH₃ | H | H |
| 0682 | —CO—C₂F₅ | H | H | —CH₂—CH₃ | H | H |
| 0683 | —CO—C₂F₅ | H | —OCH₃ | —CH(CH₃)₂ | H | H |
| 0684 | —CO—C₂F₅ | H | H | —C₃H₇-n | H | H |
| 0685 | —CO—C₂F₅ | H | H | —OCH₂—CH₃ | H | H |
| 0686 | —CO—C₂F₅ | H | H | F | H | H |
| 0687 | —CO—C₂F₅ | H | H | Cl | H | H |
| 0688 | —CO—C₂F₅ | H | H | Br | H | H |
| 0689 | —CO—C₂F₅ | H | H | Cl | Cl | H |
| 0690 | —CO—C₂F₅ | H | H | OH | OH | OH |
| 0691 | —CO—C₂F₅ | H | Cl | Cl | H | Cl |
| 0692 | —CO—C₂F₅ | H | H | —CF₃ | H | H |
| 0693 | —CO—C₂F₅ | H | H | —OCF₃ | H | H |
| 0694 | —CO—C₂F₅ | H | H | —C₂F₅ | H | H |
| 0695 | —CO—C₂F₅ | H | H | —C₄H₉-tert | H | H |
| 0696 | —CO—C₂F₅ | H | H | —OC₃H₇-i | H | H |
| 0697 | —CO—C₂F₅ | H | H | —SO—CH₃ | H | H |
| 0698 | —CO—C₂F₅ | H | H | —SO₂—CH₃ | H | H |
| 0699 | —CO—C₂F₅ | H | H | —NH—CH₂—CH₃ | H | H |
| 0700 | —CO—C₂F₅ | H | H | —O—CH₂—CH=CH₂ | H | H |
| 0701 | —CO—C₂F₅ | H | H | —O—CH₂—C≡CH | H | H |
| 0702 | —CO—C₂F₅ | H | H | —NH—CH₂—CH₂—NH—CH₃ | H | H |
| 0703 | —CO—C₂F₅ | H | H | —SO₂—C₂H₅ | H | H |
| 0704 | —CO—C₂F₅ | H | H | —SO₂—CH₃ | Cl | H |
| 0705 | —CO—CF₃ | H | H | —CH₂—O—CH₃ | H | H |
| 0706 | —CO—CF₃ | H | H | —NH—CO—CH₃ | H | H |
| 0707 | —CO—CF₃ | H | H | —CH₂—NH—CO—CH₃ | H | H |
| 0708 | —CO—CF₃ | H | H | —CH(CH₃)—NH—CO—CH₃ | H | H |
| 0709 | —CO—CF₃ | H | H | —C(CH₃)₂—NH—CO—CH₃ | H | H |
| 0710 | —CO—CF₃ | H | H | —CH(CH₃)—O—CH₃ | H | H |
| 0711 | —CO—CF₃ | H | H | —C(CH₃)₂—O—CH₃ | H | H |
| 0712 | —CO—CF₃ | H | H | —CH(CH₃)—O—CO—CH₃ | H | H |
| 0713 | —CO—CF₃ | H | H | —CH₂—O—CO—CH₃ | H | H |
| 0714 | —CO—CF₃ | H | H | —C(CH₃)₂—O—CO—CH₃ | H | H |
| 0715 | —CO—CF₃ | H | H | —CH₂—CH₂—O—H | H | H |
| 0716 | —CO—CF₃ | H | H | —CH₂—CH₂—O—CH₃ | H | H |
| 0717 | —CO—CF₃ | H | H | oxiran-2-yl | H | H |
| 0718 | —CO—CF₃ | H | H | oxiran-2-yl | H | H |

TABLE A-continued

| Comp-No. | R₁ | R₂ | R₃ | R₄ | R₅ | R₆ |
|---|---|---|---|---|---|---|
| 0719 | —CO—CF₃ | H | H | 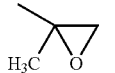 | H | H |
| 0720 | —CO—CF₃ | H | H | 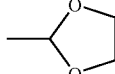 | H | H |
| 0721 | —CO—CF₃ | H | H | 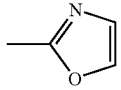 | H | H |
| 0722 | —CO—CF₃ | H | H | 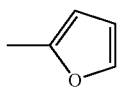 | H | H |
| 0723 | —CO—CF₃ | H | H | 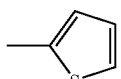 | H | H |
| 0724 | —CO—CF₃ | H | H | 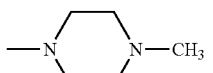 | H | H |
| 0725 | —CO—CF₃ | H | H | 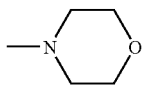 | H | H |
| 0726 | —CO—CF₃ | H | H | 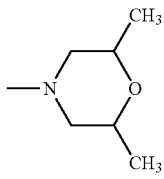 | H | H |
| 0727 | —CO—CF₃ | H | H | 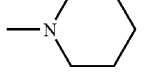 | H | H |
| 0728 | —CO—CF₃ | H | H | 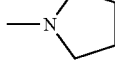 | H | H |
| 0729 | —CO—CF₃ | H | H | H | H | H |
| 0730 | —CO—CF₃ | H | H | CN | H | H |
| 0731 | —CO—CF₃ | H | H | —C(CH₃)₂—OH | H | H |
| 0732 | —CO—CF₃ | H | H | —CH₂—OH | H | H |
| 0733 | —CO—CF₃ | H | H | —CO—CH₃ | H | H |
| 0734 | —CO—CF₃ | H | H | —C(=NOH)—CH₃ | H | H |
| 0735 | —CO—CF₃ | H | H | —CH(OH)—CH₃ | H | H |
| 0736 | —CO—CF₃ | H | H | (3) —CO—O—CH₂— (4) | | H |
| 0737 | —CO—CF₃ | H | H | —CH₂—O—CO—CH₃ | | |
| 0738 | —CO—CF₃ | H | H | —C(=NO—CH₃)—CH₃ | H | H |
| 0739 | —CO—CF₃ | H | H | —CO—O—CH₃ | H | H |
| 0740 | —CO—CF₃ | H | H | —NH—CO—C₃H₅-cycl. | H | H |
| 0741 | —CO—CF₃ | H | H | —CO—CH₃ | Cl | H |
| 0742 | —CO—CF₃ | H | H | —OH | H | H |
| 0743 | —CO—CF₃ | H | H | —OH | —OCH₃ | H |
| 0744 | —CO—CF₃ | H | H | —OCH₃ | H | —OCH₃ |
| 0745 | —CO—CF₃ | H | H | —SCH₃ | H | H |
| 0746 | —CO—CF₃ | H | H | —OCH₃ | H | H |
| 0747 | —CO—CF₃ | H | H | —OCH₃ | —OCH₃ | —OCH₃ |
| 0748 | —CO—CF₃ | H | H | —OH | —OCH₃ | —OCH₃ |
| 0749 | —CO—CF₃ | H | H | H | —SCH₃ | H |
| 0750 | —CO—CF₃ | H | H | H | —OCH₃ | H |

TABLE A-continued

| Comp-No. | R$_1$ | R$_2$ | R$_3$ | R$_4$ | R$_5$ | R$_6$ |
|---|---|---|---|---|---|---|
| 0751 | —CO—CF$_3$ | H | H | —OCH$_3$ | —OH | H |
| 0752 | —CO—CF$_3$ | H | —OCH$_3$ | —CH$_3$ | H | H |
| 0753 | —CO—CF$_3$ | H | —OCH$_3$ | —CH(CH$_3$)$_2$ | H | H |
| 0754 | —CO—CF$_3$ | H | H | —C$_3$H$_7$-n | H | H |
| 0755 | —CO—CF$_3$ | H | H | —OCH$_2$—CH$_3$ | H | H |
| 0756 | —CO—CF$_3$ | H | H | F | H | H |
| 0757 | —CO—CF$_3$ | H | H | Cl | H | H |
| 0758 | —CO—CF$_3$ | H | H | Br | H | H |
| 0759 | —CO—CF$_3$ | H | H | Cl | Cl | H |
| 0760 | —CO—CF$_3$ | H | H | OH | OH | OH |
| 0761 | —CO—CF$_3$ | H | Cl | Cl | H | Cl |
| 0762 | —CO—CF$_3$ | H | H | —CF$_3$ | H | H |
| 0763 | —CO—CF$_3$ | H | H | —OCF$_3$ | H | H |
| 0764 | —CO—CF$_3$ | H | H | —C$_2$F$_5$ | H | H |
| 0765 | —CO—CF$_3$ | H | H | —C$_4$H$_9$-tert | H | H |
| 0766 | —CO—CF$_3$ | H | H | —OC$_3$H$_7$-i | H | H |
| 0767 | —CO—CF$_3$ | H | H | —SO—CH$_3$ | H | H |
| 0768 | —CO—CF$_3$ | H | H | —SO$_2$—CH$_3$ | H | H |
| 0769 | —CO—CF$_3$ | H | H | —NH—CH$_2$—CH$_3$ | H | H |
| 0770 | —CO—CF$_3$ | H | H | —O—CH$_2$—CH=CH$_2$ | H | H |
| 0771 | —CO—CF$_3$ | H | H | —O—CH$_2$—C≡CH | H | H |
| 0772 | —CO—CF$_3$ | H | H | —NH—CH$_2$—CH$_2$—NH—CH$_3$ | H | H |
| 0773 | —CO—CF$_3$ | H | H | —SO$_2$—C$_2$H$_5$ | H | H |
| 0774 | —CO—CF$_3$ | H | H | —SO$_2$—CH$_3$ | Cl | H |
| 0775 | | —(CH$_2$)$_4$— | H | —CH$_2$—O—CH$_3$ | H | H |
| 0776 | | —(CH$_2$)$_4$— | H | —NH—CO—CH$_3$ | H | H |
| 0777 | | —(CH$_2$)$_4$— | H | —CH$_2$—NH—CO—CH$_3$ | H | H |
| 0778 | | —(CH$_2$)$_4$— | H | —CH(CH$_3$)—NH—CO—CH$_3$ | H | H |
| 0779 | | —(CH$_2$)$_4$— | H | —C(CH$_3$)$_2$—NH—CO—CH$_3$ | H | H |
| 0780 | | —(CH$_2$)$_4$— | H | —CH(CH$_3$)—O—CH$_3$ | H | H |
| 0781 | | —(CH$_2$)$_4$— | H | —C(CH$_3$)$_2$—O—CH$_3$ | H | H |
| 0782 | | —(CH$_2$)$_4$— | H | —CH(CH$_3$)—O—CO—CH$_3$ | H | H |
| 0783 | | —(CH$_2$)$_4$— | H | —CH$_2$—O—CO—CH$_3$ | H | H |
| 0784 | | —(CH$_2$)$_4$— | H | —C(CH$_3$)$_2$—O—CO—CH$_3$ | H | H |
| 0785 | | —(CH$_2$)$_4$— | H | —CH$_2$—CH$_2$—O—H | H | H |
| 0786 | | —(CH$_2$)$_4$— | H | —CH$_2$—CH$_2$—O—CH$_3$ | H | H |
| 0787 | | —(CH$_2$)$_4$— | H | CH$_2$-epoxide (glycidyl) | H | H |
| 0788 | | —(CH$_2$)$_4$— | H | epoxide (oxiranyl) | H | H |
| 0789 | | —(CH$_2$)$_4$— | H | 2-methyloxiranyl | H | H |
| 0790 | | —(CH$_2$)$_4$— | H | 1,3-dioxolan-2-yl | H | H |
| 0791 | | —(CH$_2$)$_4$— | H | oxazol-2-yl | H | H |
| 0792 | | —(CH$_2$)$_4$— | H | furan-2-yl | H | H |
| 0793 | | —(CH$_2$)$_4$— | H | thien-2-yl | H | H |
| 0794 | | —(CH$_2$)$_4$— | H | —N(4-methylpiperazin-1-yl)—CH$_3$ | H | H |

TABLE A-continued

| Comp-No. | R₁ | R₂ | R₃ | R₄ | R₅ | R₆ |
|---|---|---|---|---|---|---|
| 0795 | | —(CH₂)₄— | H | 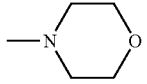 | H | H |
| 0796 | | —(CH₂)₄— | H | 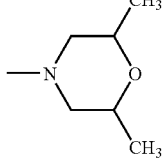 | H | H |
| 0797 | | —(CH₂)₄— | H | 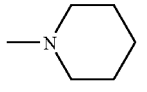 | H | H |
| 0798 | | —(CH₂)₄— | H | 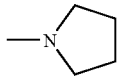 | H | H |
| 0799 | | —(CH₂)₄— | H | H | H | H |
| 0800 | | —(CH₂)₄— | H | CN | H | H |
| 0801 | | —(CH₂)₄— | H | —C(CH₃)₂—OH | H | H |
| 0802 | | —(CH₂)₄— | H | —CH₂—OH | H | H |
| 0803 | | —(CH₂)₄— | H | —CO—CH₃ | H | H |
| 0804 | | —(CH₂)₄— | H | —C(=NOH)—CH₃ | H | H |
| 0805 | | —(CH₂)₄— | H | —CH(OH)—CH₃ | H | H |
| 0806 | | —(CH₂)₄— | H | (3) —CO—O—CH₂— (4) | | H |
| 0807 | | —(CH₂)₄— | H | —CH₂—O—CO—CH₃ | H | H |
| 0808 | | —(CH₂)₄— | H | —C(=NO—CH₃)—CH₃ | H | H |
| 0809 | | —(CH₂)₄— | H | —CO—O—CH₃ | H | H |
| 0810 | | —(CH₂)₄— | H | —NH—CO—C₃H₅-cycl. | H | H |
| 0811 | | —(CH₂)₄— | H | —CO—CH₃ | Cl | H |
| 0812 | | —(CH₂)₄— | H | —OH | H | H |
| 0813 | | —(CH₂)₄— | H | —OH | —OCH₃ | H |
| 0814 | | —(CH₂)₄— | H | —OCH₃ | H | —OCH₃ |
| 0815 | | —(CH₂)₄— | H | —SCH₃ | H | H |
| 0816 | | —(CH₂)₄— | H | —OCH₃ | H | H |
| 0817 | | —(CH₂)₄— | H | —OCH₃ | —OCH₃ | —OCH₃ |
| 0818 | | —(CH₂)₄— | H | —OH | —OCH₃ | —OCH₃ |
| 0819 | | —(CH₂)₄— | H | H | —SCH₃ | H |
| 0820 | | —(CH₂)₄— | H | H | —OCH₃ | H |
| 0821 | | —(CH₂)₄— | H | —OCH₃ | —OH | H |
| 0822 | | —(CH₂)₄— | —OCH₃ | —CH₃ | H | H |
| 0823 | | —(CH₂)₄— | H | —CH₂—CH₃ | H | H |
| 0824 | | —(CH₂)₄— | —OCH₃ | —CH(CH₃)₂ | H | H |
| 0825 | | —(CH₂)₄— | H | —C₃H₇-n | H | H |
| 0826 | | —(CH₂)₄— | H | —OCH₂—CH₃ | H | H |
| 0827 | | —(CH₂)₄— | H | F | H | H |
| 0828 | | —(CH₂)₄— | H | Cl | H | H |
| 0829 | | —(CH₂)₄— | H | Br | H | H |
| 0830 | | —(CH₂)₄— | H | Cl | Cl | H |
| 0831 | | —(CH₂)₄— | H | OH | OH | OH |
| 0832 | | —(CH₂)₄— | Cl | Cl | H | Cl |
| 0833 | | —(CH₂)₄— | H | —CF₃ | H | H |
| 0834 | | —(CH₂)₄— | H | —OCF₃ | H | H |
| 0835 | | —(CH₂)₄— | H | —C₂F₅ | H | H |
| 0836 | | —(CH₂)₄— | H | —C₄H₉-tert | H | H |
| 0837 | | —(CH₂)₄— | H | —OC₃H₇-i | H | H |
| 0838 | | —(CH₂)₄— | H | —SO—CH₃ | H | H |
| 0839 | | —(CH₂)₄— | H | —SO₂—CH₃ | H | H |
| 0840 | | —(CH₂)₄— | H | —NH—CH₂—CH₃ | H | H |
| 0841 | | —(CH₂)₄— | H | —O—CH₂—CH=CH₂ | H | H |
| 0842 | | —(CH₂)₄— | H | —O—CH₂—C≡CH | H | H |
| 0843 | | —(CH₂)₄— | H | —NH—CH₂—CH₂—NH—CH₃ | H | H |
| 0844 | | —(CH₂)₄— | H | —SO₂—C₂H₅ | H | H |
| 0845 | | —(CH₂)₄— | H | —SO₂—CH₃ | Cl | H |
| 0846 | | —N=C(CH₃)—N(CH₃)₂ | H | —CH₂—O—CH₃ | H | H |
| 0847 | | —N=C(CH₃)—N(CH₃)₂ | H | —NH—CO—CH₃ | H | H |
| 0848 | | —N=C(CH₃)—N(CH₃)₂ | H | —CH₂—NH—CO—CH₃ | H | H |
| 0849 | | —N=C(CH₃)—N(CH₃)₂ | H | —CH(CH₃)—NH—CO—CH₃ | H | H |
| 0850 | | —N=C(CH₃)—N(CH₃)₂ | H | —C(CH₃)₂—NH—CO—CH₃ | H | H |

TABLE A-continued

| Comp-No. | R₁ | R₂ | R₃ | R₄ | R₅ | R₆ |
|---|---|---|---|---|---|---|
| 0851 | | —N=C(CH₃)—N(CH₃)₂ | H | —CH(CH₃)—O—CH₃ | H | H |
| 0852 | | —N=C(CH₃)—N(CH₃)₂ | H | —C(CH₃)₂—O—CH₃ | H | H |
| 0853 | | —N=C(CH₃)—N(CH₃)₂ | H | —CH₂—O—CO—CH₃ | H | H |
| 0854 | | —N=C(CH₃)—N(CH₃)₂ | H | —C(CH₃)₂—O—CO—CH₃ | H | H |
| 0855 | | —N=C(CH₃)—N(CH₃)₂ | H | —CH₂—CH₂—O—H | H | H |
| 0856 | | —N=C(CH₃)—N(CH₃)₂ | H | —CH₂—CH₂—O—CH₃ | H | H |
| 0857 | | —N=C(CH₃)—N(CH₃)₂ | H | 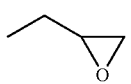 | H | H |
| 0858 | | —N=C(CH₃)—N(CH₃)₂ | H |  | H | H |
| 0859 | | —N=C(CH₃)—N(CH₃)₂ | H |  | H | H |
| 0860 | | —N=C(CH₃)—N(CH₃)₂ | H | 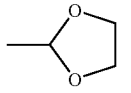 | H | H |
| 0861 | | —N=C(CH₃)—N(CH₃)₂ | H | 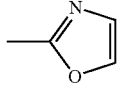 | H | H |
| 0862 | | —N=C(CH₃)—N(CH₃)₂ | H | 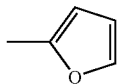 | H | H |
| 0863 | | —N=C(CH₃)—N(CH₃)₂ | H | 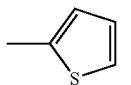 | H | H |
| 0864 | | —N=C(CH₃)—N(CH₃)₂ | H | 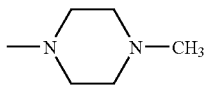 | H | H |
| 0865 | | —N=C(CH₃)—N(CH₃)₂ | H |  | H | H |
| 0866 | | —N=C(CH₃)—N(CH₃)₂ | H | 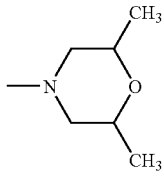 | H | H |
| 0867 | | —N=C(CH₃)—N(CH₃)₂ | H | 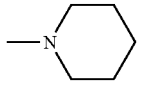 | H | H |
| 0868 | | —N=C(CH₃)—N(CH₃)₂ | H | 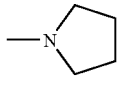 | H | H |
| 0869 | | —N=C(CH₃)—N(CH₃)₂ | H | H | H | H |
| 0870 | | —N=C(CH₃)—N(CH₃)₂ | H | CN | H | H |
| 0871 | | —N=C(CH₃)—N(CH₃)₂ | H | —C(CH₃)₂—OH | H | H |
| 0872 | | —N=C(CH₃)—N(CH₃)₂ | H | —CH₂—OH | H | H |
| 0873 | | —N=C(CH₃)—N(CH₃)₂ | H | —CO—CH₃ | H | H |
| 0874 | | —N=C(CH₃)—N(CH₃)₂ | H | —C(=NOH)—CH₃ | H | H |
| 0875 | | —N=C(CH₃)—N(CH₃)₂ | H | —CH(OH)—CH₃ | H | H |

TABLE A-continued

| Comp-No. | R₁ | R₂ | R₃ | R₄ | R₅ | R₆ |
|---|---|---|---|---|---|---|
| 0876 | | —N=C(CH₃)—N(CH₃)₂ | H | (3) —CO—O—CH₂— (4) | | H |
| 0877 | | —N=C(CH₃)—N(CH₃)₂ | H | —CH₂—O—CO—CH₃ | H | H |
| 0878 | | —N=C(CH₃)—N(CH₃)₂ | H | —C(=NO—CH₃)—CH₃ | H | H |
| 0879 | | —N=C(CH₃)—N(CH₃)₂ | H | —CO—O—CH₃ | H | H |
| 0880 | | —N=C(CH₃)—N(CH₃)₂ | H | —NH—CO—C₃H₅-cycl. | H | H |
| 0881 | | —N=C(CH₃)—N(CH₃)₂ | H | —CO—CH₃ | Cl | H |
| 0882 | | —N=C(CH₃)—N(CH₃)₂ | H | —OH | H | H |
| 0883 | | —N=C(CH₃)—N(CH₃)₂ | H | —OH | —OCH₃ | H |
| 0884 | | —N=C(CH₃)—N(CH₃)₂ | H | —OCH₃ | H | —OCH₃ |
| 0885 | | —N=C(CH₃)—N(CH₃)₂ | H | —SCH₃ | H | H |
| 0886 | | —N=C(CH₃)—N(CH₃)₂ | H | —OCH₃ | H | H |
| 0887 | | —N=C(CH₃)—N(CH₃)₂ | H | OCH₃ | —OCH₃ | —OCH₃ |
| 0888 | | —N=C(CH₃)—N(CH₃)₂ | H | —OH | —OCH₃ | —OCH₃ |
| 0889 | | —N=C(CH₃)—N(CH₃)₂ | H | H | —SCH₃ | H |
| 0890 | | —N=C(CH₃)—N(CH₃)₂ | H | H | —SCH₃ | H |
| 0891 | | —N=C(CH₃)—N(CH₃)₂ | H | —OCH₃ | —OH | H |
| 0892 | | —N=C(CH₃)—N(CH₃)₂ | —OCH₃ | —CH₃ | H | H |
| 0893 | | —N=C(CH₃)—N(CH₃)₂ | H | —CH₂—CH₃ | H | H |
| 0894 | | —N=C(CH₃)—N(CH₃)₂ | —OCH₃ | —CH(CH₃)₂ H | H | |
| 0895 | | —N=C(CH₃)—N(CH₃)₂ | H | —C₃H₇-n | H | H |
| 0896 | | —N=C(CH₃)—N(CH₃)₂ | H | —OCH₂—CH₃ | H | H |
| 0897 | | —N=C(CH₃)—N(CH₃)₂ | H | F | H | H |
| 0898 | | —N=C(CH₃)—N(CH₃)₂ | H | Cl | H | H |
| 0899 | | —N=C(CH₃)—N(CH₃)₂ | H | Br | H | H |
| 0900 | | —N=C(CH₃)—N(CH₃)₂ | H | Cl | Cl | H |
| 0901 | | —N=C(CH₃)—N(CH₃)₂ | H | OH | OH | OH |
| 0902 | | —N=C(CH₃)—N(CH₃)₂ | Cl | Cl | H | Cl |
| 0903 | | —N=C(CH₃)—N(CH₃)₂ | H | —CF₃ | H | H |
| 0904 | | —N=C(CH₃)—N(CH₃)₂ | H | —OCF₃ | H | H |
| 0905 | | —N=C(CH₃)—N(CH₃)₂ | H | —C₂F₅ | H | H |
| 0906 | | —N=C(CH₃)—N(CH₃)₂ | H | —C₄H₉-tert | H | H |
| 0907 | | —N=C(CH₃)—N(CH₃)₂ | H | —OC₃H₇-i | H | H |
| 0908 | | —N=C(CH₃)—N(CH₃)₂ | H | —SO—CH₃ | H | H |
| 0909 | | —N=C(CH₃)—N(CH₃)₂ | H | —SO₂—CH₃ | H | H |
| 0910 | | —N=C(CH₃)—N(CH₃)₂ | H | —NH—CH₂—CH₃ | H | H |
| 0911 | | —N=C(CH₃)—N(CH₃)₂ | H | —O—CH₂—CH=CH₂ | H | H |
| 0912 | | —N=C(CH₃)—N(CH₃)₂ | H | —O—CH₂—C≡CH | H | H |
| 0913 | | —N=C(CH₃)—N(CH₃)₂ | H | —NH—CH₂—CH₂—NH—CH₃ | H | H |
| 0914 | | —N=C(CH₃)—N(CH₃)₂ | H | —SO₂—C₂H₅ | H | H |
| 0915 | | —N=C(CH₃)—N(CH₃)₂ | H | —SO₂—CH₃ | Cl | H |
| 0916 | | —N=CH—N(CH₃)₂ | H | —CH₂—O—CH₃ | H | H |
| 0917 | | —N=CH—N(CH₃)₂ | H | —NH—CO—CH₃ | H | H |
| 0918 | | —N=CH—N(CH₃)₂ | H | —CH₂—NH—CO—CH₃ | H | H |
| 0919 | | —N=CH—N(CH₃)₂ | H | —CH(CH₃)—NH—CO—CH₃ | H | H |
| 0920 | | —N=CH—N(CH₃)₂ | H | —C(CH₃)₂—NH—CO—CH₃ | H | H |
| 0921 | | —N=CH—N(CH₃)₂ | H | —CH(CH₃)—O—CH₃ | H | H |
| 0922 | | —N=CH—N(CH₃)₂ | H | —C(CH₃)₂—O—CH₃ | H | H |
| 0923 | | —N=CH—N(CH₃)₂ | H | —CH(CH₃)—O—CO—CH₃ | H | H |
| 0924 | | —N=CH—N(CH₃)₂ | H | —CH₂—O—CO—CH₃ | H | H |
| 0925 | | —N=CH—N(CH₃)₂ | H | —C(CH₃)₂—O—CO—CH₃ | H | H |
| 0926 | | —N=CH—N(CH₃)₂ | H | —CH₂—CH₂—O—H | H | H |
| 0927 | | —N=CH—N(CH₃)₂ | H | —CH₂—CH₂—O—CH₃ | H | H |
| 0928 | | —N=CH—N(CH₃)₂ | H | (epoxide) | H | H |
| 0929 | | —N=CH—N(CH₃)₂ | H | (epoxide) | H | H |
| 0930 | | —N=CH—N(CH₃)₂ | H | (methyl-epoxide) | H | H |
| 0931 | | —N=CH—N(CH₃)₂ | H | (1,3-dioxolane) | H | H |
| 0932 | | —N=CH—N(CH₃)₂ | H | (oxazole) | H | H |

TABLE A-continued

| Comp-No. | R₁ | R₂ | R₃ | R₄ | R₅ | R₆ |
|---|---|---|---|---|---|---|
| 0933 | | —N=CH—N(CH₃)₂ | H | 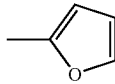 | H | H |
| 0934 | | —N=CH—N(CH₃)₂ | H | 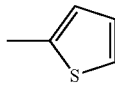 | H | H |
| 0935 | | —N=CH—N(CH₃)₂ | H | 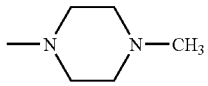 | H | H |
| 0936 | | —N=CH—N(CH₃)₂ | H | 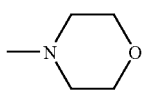 | H | H |
| 0937 | | —N=CH—N(CH₃)₂ | H | 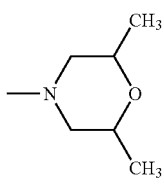 | H | H |
| 0938 | | —N=CH—N(CH₃)₂ | H | 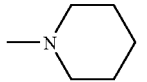 | H | H |
| 0939 | | —N=CH—N(CH₃)₂ | H | 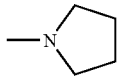 | H | H |
| 0940 | | —N=CH—N(CH₃)₂ | H | H | H | H |
| 0941 | | —N=CH—N(CH₃)₂ | H | CN | H | H |
| 0942 | | —N=CH—N(CH₃)₂ | H | —C(CH₃)₂—OH | H | H |
| 0943 | | —N=CH—N(CH₃)₂ | H | —CH₂—OH | H | H |
| 0944 | | —N=CH—N(CH₃)₂ | H | —CO—CH₃ | H | H |
| 0945 | | —N=CH—N(CH₃)₂ | H | —C(=NOH)—CH₃ | H | H |
| 0946 | | —N=CH—N(CH₃)₂ | H | —CH(OH)—CH₃ | H | H |
| 0947 | | —N=CH—N(CH₃)₂ | H | (3) —CO—O—CH₂— (4) | | H |
| 0948 | | —N=CH—N(CH₃)₂ | H | —CH₂—O—CO—CH₃ | H | H |
| 0949 | | —N=CH—N(CH₃)₂ | H | —C(=NO—CH₃)—CH₃ | H | H |
| 0950 | | —N=CH—N(CH₃)₂ | H | —CO—O—CH₃ | H | H |
| 0951 | | —N=CH—N(CH₃)₂ | H | —NH—CO—C₃H₅-cycl. | H | H |
| 0952 | | —N=CH—N(CH₃)₂ | H | —CO—CH₃ | Cl | H |
| 0953 | | —N=CH—N(CH₃)₂ | H | —OH | —OCH₃ | H |
| 0954 | | —N=CH—N(CH₃)₂ | H | —OCH₃ | H | —OCH₃ |
| 0955 | | —N=CH—N(CH₃)₂ | H | —SCH₃ | H | H |
| 0956 | | —N=CH—N(CH₃)₂ | H | —OCH₃ | H | H |
| 0957 | | —N=CH—N(CH₃)₂ | H | —OCH₃ | —OCH₃ | —OCH₃ |
| 0958 | | —N=CH—N(CH₃)₂ | H | —OH | —OCH₃ | —OCH₃ |
| 0959 | | —N=CH—N(CH₃)₂ | H | H | —SCH₃ | H |
| 0960 | | —N=CH—N(CH₃)₂ | H | H | —OCH₃ | H |
| 0961 | | —N=CH—N(CH₃)₂ | H | —OCH₃ | —OH | H |
| 0962 | | —N=CH—N(CH₃)₂ | —OCH₃ | —CH₃ | H | H |
| 0963 | | —N=CH—N(CH₃)₂ | H | —CH₂—CH₃ | H | H |
| 0964 | | —N=CH—N(CH₃)₂ | —OCH₃ | —CH(CH₃)₂ | H | H |
| 0965 | | —N=CH—N(CH₃)₂ | H | —C₃H₇-n | H | H |
| 0966 | | —N=CH—N(CH₃)₂ | H | —OCH₂—CH₃ | H | H |
| 0967 | | —N=CH—N(CH₃)₂ | H | F | H | H |
| 0968 | | —N=CH—N(CH₃)₂ | H | Cl | H | H |
| 0969 | | —N=CH—N(CH₃)₂ | H | Br | H | H |
| 0970 | | —N=CH—N(CH₃)₂ | H | Cl | Cl | H |
| 0971 | | —N=CH—N(CH₃)₂ | H | OH | OH | OH |
| 0972 | | —N=CH—N(CH₃)₂ | Cl | Cl | H | Cl |
| 0973 | | —N=CH—N(CH₃)₂ | H | —CF₃ | H | H |
| 0974 | | —N=CH—N(CH₃)₂ | H | —OCF₃ | H | H |
| 0975 | | —N=CH—N(CH₃)₂ | H | —C₂F₅ | H | H |

TABLE A-continued

| Comp-No. | R₁ | R₂ | R₃ | R₄ | R₅ | R₆ |
|---|---|---|---|---|---|---|
| 0976 | —N=CH—N(CH₃)₂ | H | H | —C₄H₉-tert | H | H |
| 0977 | —N=CH—N(CH₃)₂ | H | H | —OC₃H₇-i | H | H |
| 0978 | —N=CH—N(CH₃)₂ | H | H | —SO—CH₃ | H | H |
| 0979 | —N=CH—N(CH₃)₂ | H | H | —SO₂—CH₃ | H | H |
| 0980 | —N=CH—N(CH₃)₂ | H | H | —NH—CH₂—CH₃ | H | H |
| 0981 | —N=CH—N(CH₃)₂ | H | H | —O—CH₂—CH=CH₂ | H | H |
| 0982 | —N=CH—N(CH₃)₂ | H | H | —O—CH₂—C≡CH | H | H |
| 0983 | —N=CH—N(CH₃)₂ | H | H | —NH—CH₂—CH₂—NH—CH₃ | H | H |
| 0984 | —N=CH—N(CH₃)₂ | H | H | —SO₂—C₂H₅ | H | H |
| 0985 | —N=CH—N(CH₃)₂ | H | H | —SO₂—CH₃ | Cl | H |
| 0986 | H | H | —OH | H | —OCH₃ | H |
| 0987 | H | H | —OCH₃ | —CH₃ | H | H |
| 0988 | H | H | H | —SO—CH₃ | H | H |
| 0989 | —CO—C₃H₅-cycl | H | H | —CH₂—O—CH₃ | H | H |
| 0990 | —CO—C₃H₅-cycl | H | H | —NH—CO—CH₃ | H | H |
| 0991 | —CO—C₃H₅-cycl | H | H | —CH₂—NH—CO—CH₃ | H | H |
| 0992 | —CO—C₃H₅-cycl | H | H | —CH(CH₃)—NH—CO—CH₃ | H | H |
| 0993 | —CO—C₃H₅-cycl | H | H | —C(CH₃)₂—NH—CO—CH₃ | H | H |
| 0994 | —CO—C₃H₅-cycl | H | H | —CH(CH₃)—O—CH₃ | H | H |
| 0995 | —CO—C₃H₅-cycl | H | H | —C(CH₃)₂—O—CH₃ | H | H |
| 0996 | —CO—C₃H₅-cycl | H | H | —CH(CH₃)—O—CO—CH₃ | H | H |
| 0997 | —CO—C₃H₅-cycl | H | H | —CH₂—O—CO—CH₃ | H | H |
| 0998 | —CO—C₃H₅-cycl | H | H | —C(CH₃)₂—O—CO—CH₃ | H | H |
| 0999 | —CO—C₃H₅-cycl | H | H | —CH₂—CH₂—O—H | H | H |
| 1000 | —CO—C₃H₅-cycl | H | H | —CH₂—CH₂—O—CH₃ | H | H |
| 1001 | —CO—C₃H₅-cycl | H | H | 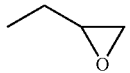 | H | H |
| 1002 | —CO—C₃H₅-cycl | H | H |  | H | H |
| 1003 | —CO—C₃H₅-cycl | H | H |  | H | H |
| 1004 | —CO—C₃H₅-cycl | H | H | 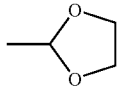 | H | H |
| 1005 | —CO—C₃H₅-cycl | H | H | 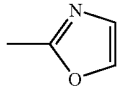 | H | H |
| 1006 | —CO—C₃H₅-cycl | H | H | 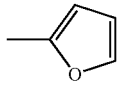 | H | H |
| 1007 | —CO—C₃H₅-cycl | H | H | 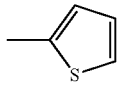 | H | H |
| 1008 | —CO—C₃H₅-cycl | H | H | 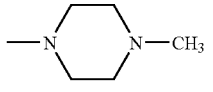 | H | H |
| 1009 | —CO—C₃H₅-cycl | H | H | 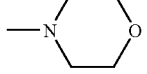 | H | H |

TABLE A-continued

| Comp-No. | $R_1$ | $R_2$ | $R_3$ | $R_4$ | $R_5$ | $R_6$ |
|---|---|---|---|---|---|---|
| 1010 | —CO—$C_3H_5$-cycl | H | H | 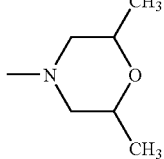 | H | H |
| 1011 | —CO—$C_3H_5$-cycl | H | H | 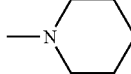 | H | H |
| 1012 | —CO—$C_3H_5$-cycl | H | H | 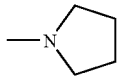 | H | H |
| 1013 | —CO—$C_3H_5$-cycl | H | H | H | H | H |
| 1014 | —CO—$C_3H_5$-cycl | H | H | CN | H | H |
| 1015 | —CO—$C_3H_5$-cycl | H | H | —C($CH_3$)$_2$—OH | H | H |
| 1016 | —CO—$C_3H_5$-cycl | H | H | —$CH_2$—OH | H | H |
| 1017 | —CO—$C_3H_5$-cycl | H | H | —CO—$CH_3$ | H | H |
| 1018 | —CO—$C_3H_5$-cycl | H | H | —C(=NOH)—$CH_3$ | H | H |
| 1019 | —CO—$C_3H_5$-cycl | H | H | —CH(OH)—$CH_3$ | H | H |
| 1020 | —CO—$C_3H_5$-cycl | H | H | (3) —CO—O—$CH_2$— (4) | | H |
| 1021 | —CO—$C_3H_5$-cycl | H | H | —$CH_2$—O—CO—$CH_3$ | H | H |
| 1022 | —CO—$C_3H_5$-cycl | H | H | —C(=NO—$CH_3$)—$CH_3$ | H | H |
| 1023 | —CO—$C_3H_5$-cycl | H | H | —CO—O—$CH_3$ | H | H |
| 1024 | —CO—$C_3H_5$-cycl | H | H | —NH—CO—$C_3H_5$-cycl. | H | H |
| 1025 | —CO—$C_3H_5$-cycl | H | H | —CO—$CH_3$ | Cl | H |
| 1026 | —CO—$C_3H_5$-cycl | H | H | —OH | H | H |
| 1027 | —CO—$C_3H_5$-cycl | H | H | —OH | —$OCH_3$ | H |
| 1028 | —CO—$C_3H_5$-cycl | H | H | —$OCH_3$ | H | —$OCH_3$ |
| 1029 | —CO—$C_3H_5$-cycl | H | H | —$SCH_3$ | H | H |
| 1030 | —CO—$C_3H_5$-cycl | H | H | —$OCH_3$ | H | H |
| 1031 | —CO—$C_3H_5$-cycl | H | H | —$OCH_3$ | —$OCH_3$ | —$OCH_3$ |
| 1032 | —CO—$C_3H_5$-cycl | H | H | —OH | —$OCH_3$ | —$OCH_3$ |
| 1033 | —CO—$C_3H_5$-cycl | H | H | H | —$SCH_3$ | H |
| 1034 | —CO—$C_3H_5$-cycl | H | H | H | —$OCH_3$ | H |
| 1035 | —CO—$C_3H_5$-cycl | H | H | —$OCH_3$ | —OH | H |
| 1036 | —CO—$C_3H_5$-cycl | H | —$OCH_3$ | —$CH_3$ | H | H |
| 1037 | —CO—$C_3H_5$-cycl | H | H | —$CH_2$—$CH_3$ | H | H |
| 1038 | —CO—$C_3H_5$-cycl | H | —$OCH_3$ | —CH($CH_3$)$_2$ | H | H |
| 1039 | —CO—$C_3H_5$-cycl | H | H | —$C_3H_7$-n | H | H |
| 1040 | —CO—$C_3H_5$-cycl | H | H | —$OCH_2$—$CH_3$ | H | H |
| 1041 | —CO—$C_3H_5$-cycl | H | H | F | H | H |
| 1042 | —CO—$C_3H_5$-cycl | H | H | Cl | H | H |
| 1043 | —CO—$C_3H_5$-cycl | H | H | Br | H | H |
| 1044 | —CO—$C_3H_5$-cycl | H | H | Cl | Cl | H |
| 1045 | —CO—$C_3H_5$-cycl | H | H | OH | OH | OH |
| 1046 | —CO—$C_3H_5$-cycl | H | Cl | Cl | H | Cl |
| 1047 | —CO—$C_3H_5$-cycl | H | H | —$CF_3$ | H | H |
| 1048 | —CO—$C_3H_5$-cycl | H | H | —$OCF_3$ | H | H |
| 1049 | —CO—$C_3H_5$-cycl | H | H | —$C_2F_5$ | H | H |
| 1050 | —CO—$C_3H_5$-cycl | H | H | —$C_4H_9$-tert | H | H |
| 1051 | —CO—$C_3H_5$-cycl | H | H | —$OC_3H_7$-i | H | H |
| 1052 | —CO—$C_3H_5$-cycl | H | H | —SO—$CH_3$ | H | H |
| 1053 | —CO—$C_3H_5$-cycl | H | H | —NH—$CH_2$—$CH_3$ | H | H |
| 1054 | —CO—$C_3H_5$-cycl | H | H | —O—$CH_2$—CH=$CH_2$ | H | H |
| 1055 | —CO—$C_3H_5$-cycl | H | H | —O—$CH_2$—C≡CH | H | H |
| 1056 | —CO—$C_3H_5$-cycl | H | H | —NH—$CH_2$—$CH_2$—NH—$CH_3$ | H | H |
| 1057 | —CO—$C_3H_5$-cycl | H | H | —$SO_2$—$C_2H_5$ | H | H |
| 1058 | —CO—$C_3H_5$-cycl | H | H | —$SO_2$—$CH_3$ | Cl | H |
| 1059 | —CO—C($CH_3$)$_2$—$CH_2$—Cl | H | H | —$CH_2$—O—$CH_3$ | H | H |
| 1060 | —CO—C($CH_3$)$_2$—$CH_2$—Cl | H | H | —NH—CO—$CH_3$ | H | H |
| 1061 | —CO—C($CH_3$)$_2$—$CH_2$—Cl | H | H | —$CH_2$—NH—CO—$CH_3$ | H | H |
| 1062 | —CO—C($CH_3$)$_2$—$CH_2$—Cl | H | H | —CH($CH_3$)—NH—CO—$CH_3$ | H | H |
| 1063 | —CO—C($CH_3$)$_2$—$CH_2$—Cl | H | H | —C($CH_3$)$_2$—NH—CO—$CH_3$ | H | H |
| 1064 | —CO—C($CH_3$)$_2$—$CH_2$—Cl | H | H | —CH($CH_3$)—O—$CH_3$ | H | H |
| 1065 | —CO—C($CH_3$)$_2$—$CH_2$—Cl | H | H | —C($CH_3$)$_2$—O—$CH_3$ | H | H |
| 1066 | —CO—C($CH_3$)$_2$—$CH_2$—Cl | H | H | —CH($CH_3$)—O—CO—$CH_3$ | H | H |
| 1067 | —CO—C($CH_3$)$_2$—$CH_2$—Cl | H | H | —$CH_2$—O—CO—$CH_3$ | H | H |
| 1068 | —CO—C($CH_3$)$_2$—$CH_2$—Cl | H | H | —C($CH_3$)$_2$—O—CO—$CH_3$ | H | H |
| 1069 | —CO—C($CH_3$)$_2$—$CH_2$—Cl | H | H | —$CH_2$—$CH_2$—O—H | H | H |

TABLE A-continued

| Comp-No. | R₁ | R₂ | R₃ | R₄ | R₅ | R₆ |
|---|---|---|---|---|---|---|
| 1070 | —CO—C(CH₃)₂—CH₂—Cl | H | H | —CH₂—CH₂—O—CH₃ | H | H |
| 1071 | —CO—C(CH₃)₂—CH₂—Cl | H | H | 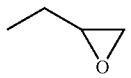 | H | H |
| 1072 | —CO—C(CH₃)₂—CH₂—Cl | H | H |  | H | H |
| 1073 | —CO—C(CH₃)₂—CH₂—Cl | H | H |  | H | H |
| 1074 | —CO—C(CH₃)₂—CH₂—Cl | H | H | 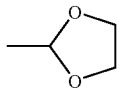 | H | H |
| 1075 | —CO—C(CH₃)₂—CH₂—Cl | H | H | 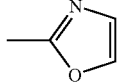 | H | H |
| 1076 | —CO—C(CH₃)₂—CH₂—Cl | H | H | 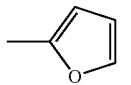 | H | H |
| 1077 | —CO—C(CH₃)₂—CH₂—Cl | H | H | 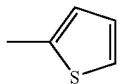 | H | H |
| 1078 | —CO—C(CH₃)₂—CH₂—Cl | H | H | 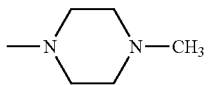 | H | H |
| 1079 | —CO—C(CH₃)₂—CH₂—Cl | H | H | 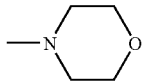 | H | H |
| 1080 | —CO—C(CH₃)₂—CH₂—Cl | H | H | 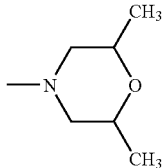 | H | H |
| 1081 | —CO—C(CH₃)₂—CH₂—Cl | H | H | 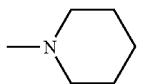 | H | H |
| 1082 | —CO—C(CH₃)₂—CH₂—Cl | H | H | 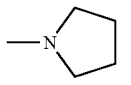 | H | H |
| 1083 | —CO—C(CH₃)₂—CH₂—Cl | H | H | H | H | H |
| 1084 | —CO—C(CH₃)₂—CH₂—Cl | H | H | CN | H | H |
| 1085 | —CO—C(CH₃)₂—CH₂—Cl | H | H | —C(CH₃)₂—OH | H | H |
| 1086 | —CO—C(CH₃)₂—CH₂—Cl | H | H | —CH₂—OH | H | H |
| 1087 | —CO—C(CH₃)₂—CH₂—Cl | H | H | —CO—CH₃ | H | H |
| 1088 | —CO—C(CH₃)₂—CH₂—Cl | H | H | —C(=NOH)—CH₃ | H | H |
| 1089 | —CO—C(CH₃)₂—CH₂—Cl | H | H | —CH(OH)—CH₃ | H | H |
| 1090 | —CO—C(CH₃)₂—CH₂—Cl | H | H | (3) —CO—O—CH₂— (4) | H | H |
| 1091 | —CO—C(CH₃)₂—CH₂—Cl | H | H | —CH₂—O—CO—CH₃ | H | H |
| 1092 | —CO—C(CH₃)₂—CH₂—Cl | H | H | —C(=NO—CH₃)—CH₃ | H | H |
| 1093 | —CO—C(CH₃)₂—CH₂—Cl | H | H | —CO—O—CH₃ | H | H |
| 1094 | —CO—C(CH₃)₂—CH₂—Cl | H | H | —NH—CO—C₃H₅-cycl. | H | H |

TABLE A-continued

| Comp-No. | R₁ | R₂ | R₃ | R₄ | R₅ | R₆ |
|---|---|---|---|---|---|---|
| 1095 | —CO—C(CH₃)₂—CH₂—Cl | H | H | —CO—CH₃ | Cl | H |
| 1096 | —CO—C(CH₃)₂—CH₂—Cl | H | H | —OH | H | H |
| 1097 | —CO—C(CH₃)₂—CH₂—Cl | H | H | —OH | —OCH₃ | H |
| 1098 | —CO—C(CH₃)₂—CH₂—Cl | H | H | —OCH₃ | H | —OCH₃ |
| 1099 | —CO—C(CH₃)₂—CH₂—Cl | H | H | —SCH₃ | H | H |
| 1100 | —CO—C(CH₃)₂—CH₂—Cl | H | H | —OCH₃ | H | H |
| 1101 | —CO—C(CH₃)₂—CH₂—Cl | H | H | —OCH₃ | —OCH₃ | —OCH₃ |
| 1102 | —CO—C(CH₃)₂—CH₂—Cl | H | H | —OH | —OCH₃ | —OCH₃ |
| 1103 | —CO—C(CH₃)₂—CH₂—Cl | H | H | H | —SCH₃ | H |
| 1104 | —CO—C(CH₃)₂—CH₂—Cl | H | H | H | —OCH₃ | H |
| 1105 | —CO—C(CH₃)₂—CH₂—Cl | H | H | —OCH₃ | —OH | H |
| 1106 | —CO—C(CH₃)₂—CH₂—Cl | H | —OCH₃ | —CH₃ | H | H |
| 1107 | —CO—C(CH₃)₂—CH₂—Cl | H | H | —CH₂—CH₃ | H | H |
| 1108 | —CO—C(CH₃)₂—CH₂—Cl | H | —OCH₃ | —CH(CH₃)₂ | H | H |
| 1109 | —CO—C(CH₃)₂—CH₂—Cl | H | H | —C₃H₇-n | H | H |
| 1110 | —CO—C(CH₃)₂—CH₂—Cl | H | H | —OCH₂—CH₃ | H | H |
| 1111 | —CO—C(CH₃)₂—CH₂—Cl | H | H | F | H | H |
| 1112 | —CO—C(CH₃)₂—CH₂—Cl | H | H | Cl | H | H |
| 1113 | —CO—C(CH₃)₂—CH₂—Cl | H | H | Br | H | H |
| 1114 | —CO—C(CH₃)₂—CH₂—Cl | H | H | Cl | Cl | H |
| 1115 | —CO—C(CH₃)₂—CH₂—Cl | H | H | OH | OH | OH |
| 1116 | —CO—C(CH₃)₂—CH₂—Cl | H | Cl | Cl | H | Cl |
| 1117 | —CO—C(CH₃)₂—CH₂—Cl | H | H | —CF₃ | H | H |
| 1118 | —CO—C(CH₃)₂—CH₂—Cl | H | H | —OCF₃ | H | H |
| 1119 | —CO—C(CH₃)₂—CH₂—Cl | H | H | —C₂F₅ | H | H |
| 1120 | —CO—C(CH₃)₂—CH₂—Cl | H | H | —C₄H₉-tert | H | H |
| 1121 | —CO—C(CH₃)₂—CH₂—Cl | H | H | —OC₃H₇-i | H | H |
| 1122 | —CO—C(CH₃)₂—CH₂—Cl | H | H | —SO—CH₃ | H | H |
| 1123 | —CO—C(CH₃)₂—CH₂—Cl | H | H | —SO₂—CH₃ | H | H |
| 1124 | —CO—C(CH₃)₂—CH₂—Cl | H | H | —NH—CH₂—CH₃ | H | H |
| 1125 | —CO—C(CH₃)₂—CH₂—Cl | H | H | —O—CH₂—CH=CH₂ | H | H |
| 1126 | —CO—C(CH₃)₂—CH₂—Cl | H | H | —O—CH₂—C≡CH | H | H |
| 1127 | —CO—C(CH₃)₂—CH₂—Cl | H | H | —NH—CH₂—CH₂—NH—CH₃ | H | H |
| 1128 | —CO—C(CH₃)₂—CH₂—Cl | H | H | —SO₂—C₂H₅ | H | H |
| 1129 | —CO—C(CH₃)₂—CH₂—Cl | H | H | —SO₂—CH₃ | Cl | H |
| 1130 | H | H | H | F | H | H |
| 1131 | CH₃ | H | H | —OCF₃ | H | H |
| 1132 | CH₃ | H | H | —CH₂—CH₂—O—CH₃ | H | H |
| 1133 | CH₃ | CH₃ | H | —SCH₃ | H | H |
| 1134 | —CO—CH₃ | H | H | —SO₂—CH₃ | Cl | H |
| 1135 | —CO—CH(CH₃)—C₂H₅ | H | H | —C(=NOH)—CH₃ | H | H |
| 1136 | —CO—C₃F₇-n | H | H | —OCF₃ | H | H |
| 1137 | —CO—C₂F₅ | H | H | ![2-thienyl] | H | H |
| 1138 | —CO—CF₃ | H | H | —CH₂—CH₃ | H | H |
| 1139 | —CO—C₃H₅-cycl | H | H | —SO₂—CH₃ | H | H |
| 1140 | —N=C(CH₃)—N(CH₃)₂ | | H | —CH(CH₃)—O—CO—CH₃ | H | H |
| 1141 | —N=CH—N(CH₃)₂ | | H | —OH | H | H |
| 1143 | —CO—C(CH₃)₂—CH₂—Cl | H | H | —CH₂—CN | H | H |
| 1144 | —CO—C(CH₃)₂—CH₂—Cl | H | H | —CH—(CH₃)—CN | H | H |
| 1145 | —CO—C(CH₃)₂—CH₂—Cl | H | H | —C(CH₃)₂—CN | H | H |
| 1146 | —CO—C(CH₃)₂—CH₂—Cl | H | H | —CH—(C₂H₅)—CN | H | H |
| 1147 | —CO—C(CH₃)₂—CH₂—Cl | H | H | —C(C₂H₅)₂—CN | H | H |
| 1148 | —CO—C(CH₃)₂—CH₂—Cl | H | H | —CH₂—CH₂—CN | H | H |
| 1149 | —CO—C(CH₃)₂—CH₂—Cl | H | H | —CH(CH₃)—CH₂—CN | H | H |
| 1150 | —CO—C(CH₃)₂—CH₂—Cl | H | H | —CH₂—CO₂—CH₃ | H | H |
| 1151 | —CO—C(CH₃)₂—CH₂—Cl | H | H | —CH(CH₃)—CO₂—CH₃ | H | H |
| 1152 | C₂H₅ | H | H | —CH₂—CN | H | H |
| 1153 | C₂H₅ | H | H | —CH—(CH₃)—CN | H | H |
| 1154 | C₂H₅ | H | H | —C(CH₃)₂—CN | H | H |
| 1155 | C₂H₅ | H | H | —CH—(C₂H₅)—CN | H | H |
| 1156 | C₂H₅ | H | H | —C(C₂H₅)₂—CN | H | H |
| 1157 | C₂H₅ | H | H | —CH₂—CH₂—CN | H | H |
| 1158 | C₂H₅ | H | H | —CH(CH₃)—CH₂—CN | H | H |
| 1159 | C₂H₅ | H | H | —CH₂—CO₂—CH₃ | H | H |
| 1160 | C₂H₅ | H | H | —CH(CH₃)—CO₂—CH₃ | H | H |
| 1161 | CH₃ | H | H | —CH₂—CN | H | H |
| 1162 | CH₃ | H | H | —CH—(CH₃)—CN | H | H |
| 1163 | CH₃ | H | H | —C(CH₃)₂—CN | H | H |
| 1164 | CH₃ | H | H | —CH—(C₂H₅)—CN | H | H |
| 1165 | CH₃ | H | H | —C(C₂H₅)₂—CN | H | H |

TABLE A-continued

| Comp-No. | R₁ | R₂ | R₃ | R₄ | R₅ | R₆ |
|---|---|---|---|---|---|---|
| 1166 | CH₃ | H | H | —CH₂—CH₂—CN | H | H |
| 1167 | CH₃ | H | H | —CH(CH₃)—CH₂—CN | H | H |
| 1168 | CH₃ | H | H | —CH₂—CO₂—CH₃ | H | H |
| 1169 | CH₃ | H | H | —CH(CH₃)—CO₂—CH₃ | H | H |
| 1170 | CH₃ | CH₃ | H | —CH₂—CN | H | H |
| 1171 | CH₃ | CH₃ | H | —CH—(CH₃)—CN | H | H |
| 1172 | CH₃ | CH₃ | H | —C(CH₃)₂—CN | H | H |
| 1173 | CH₃ | CH₃ | H | —CH—(C₂H₅)—CN | H | H |
| 1174 | CH₃ | CH₃ | H | —C(C₂H₅)₂—CN | H | H |
| 1175 | CH₃ | CH₃ | H | —CH₂—CH₂—CN | H | H |
| 1176 | CH₃ | CH₃ | H | —CH(CH₃)—CH₂—CN | H | H |
| 1177 | CH₃ | CH₃ | H | —CH₂—CO₂—CH₃ | H | H |
| 1178 | CH₃ | CH₃ | H | —CH(CH₃)—CO₂—CH₃ | H | H |
| 1179 | —CO—CH₃ | H | H | —CH₂—CN | H | H |
| 1180 | —CO—CH₃ | H | H | —CH—(CH₃)—CN | H | H |
| 1181 | —CO—CH₃ | H | H | —C(CH₃)₂—CN | H | H |
| 1182 | —CO—CH₃ | H | H | —CH—(C₂H₅)—CN | H | H |
| 1183 | —CO—CH₃ | H | H | —C(C₂H₅)₂—CN | H | H |
| 1184 | —CO—CH₃ | H | H | —CH₂—CH₂—CN | H | H |
| 1185 | —CO—CH₃ | H | H | —CH(CH₃)—CH₂—CN | H | H |
| 1186 | —CO—CH₃ | H | H | —CH₂—CO₂—CH₃ | H | H |
| 1187 | —CO—CH₃ | H | H | —CH(CH₃)—CO₂—CH₃ | H | H |
| 1188 | —CO—C₂H₅ | H | H | —CH₂—CN | H | H |
| 1189 | —CO—C₂H₅ | H | H | —CH—(CH₃)—CN | H | H |
| 1190 | —CO—C₂H₅ | H | H | —C(CH₃)₂—CN | H | H |
| 1191 | —CO—C₂H₅ | H | H | —CH—(C₂H₅)—CN | H | H |
| 1192 | —CO—C₂H₅ | H | H | —C(C₂H₅)₂—CN | H | H |
| 1193 | —CO—C₂H₅ | H | H | —CH₂—CH₂—CN | H | H |
| 1194 | —CO—C₂H₅ | H | H | —CH(CH₃)—CH₂—CN | H | H |
| 1195 | —CO—C₂H₅ | H | H | —CH₂—CO₂—CH₃ | H | H |
| 1196 | —CO—C₂H₅ | H | H | —CH(CH₃)—CO₂—CH₃ | H | H |
| 1197 | —CO—CH(CH₃)—C₂H₅ | H | H | —CH₂—CN | H | H |
| 1198 | —CO—CH(CH₃)—C₂H₅ | H | H | —CH—(CH₃)—CN | H | H |
| 1199 | —CO—CH(CH₃)—C₂H₅ | H | H | —C(CH₃)₂—CN | H | H |
| 1200 | —CO—CH(CH₃)—C₂H₅ | H | H | —CH—(C₂H₅)—CN | H | H |
| 1201 | —CO—CH(CH₃)—C₂H₅ | H | H | —C(C2IT5)₂—CN | H | H |
| 1202 | —CO—CH(CH₃)—C₂H₅ | H | H | —CH₂—CH₂—CN | H | H |
| 1203 | —CO—CH(CH₃)—C₂H₅ | H | H | —CH(CH₃)—CH₂—CN | H | H |
| 1204 | —CO—CH(CH₃)—C₂H₅ | H | H | —CH₂—CO₂—CH₃ | H | H |
| 1205 | —CO—CH(CH₃)—C₂H₅ | H | H | —CH(CH₃)—CO₂—CH₃ | H | H |
| 1206 | —CO—C₃F₇-n | H | H | —CH₂—CN | H | H |
| 1207 | —CO—C₃F₇-n | H | H | —CH—(CH₃)—CN | H | H |
| 1208 | —CO—C₃F₇-n | H | H | —C(CH₃)₂—CN | H | H |
| 1209 | —CO—C₃F₇-n | H | H | —CH—(C₂H₅)—CN | H | H |
| 1210 | —CO—C₃F₇-n | H | H | —C(C₂H₅)₂—CN | H | H |
| 1211 | —CO—C₃F₇-n | H | H | —CH₂—CH₂—CN | H | H |
| 1212 | —CO—C₃F₇-n | H | H | —CH(CH₃)—CH₂—CN | H | H |
| 1213 | —CO—C₃F₇-n | H | H | —CH₂—CO₂—CH₃ | H | H |
| 1214 | —CO—C₃F₇-n | H | H | —CH(CH₃)—CO₂—CH₃ | H | H |
| 1215 | —CO—CH₂—O—CO—CH₃ | H | H | —CH₂—CN | H | H |
| 1216 | —CO—CH₂—O—CO—CH₃ | H | H | —CH—(CH₃)—CN | H | H |
| 1217 | —CO—CH₂—O—CO—CH₃ | H | H | —C(CH₃)₂—CN | H | H |
| 1218 | —CO—CH₂—O—CO—CH₃ | H | H | —CH—(C₂H₅)—CN | H | H |
| 1219 | —CO—CH₂—O—CO—CH₃ | H | H | —C(C₂H₅)₂—CN | H | H |
| 1220 | —CO—CH₂—O—CO—CH₃ | H | H | —CH₂—CH₂—CN | H | H |
| 1221 | —CO—CH₂—O—CO—CH₃ | H | H | —CH(CH₃)—CH₂—CN | H | H |
| 1222 | —CO—CH₂—O—CO—CH₃ | H | H | —CH₂—CO₂—CH₃ | H | H |
| 1223 | —CO—CH₂—O—CO—CH₃ | H | H | —CH(CH₃)—CO₂—CH₃ | H | H |
| 1224 | —CO—C₂F₅ | H | H | —CH₂—CN | H | H |
| 1225 | —CO—C₂F₅ | H | H | —CH—(CH₃)—CN | H | H |
| 1226 | —CO—C₂F₅ | H | H | —C(CH₃)₂—CN | H | H |
| 1227 | —CO—C₂F₅ | H | H | —CH—(C₂H₅)—CN | H | H |
| 1228 | —CO—C₂F₅ | H | H | —C(C₂H₅)₂—CN | H | H |
| 1229 | —CO—C₂F₅ | H | H | —CH₂—CH₂—CN | H | H |
| 1230 | —CO—C₂F₅ | H | H | —CH(CH₃)—CH₂—CN | H | H |
| 1231 | —CO—C₂F₅ | H | H | —CH₂—CO₂—CH₃ | H | H |
| 1232 | —CO—C₂F₅ | H | H | —CH(CH₃)—CO₂—CH₃ | H | H |
| 1233 | —CO—CF₃ | H | H | —CH₂—CN | H | H |
| 1234 | —CO—CF₃ | H | H | —CH—(CH₃)—CN | H | H |
| 1235 | —CO—CF₃ | H | H | —C(CH₃)₂—CN | H | H |
| 1236 | —CO—CF₃ | H | H | —CH—(C₂H₅)—CN | H | H |
| 1237 | —CO—CF₃ | H | H | —C(C₂H₅)₂—CN | H | H |
| 1238 | —CO—CF₃ | H | H | —CH₂—CH₂—CN | H | H |
| 1239 | —CO—CF₃ | H | H | —CH(CH₃)—CH₂—CN | H | H |
| 1240 | —CO—CF₃ | H | H | —CH₂—CO₂—CH₃ | H | H |
| 1241 | —CO—CF₃ | H | H | —CH(CH₃)—CO₂—CH₃ | H | H |

TABLE A-continued

| Comp-No. | R$_1$ | R$_2$ | R$_3$ | R$_4$ | R$_5$ | R$_6$ |
|---|---|---|---|---|---|---|
| 1243 | —(CH$_2$)$_4$— | | H | —CH$_2$—CN | H | H |
| 1244 | —(CH$_2$)$_4$— | | H | —CH—(CH$_3$)—CN | H | H |
| 1245 | —(CH$_2$)$_4$— | | H | —C(CH$_3$)$_2$—CN | H | H |
| 1246 | —(CH$_2$)$_4$— | | H | —CH—(C$_2$H$_5$)—CN | H | H |
| 1247 | —(CH$_2$)$_4$— | | H | —C(C$_2$H$_5$)$_2$—CN | H | H |
| 1248 | —(CH$_2$)$_4$— | | H | —CH$_2$—CH$_2$—CN | H | H |
| 1249 | —(CH$_2$)$_4$— | | H | —CH(CH$_3$)—CH$_2$—CN | H | H |
| 1250 | —(CH$_2$)$_4$— | | H | —CH$_2$—CO$_2$—CH$_3$ | H | H |
| 1251 | —(CH$_2$)$_4$— | | H | —CH(CH$_3$)—CO$_2$—CH$_3$ | H | H |
| 1252 | —N=C(CH$_3$)—N(CH$_3$)$_2$ | | H | —CH$_2$—CN | H | H |
| 1253 | —N=C(CH$_3$)—N(CH$_3$)$_2$ | | H | —CH—(CH$_3$)—CN | H | H |
| 1254 | —N=C(CH$_3$)—N(CH$_3$)$_2$ | | H | —C(CH$_3$)$_2$—CN | H | H |
| 1255 | —N=C(CH$_3$)—N(CH$_3$)$_2$ | | H | —CH—(C$_2$H$_5$)—CN | H | H |
| 1256 | —N=C(CH$_3$)—N(CH$_3$)$_2$ | | H | —C(C$_2$H$_5$)$_2$—CN | H | H |
| 1257 | —N=C(CH$_3$)—N(CH$_3$)$_2$ | | H | —CH$_2$—CH$_2$—CN | H | H |
| 1258 | —N=C(CH$_3$)—N(CH$_3$)$_2$ | | H | —CH(CH$_3$)—CH$_2$—CN | H | H |
| 1259 | —N=C(CH$_3$)—N(CH$_3$)$_2$ | | H | —CH$_2$—CO$_2$—CH$_3$ | H | H |
| 1260 | —N=C(CH$_3$)—N(CH$_3$)$_2$ | | H | —CH(CH$_3$)—CO$_2$—CH$_3$ | H | H |
| 1261 | —N=CH—N(CH$_3$)$_2$ | | H | —CH$_2$—CN | H | H |
| 1262 | —N=CH—N(CH$_3$)$_2$ | | H | —CH—(CH$_3$)—CN | H | H |
| 1263 | —N=CH—N(CH$_3$)$_2$ | | H | —C(CH$_3$)$_2$—CN | H | H |
| 1264 | —N=CH—N(CH$_3$)$_2$ | | H | —CH—(C$_2$H$_5$)—CN | H | H |
| 1265 | —N=CH—N(CH$_3$)$_2$ | | H | —C(C$_2$H$_5$)$_2$—CN | H | H |
| 1266 | —N=CH—N(CH$_3$)$_2$ | | H | —CH$_2$—CH$_2$—CN | H | H |
| 1267 | —N=CH—N(CH$_3$)$_2$ | | H | —CH(CH$_3$)—CH$_2$—CN | H | H |
| 1268 | —N=CH—N(CH$_3$)$_2$ | | H | —CH$_2$—CO$_2$—CH$_3$ | H | H |
| 1269 | —N=CH—N(CH$_3$)$_2$ | | H | —CH(CH$_3$)—CO$_2$—CH$_3$ | H | H |
| 1270 | —CO—C$_3$H$_5$-cycl | H | H | —CH$_2$—CN | H | H |
| 1271 | —CO—C$_3$H$_5$-cycl | H | H | —CH—(CH$_3$)—CN | H | H |
| 1272 | —CO—C$_3$H$_5$-cycl | H | H | —C(CH$_3$)$_2$—CN | H | H |
| 1273 | —CO—C$_3$H$_5$-cycl | H | H | —CH—(C$_2$H$_5$)—CN | H | H |
| 1274 | —CO—C$_3$H$_5$-cycl | H | H | —C(C$_2$H$_5$)$_2$—CN | H | H |
| 1275 | —CO—C$_3$H$_5$-cycl | H | H | —CH$_2$—CH$_2$—CN | H | H |
| 1276 | —CO—C$_3$H$_5$-cycl | H | H | —CH(CH$_3$)—CH$_2$—CN | H | H |
| 1277 | —CO—C$_3$H$_5$-cycl | H | H | —CH$_2$—CO$_2$—CH$_3$ | H | H |
| 1278 | —CO—C$_3$H$_5$-cycl | H | H | —CH(CH$_3$)—CO$_2$—CH$_3$ | H | H |
| 1279 | —CH$_2$—CH$_2$—O—CH$_3$ | H | H | —CH$_2$—O—CH$_3$ | H | H |
| 1280 | —CH$_2$—CH$_2$—O—CH$_3$ | H | H | —NH—CO—CH$_3$ | H | H |
| 1281 | —CH$_2$—CH$_2$—O—CH$_3$ | H | H | —CH$_2$—NH—CO—CH$_3$ | H | H |
| 1282 | —CH$_2$—CH$_2$—O—CH$_3$ | H | H | —CH(CH$_3$)—NH—CO—CH$_3$ | H | H |
| 1283 | —CH$_2$—CH$_2$—O—CH$_3$ | H | H | —C(CH$_3$)$_2$—NH—CO—CH$_3$ | H | H |
| 1284 | —CH$_2$—CH$_2$—O—CH$_3$ | H | H | —CH(CH$_3$)—O—CH$_3$ | H | H |
| 1285 | —CH$_2$—CH$_2$—O—CH$_3$ | H | H | —C(CH$_3$)$_2$—O—CH$_3$ | H | H |
| 1286 | —CH$_2$—CH$_2$—O—CH$_3$ | H | H | —CH(CH$_3$)—O—CO—CH$_3$ | H | H |
| 1287 | —CH$_2$—CH$_2$—O—CH$_3$ | H | H | —CH$_2$—O—CO—CH$_3$ | H | H |
| 1288 | —CH$_2$—CH$_2$—O—CH$_3$ | H | H | —C(CH$_3$)$_2$—O—CO—CH$_3$ | H | H |
| 1289 | —CH$_2$—CH$_2$—O—CH$_3$ | H | H | —CH$_2$—CH$_2$—O—H | H | H |
| 1290 | —CH$_2$—CH$_2$—O—CH$_3$ | H | H | —CH$_2$—CH$_2$—O—CH$_3$ | H | H |
| 1291 | —CH$_2$—CH$_2$—O—CH$_3$ | H | H | ![epoxide with ethyl] | H | H |
| 1292 | —CH$_2$—CH$_2$—O—CH$_3$ | H | H | ![epoxide] | H | H |
| 1293 | —CH$_2$—CH$_2$—O—CH$_3$ | H | H | ![methyl epoxide] | H | H |
| 1294 | —CH$_2$—CH$_2$—O—CH$_3$ | H | H | ![2-methyl-1,3-dioxolane] | H | H |
| 1295 | —CH$_2$—CH$_2$—O—CH$_3$ | H | H | ![2-methyl oxazole] | H | H |

TABLE A-continued

| Comp-No. | $R_1$ | $R_2$ | $R_3$ | $R_4$ | $R_5$ | $R_6$ |
|---|---|---|---|---|---|---|
| 1296 | —CH$_2$—CH$_2$—O—CH$_3$ | H | H | 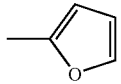 | H | H |
| 1297 | —CH$_2$—CH$_2$—O—CH$_3$ | H | H | 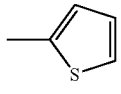 | H | H |
| 1298 | —CH$_2$—CH$_2$—O—CH$_3$ | H | H | 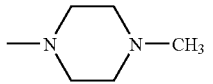 | H | H |
| 1299 | —CH$_2$—CH$_2$—O—CH$_3$ | H | H | 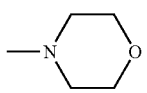 | H | H |
| 1300 | —CH$_2$—CH$_2$—O—CH$_3$ | H | H | 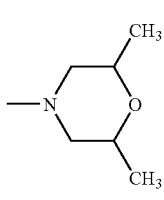 | H | H |
| 1301 | —CH$_2$—CH$_2$—O—CH$_3$ | H | H | 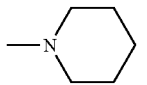 | H | H |
| 1302 | —CH$_2$—CH$_2$—O—CH$_3$ | H | H | 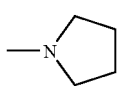 | H | H |
| 1303 | —CH$_2$—CH$_2$—O—CH$_3$ | H | H | H | H | H |
| 1304 | —CH$_2$—CH$_2$—O—CH$_3$ | H | H | CN | H | H |
| 1305 | —CH$_2$—CH$_2$—O—CH$_3$ | H | H | —C(CH$_3$)$_2$—OH | H | H |
| 1306 | —CH$_2$—CH$_2$—O—CH$_3$ | H | H | —CH$_2$—OH | H | H |
| 1307 | —CH$_2$—CH$_2$—O—CH$_3$ | H | H | —CO—CH$_3$ | H | H |
| 1308 | —CH$_2$—CH$_2$—O—CH$_3$ | H | H | —C(=NOH)—CH$_3$ | H | H |
| 1309 | —CH$_2$—CH$_2$—O—CH$_3$ | H | H | —CH(OH)—CH$_3$ | H | H |
| 1310 | —CH$_2$—CH$_2$—O—CH$_3$ | H | H | (3) —CO—O—CH$_2$— (4) | | H |
| 1311 | —CH$_2$—CH$_2$—O—CH$_3$ | H | H | —CH$_2$—O—CO—CH$_3$ | H | H |
| 1312 | —CH$_2$—CH$_2$—O—CH$_3$ | H | H | —C(=NO—CH$_3$)—CH$_3$ | H | H |
| 1313 | —CH$_2$—CH$_2$—O—CH$_3$ | H | H | —CO—O—CH$_3$ | H | H |
| 1314 | —CH$_2$—CH$_2$—O—CH$_3$ | H | H | —NH—CO—C$_3$H$_5$-cycl. | H | H |
| 1315 | —CH$_2$—CH$_2$—O—CH$_3$ | H | H | —CO—CH$_3$ | Cl | H |
| 1316 | —CH$_2$—CH$_2$—O—CH$_3$ | H | H | —OH | H | H |
| 1317 | —CH$_2$—CH$_2$—O—CH$_3$ | H | H | —OH | —OCH$_3$ | H |
| 1318 | —CH$_2$—CH$_2$—O—CH$_3$ | H | H | —OCH$_3$ | H | —OCH$_3$ |
| 1319 | —CH$_2$—CH$_2$—O—CH$_3$ | H | H | —SCH$_3$ | H | H |
| 1320 | —CH$_2$—CH$_2$—O—CH$_3$ | H | H | —OCH$_3$ | H | H |
| 1321 | —CH$_2$—CH$_2$—O—CH$_3$ | H | H | —OCH$_3$ | —OCH$_3$ | —OCH$_3$ |
| 1322 | —CH$_2$—CH$_2$—O—CH$_3$ | H | H | —OH | —OCH$_3$ | —OCH$_3$ |
| 1323 | —CH$_2$—CH$_2$—O—CH$_3$ | H | H | H | —SCH$_3$ | H |
| 1324 | —CH$_2$—CH$_2$—O—CH$_3$ | H | H | H | —OCH$_3$ | H |
| 1325 | —CH$_2$—CH$_2$—O—CH$_3$ | H | H | —OCH$_3$ | —OH | H |
| 1326 | —CH$_2$—CH$_2$—O—CH$_3$ | H | —OCH$_3$ | —CH$_3$ | H | H |
| 1327 | —CH$_2$—CH$_2$—O—CH$_3$ | H | H | H | H | |
| 1328 | —CH$_2$—CH$_2$—O—CH$_3$ | H | —OCH$_3$ | —CH(CH$_3$)$_2$ | H | H |
| 1329 | —CH$_2$—CH$_2$—O—CH$_3$ | H | H | —C$_3$H$_7$-n | H | H |
| 1330 | —CH$_2$—CH$_2$—O—CH$_3$ | H | H | —OCH$_2$—CH$_3$ | H | H |
| 1331 | —CH$_2$—CH$_2$—O—CH$_3$ | H | H | F | H | H |
| 1332 | —CH$_2$—CH$_2$—O—CH$_3$ | H | H | Cl | H | H |
| 1333 | —CH$_2$—CH$_2$—O—CH$_3$ | H | H | Br | H | H |
| 1334 | —CH$_2$—CH$_2$—O—CH$_3$ | H | H | Cl | Cl | H |
| 1335 | —CH$_2$—CH$_2$—O—CH$_3$ | H | H | OH | OH | OH |
| 1336 | —CH$_2$—CH$_2$—O—CH$_3$ | H | Cl | Cl | H | Cl |
| 1337 | —CH$_2$—CH$_2$—O—CH$_3$ | H | H | —CF$_3$ | H | H |
| 1338 | —CH$_2$—CH$_2$—O—CH$_3$ | H | H | —OCF$_3$ | H | H |
| 1339 | —CH$_2$—CH$_2$—O—CH$_3$ | H | H | —C$_2$F$_5$ | H | H |

TABLE A-continued

| Comp-No. | R₁ | R₂ | R₃ | R₄ | R₅ | R₆ |
|---|---|---|---|---|---|---|
| 1340 | —CH₂—CH₂—O—CH₃ | H | H | —C₄H₉-tert | H | H |
| 1341 | —CH₂—CH₂—O—CH₃ | H | H | —OC₃H₇-i | H | H |
| 1343 | —CH₂—CH₂—O—CH₃ | H | H | —SO—CH₃ | H | H |
| 1344 | —CH₂—CH₂—O—CH₃ | H | H | —SO₂—CH₃ | H | H |
| 1345 | —CH₂—CH₂—O—CH₃ | H | H | —NH—CH₂—CH₃ | H | H |
| 1346 | —CH₂—CH₂—O—CH₃ | H | H | —O—CH₂—CH=CH₂ | H | H |
| 1347 | —CH₂—CH₂—O—CH₃ | H | H | —O—CH₂—C≡CH | H | H |
| 1348 | —CH₂—CH₂—O—CH₃ | H | H | —NH—CH₂—CH₂—NH—CH₃ | H | H |
| 1349 | —CH₂—CH₂—O—CH₃ | H | H | —SO₂—C₂H₅ | H | H |
| 1350 | —CH₂—CH₂—O—CH₃ | H | H | —SO₂—CH₃ | Cl | H |
| 1351 | —CH₂—CH₂—O—CH₃ | H | H | —CH₂—CN | H | H |
| 1352 | —CH₂—CH₂—O—CH₃ | H | H | —CH—(CH₃)—CN | H | H |
| 1353 | —CH₂—CH₂—O—CH₃ | H | H | —C(CH₃)₂—CN | H | H |
| 1354 | —CH₂—CH₂—O—CH₃ | H | H | —CH—(C₂H₅)—CN | H | H |
| 1355 | —CH₂—CH₂—O—CH₃ | H | H | —C(C₂H₅)₂—CN | H | H |
| 1356 | —CH₂—CH₂—O—CH₃ | H | H | —CH₂—CH₂—CN | H | H |
| 1357 | —CH₂—CH₂—O—CH₃ | H | H | —CH(CH₃)—CH₂—CN | H | H |
| 1358 | —CH₂—CH₂—O—CH₃ | H | H | —CH₂—CO₂—CH₃ | H | H |
| 1359 | —CH₂—CH₂—O—CH₃ | H | H | —CH(CH₃)—CO₂—CH₃ | H | H |
| 1360 | —CH(CH₃)—CH₂—O—CH₃ | H | H | —CH₂—O—CH₃ | H | H |
| 1361 | —CH(CH₃)—CH₂—O—CH₃ | H | H | —NH—CO—CH₃ | H | H |
| 1362 | —CH(CH₃)—CH₂—O—CH₃ | H | H | —CH₂—NH—CO—CH₃ | H | H |
| 1363 | —CH(CH₃)—CH₂—O—CH₃ | H | H | —CH(CH₃)—NH—CO—CH₃ | H | H |
| 1364 | —CH(CH₃)—CH₂—O—CH₃ | H | H | —C(CH₃)₂—NH—CO—CH₃ | H | H |
| 1365 | —CH(CH₃)—CH₂—O—CH₃ | H | H | —CH(CH₃)—O—CH₃ | H | H |
| 1366 | —CH(CH₃)—CH₂—O—CH₃ | H | H | —C(CH₃)₂—O—CH₃ | H | H |
| 1367 | —CH(CH₃)—CH₂—O—CH₃ | H | H | —CH(CH₃)—O—CO—CH₃ | H | H |
| 1368 | —CH(CH₃)—CH₂—O—CH₃ | H | H | —CH₂—O—CO—CH₃ | H | H |
| 1369 | —CH(CH₃)—CH₂—O—CH₃ | H | H | —C(CH₃)₂—O—CO—CH₃ | H | H |
| 1370 | —CH(CH₃)—CH₂—O—CH₃ | H | H | —CH₂—CH₂—O—H | H | H |
| 1371 | —CH(CH₃)—CH₂—O—CH₃ | H | H | —CH₂—CH₂—O—CH₃ | H | H |
| 1372 | —CH(CH₃)—CH₂—O—CH₃ | H | H | —CH₂-(oxiranyl) | H | H |
| 1373 | —CH(CH₃)—CH₂—O—CH₃ | H | H | oxiranyl | H | H |
| 1374 | —CH(CH₃)—CH₂—O—CH₃ | H | H | 2-methyloxiranyl | H | H |
| 1375 | —CH(CH₃)—CH₂—O—CH₃ | H | H | 1,3-dioxolan-2-yl | H | H |
| 1376 | —CH(CH₃)—CH₂—O—CH₃ | H | H | oxazol-2-yl | H | H |
| 1377 | —CH(CH₃)—CH₂—O—CH₃ | H | H | furan-2-yl | H | H |
| 1378 | —CH(CH₃)—CH₂—O—CH₃ | H | H | thiophen-2-yl | H | H |
| 1379 | —CH(CH₃)—CH₂—O—CH₃ | H | H | 4-methylpiperazin-1-yl | H | H |
| 1380 | —CH(CH₃)—CH₂—O—CH₃ | H | H | morpholin-4-yl | H | H |

TABLE A-continued

| Comp-No. | R₁ | R₂ | R₃ | R₄ | R₅ | R₆ |
|---|---|---|---|---|---|---|
| 1381 | —CH(CH₃)—CH₂—O—CH₃ | H | H | 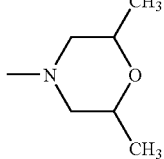 | H | H |
| 1382 | —CH(CH₃)—CH₂—O—CH₃ | H | H | 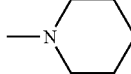 | H | H |
| 1383 | —CH(CH₃)—CH₂—O—CH₃ | H | H | 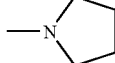 | H | H |
| 1384 | —CH(CH₃)—CH₂—O—CH₃ | H | H | H | H | H |
| 1385 | —CH(CH₃)—CH₂—O—CH₃ | H | H | CN | H | H |
| 1386 | —CH(CH₃)—CH₂—O—CH₃ | H | H | —C(CH₃)₂—OH | H | H |
| 1387 | —CH(CH₃)—CH₂—O—CH₃ | H | H | —CH₂—OH | H | H |
| 1388 | —CH(CH₃)—CH₂—O—CH₃ | H | H | —CO—CH₃ | H | H |
| 1389 | —CH(CH₃)—CH₂—O—CH₃ | H | H | —C(=NOH)—CH₃ | H | H |
| 1390 | —CH(CH₃)—CH₂—O—CH₃ | H | H | —CH(OH)—CH₃ | H | H |
| 1391 | —CH(CH₃)—CH₂—O—CH₃ | H | H | (3) —CO—O—CH₂— (4) | | H |
| 1392 | —CH(CH₃)—CH₂—O—CH₃ | H | H | —CH₂—O—CO—CH₃ | H | H |
| 1393 | —CH(CH₃)—CH₂—O—CH₃ | H | H | —C(=NO—CH₃)—CH₃ | H | H |
| 1394 | —CH(CH₃)—CH₂—O—CH₃ | H | H | —CO—O—CH₃ | H | H |
| 1395 | —CH(CH₃)—CH₂—O—CH₃ | H | H | —NH—CO—C₃H₅-cycl. | H | H |
| 1396 | —CH(CH₃)—CH₂—O—CH₃ | H | H | —CO—CH₃ | Cl | H |
| 1397 | —CH(CH₃)—CH₂—O—CH₃ | H | H | —OH | H | H |
| 1398 | —CH(CH₃)—CH₂—O—CH₃ | H | H | —OH | —OCH₃ | H |
| 1399 | —CH(CH₃)—CH₂—O—CH₃ | H | H | —OCH₃ | H | —OCH₃ |
| 1400 | —CH(CH₃)—CH₂—O—CH₃ | H | H | —SCH₃ | H | H |
| 1401 | —CH(CH₃)—CH₂—O—CH₃ | H | H | —OCH₃ | H | H |
| 1402 | —CH(CH₃)—CH₂—O—CH₃ | H | H | —OCH₃ | —OCH₃ | —OCH₃ |
| 1403 | —CH(CH₃)—CH₂—O—CH₃ | H | H | —OH | —OCH₃ | —OCH₃ |
| 1404 | —CH(CH₃)—CH₂—O—CH₃ | H | H | H | —SCH₃ | H |
| 1405 | —CH(CH₃)—CH₂—O—CH₃ | H | H | H | —OCH₃ | H |
| 1406 | —CH(CH₃)—CH₂—O—CH₃ | H | H | —OCH₃ | —OH | H |
| 1407 | —CH(CH₃)—CH₂—O—CH₃ | H | —OCH₃ | —CH₃ | H | H |
| 1408 | —CH(CH₃)—CH₂—O—CH₃ | H | H | —CH₂—CH₃ | H | H |
| 1409 | —CH(CH₃)—CH₂—O—CH₃ | H | —OCH₃ | —CH(CH₃)₂ | H | H |
| 1410 | —CH(CH₃)—CH₂—O—CH₃ | H | H | —C₃H₇-n | H | H |
| 1411 | —CH(CH₃)—CH₂—O—CH₃ | H | H | —OCH₂—CH₃ | H | H |
| 1412 | —CH(CH₃)—CH₂—O—CH₃ | H | H | F | H | H |
| 1413 | —CH(CH₃)—CH₂—O—CH₃ | H | H | Cl | H | H |
| 1414 | —CH(CH₃)—CH₂—O—CH₃ | H | H | Br | H | H |
| 1415 | —CH(CH₃)—CH₂—O—CH₃ | H | H | Cl | Cl | H |
| 1416 | —CH(CH₃)—CH₂—O—CH₃ | H | H | OH | OH | OH |
| 1417 | —CH(CH₃)—CH₂—O—CH₃ | H | Cl | Cl | H | Cl |
| 1418 | —CH(CH₃)—CH₂—O—CH₃ | H | H | —CF₃ | H | H |
| 1419 | —CH(CH₃)—CH₂—O—CH₃ | H | H | —OCF₃ | H | H |
| 1420 | —CH(CH₃)—CH₂—O—CH₃ | H | H | —C₂F₅ | H | H |
| 1421 | —CH(CH₃)—CH₂—O—CH₃ | H | H | —C₄H₉-tert | H | H |
| 1422 | —CH(CH₃)—CH₂—O—CH₃ | H | H | —OC₃H₇-i | H | H |
| 1423 | —CH(CH₃)—CH₂—O—CH₃ | H | H | —SO—CH₃ | H | H |
| 1424 | —CH(CH₃)—CH₂—O—CH₃ | H | H | —SO₂—CH₃ | H | H |
| 1425 | —CH(CH₃)—CH₂—O—CH₃ | H | H | —NH—CH₂—CH₃ | H | H |
| 1426 | —CH(CH₃)—CH₂—O—CH₃ | H | H | —O—CH₂—CH=CH₂ | H | H |
| 1427 | —CH(CH₃)—CH₂—O—CH₃ | H | H | —O—CH₂—C≡CH | H | H |
| 1428 | —CH(CH₃)—CH₂—O—CH₃ | H | H | —NH—CH₂—CH₂—NH—CH₃ | H | H |
| 1429 | —CH(CH₃)—CH₂—O—CH₃ | H | H | —SO₂—C₂H₅ | H | H |
| 1430 | —CH(CH₃)—CH₂—O—CH₃ | H | H | —SO₂—CH₃ | Cl | H |
| 1431 | —CH(CH₃)—CH₂—O—CH₃ | H | H | —CH₂—CN | H | H |
| 1432 | —CH(CH₃)—CH₂—O—CH₃ | H | H | —CH—(CH₃)—CN | H | H |
| 1433 | —CH(CH₃)—CH₂—O—CH₃ | H | H | —C(CH₃)₂—CN | H | H |
| 1434 | —CH(CH₃)—CH₂—O—CH₃ | H | H | —CH—(C₂H₅)—CN | H | H |
| 1435 | —CH(CH₃)—CH₂—O—CH₃ | H | H | —C(C₂H₅)₂—CN | H | H |
| 1436 | —CH(CH₃)—CH₂—O—CH₃ | H | H | —CH₂—CH₂—CN | H | H |
| 1437 | —CH(CH₃)—CH₂—O—CH₃ | H | H | —CH(CH₃)—CH₂—CN | H | H |
| 1438 | —CH(CH₃)—CH₂—O—CH₃ | H | H | —CH₂—CO₂—CH₃ | H | H |
| 1439 | —CH(CH₃)—CH₂—O—CH₃ | H | H | —CH(CH₃)—CO₂—CH₃ | H | H |
| 1440 | —CH₂—CH₂—O—CH₂—CH₂— | H | H | —CH₂—O—CH₃ | H | H |

TABLE A-continued

| Comp-No. | R₁ | R₂ | R₃ | R₄ | R₅ | R₆ |
|---|---|---|---|---|---|---|
| 1441 | | —CH₂—CH₂—O—CH₂—CH₂— | H | —NH—CO—CH₃ | H | H |
| 1443 | | —CH₂—CH₂—O—CH₂—CH₂— | H | —CH₂—NH—CO—CH₃ | H | H |
| 1444 | | —CH₂—CH₂—O—CH₂—CH₂— | H | —CH(CH₃)—NH—CO—CH₃ | H | H |
| 1445 | | —CH₂—CH₂—O—CH₂—CH₂— | H | —C(CH₃)₂—NH—CO—CH₃ | H | H |
| 1446 | | —CH₂—CH₂—O—CH₂—CH₂— | H | —CH(CH₃)—O—CH₃ | H | H |
| 1447 | | —CH₂—CH₂—O—CH₂—CH₂— | H | —C(CH₃)₂—O—CH₃ | H | H |
| 1448 | | —CH₂—CH₂—O—CH₂—CH₂— | H | —CH(CH₃)—O—CO—CH₃ | H | H |
| 1449 | | —CH₂—CH₂—O—CH₂—CH₂— | H | —CH₂—O—CO—CH₃ | H | H |
| 1450 | | —CH₂—CH₂—O—CH₂—CH₂— | H | —C(CH₃)₂—O—CO—CH₃ | H | H |
| 1451 | | —CH₂—CH₂—O—CH₂—CH₂— | H | —CH₂—CH₂—O—H | H | H |
| 1452 | | —CH₂—CH₂—O—CH₂—CH₂— | H | —CH₂—CH₂—O—CH₃ | H | H |
| 1453 | | —CH₂—CH₂—O—CH₂—CH₂— | H | 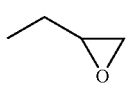 | H | H |
| 1454 | | —CH₂—CH₂—O—CH₂—CH₂— | H |  | H | H |
| 1455 | | —CH₂—CH₂—O—CH₂—CH₂— | H |  | H | H |
| 1456 | | —CH₂—CH₂—O—CH₂—CH₂— | H | 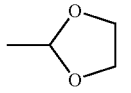 | H | H |
| 1457 | | —CH₂—CH₂—O—CH₂—CH₂— | H | 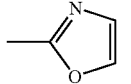 | H | H |
| 1458 | | —CH₂—CH₂—O—CH₂—CH₂— | H | 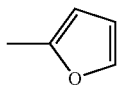 | H | H |
| 1459 | | —CH₂—CH₂—O—CH₂—CH₂— | H | 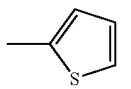 | H | H |
| 1460 | | —CH₂—CH₂—O—CH₂—CH₂— | H | 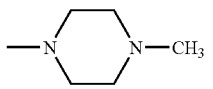 | H | H |
| 1461 | | —CH₂—CH₂—O—CH₂—CH₂— | H |  | H | H |
| 1462 | | —CH₂—CH₂—O—CH₂—CH₂— | H | 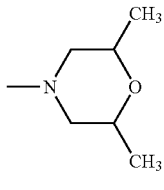 | H | H |
| 1463 | | —CH₂—CH₂—O—CH₂—CH₂— | H | 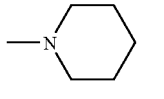 | H | H |
| 1464 | | —CH₂—CH₂—O—CH₂—CH₂— | H | 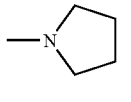 | H | H |
| 1465 | | —CH₂—CH₂—O—CH₂—CH₂— | H | H | H | H |
| 1466 | | —CH₂—CH₂—O—CH₂—CH₂— | H | CN | H | H |

TABLE A-continued

| Comp-No. | R₁ | R₂ | R₃ | R₄ | R₅ | R₆ |
|---|---|---|---|---|---|---|
| 1467 | | —CH₂—CH₂—O—CH₂—CH₂— | H | —C(CH₃)₂—OH | H | H |
| 1468 | | —CH₂—CH₂—O—CH₂—CH₂— | H | —CH₂—OH | H | H |
| 1469 | | —CH₂—CH₂—O—CH₂—CH₂— | H | —CO—CH₃ | H | H |
| 1470 | | —CH₂—CH₂—O—CH₂—CH₂— | H | —C(=NOH)—CH₃ | H | H |
| 1471 | | —CH₂—CH₂—O—CH₂—CH₂— | H | —CH(OH)—CH₃ | H | H |
| 1472 | | —CH₂—CH₂—O—CH₂—CH₂— | H | (3) —CO—O—CH₂— (4) | | H |
| 1473 | | —CH₂—CH₂—O—CH₂—CH₂— | H | —CH₂—O—CO—CH₃ | H | H |
| 1474 | | —CH₂—CH₂—O—CH₂—CH₂— | H | —C(=NO—CH₃)—CH₃ | H | H |
| 1475 | | —CH₂—CH₂—O—CH₂—CH₂— | H | —CO—O—CH₃ | H | H |
| 1476 | | —CH₂—CH₂—O—CH₂—CH₂— | H | —NH—CO—C₃H₅-cycl. | H | H |
| 1477 | | —CH₂—CH₂—O—CH₂—CH₂— | H | —CO—CH₃ | Cl | H |
| 1478 | | —CH₂—CH₂—O—CH₂—CH₂— | H | —OH | H | H |
| 1479 | | —CH₂—CH₂—O—CH₂—CH₂— | H | —OH | —OCH₃ | H |
| 1480 | | —CH₂—CH₂—O—CH₂—CH₂— | H | —OCH₃ | H | —OCH₃ |
| 1481 | | —CH₂—CH₂—O—CH₂—CH₂— | H | —SCH₃ | H | H |
| 1482 | | —CH₂—CH₂—O—CH₂—CH₂— | H | —OCH₃ | H | H |
| 1483 | | —CH₂—CH₂—O—CH₂—CH₂— | H | —OCH₃ | —OCH₃ | —OCH₃ |
| 1484 | | —CH₂—CH₂—O—CH₂—CH₂— | H | —OH | —OCH₃ | —OCH₃ |
| 1485 | | —CH₂—CH₂—O—CH₂—CH₂— | H | H | —SCH₃ | H |
| 1486 | | —CH₂—CH₂—O—CH₂—CH₂— | H | H | —OCH₃ | H |
| 1487 | | —CH₂—CH₂—O—CH₂—CH₂— | H | —OCH₃ | —OH | H |
| 1488 | | —CH₂—CH₂—O—CH₂—CH₂— | —OCH₃ | —CH₃ | H | H |
| 1489 | | —CH₂—CH₂—O—CH₂—CH₂— | H | —CH₂—CH₃ | H | H |
| 1490 | | —CH₂—CH₂—O—CH₂—CH₂— | —OCH₃ | —CH(CH₃)₂ | H | H |
| 1491 | | —CH₂—CH₂—O—CH₂—CH₂— | H | —C₃H₇-n | H | H |
| 1492 | | —CH₂—CH₂—O—CH₂—CH₂— | H | —OCH₂—CH₃ | H | H |
| 1493 | | —CH₂—CH₂—O—CH₂—CH₂— | H | F | H | H |
| 1494 | | —CH₂—CH₂—O—CH₂—CH₂— | H | Cl | H | H |
| 1495 | | —CH₂—CH₂—O—CH₂—CH₂— | H | Br | H | H |
| 1496 | | —CH₂—CH₂—O—CH₂—CH₂— | H | Cl | Cl | H |
| 1497 | | —CH₂—CH₂—O—CH₂—CH₂— | H | OH | OH | OH |
| 1498 | | —CH₂—CH₂—O—CH₂—CH₂— | Cl | Cl | H | Cl |
| 1499 | | —CH₂—CH₂—O—CH₂—CH₂— | H | —CF₃ | H | H |
| 1500 | | —CH₂—CH₂—O—CH₂—CH₂— | H | —OCF₃ | H | H |
| 1501 | | —CH₂—CH₂—O—CH₂—CH₂— | H | —C₂F₅ | H | H |
| 1502 | | —CH₂—CH₂—O—CH₂—CH₂— | H | —C₄H₉-tert | H | H |
| 1503 | | —CH₂—CH₂—O—CH₂—CH₂— | H | —OC₃H₇-i | H | H |
| 1504 | | —CH₂—CH₂—O—CH₂—CH₂— | H | —SO—CH₃ | H | H |
| 1505 | | —CH₂—CH₂—O—CH₂—CH₂— | H | —SO₂—CH₃ | H | H |
| 1506 | | —CH₂—CH₂—O—CH₂—CH₂— | H | —NH—CH₂—CH₃ | H | H |
| 1507 | | —CH₂—CH₂—O—CH₂—CH₂— | H | —O—CH₂—CH=CH₂ | H | H |
| 1508 | | —CH₂—CH₂—O—CH₂—CH₂— | H | —O—CH₂—C≡CH | H | H |
| 1509 | | —CH₂—CH₂—O—CH₂—CH₂— | H | —NH—CH₂—CH₂—NH—CH₃ | H | H |
| 1510 | | —CH₂—CH₂—O—CH₂—CH₂— | H | —SO₂—C₂H₅ | H | H |
| 1511 | | —CH₂—CH₂—O—CH₂—CH₂— | H | —SO₂—CH₃ | Cl | H |
| 1512 | | —CH₂—CH₂—O—CH₂—CH₂— | H | —CH₂—CN | H | H |
| 1513 | | —CH₂—CH₂—O—CH₂—CH₂— | H | —CH—(CH₃)—CN | H | H |
| 1514 | | —CH₂—CH₂—O—CH₂—CH₂— | H | —C(CH₃)₂—CN | H | H |
| 1515 | | —CH₂—CH₂—O—CH₂—CH₂— | H | —CH—(C₂H₅)—CN | H | H |
| 1516 | | —CH₂—CH₂—O—CH₂—CH₂— | H | —C(C₂H₅)₂—CN | H | H |
| 1517 | | —CH₂—CH₂—O—CH₂—CH₂— | H | —CH₂—CH₂—CN | H | H |
| 1518 | | —CH₂—CH₂—O—CH₂—CH₂— | H | —CH(CH₃)—CH₂—CN | H | H |
| 1519 | | —CH₂—CH₂—O—CH₂—CH₂— | H | —CH₂—CO₂—CH₃ | H | H |
| 1520 | | —CH₂—CH₂—O—CH₂—CH₂— | H | —CH(CH₃)—CO₂—CH₃ | H | H |
| 1521 | | —CH₂—CH₂—N(CH₃)—CH₂—CH₂— | H | —CH₂—O—CH₃ | H | H |
| 1522 | | —CH₂—CH₂—N(CH₃)—CH₂—CH₂— | H | —NH—CO—CH₃ | H | H |
| 1523 | | —CH₂—CH₂—N(CH₃)—CH₂—CH₂— | H | —CH₂—NH—CO—CH₃ | H | H |
| 1524 | | —CH₂—CH₂—N(CH₃)—CH₂—CH₂— | H | —CH(CH₃)—NH—CO—CH₃ | H | H |
| 1525 | | —CH₂—CH₂—N(CH₃)—CH₂—CH₂— | H | —C(CH₃)₂—NH—CO—CH₃ | H | H |
| 1526 | | —CH₂—CH₂—N(CH₃)—CH₂—CH₂— | H | —CH(CH₃)—O—CH₃ | H | H |
| 1527 | | —CH₂—CH₂—N(CH₃)—CH₂—CH₂— | H | —C(CH₃)₂—O—CH₃ | H | H |
| 1528 | | —CH₂—CH₂—N(CH₃)—CH₂—CH₂— | H | —CH(CH₃)—O—CO—CH₃ | H | H |
| 1529 | | —CH₂—CH₂—N(CH₃)—CH₂—CH₂— | H | —CH₂—O—CO—CH₃ | H | H |
| 1530 | | —CH₂—CH₂—N(CH₃)—CH₂—CH₂— | H | —C(CH₃)₂—O—CO—CH₃ | H | H |
| 1531 | | —CH₂—CH₂—N(CH₃)—CH₂—CH₂— | H | —CH₂—CH₂—O—H | H | H |
| 1532 | | —CH₂—CH₂—N(CH₃)—CH₂—CH₂— | H | —CH₂—CH₂—O—CH₃ | H | H |
| 1533 | | —CH₂—CH₂—N(CH₃)—CH₂—CH₂— | H | oxiranyl | H | H |
| 1534 | | —CH₂—CH₂—N(CH₃)—CH₂—CH₂— | H | oxiranyl | H | H |

TABLE A-continued

| Comp-No. | R₁ | R₃ | R₄ | R₅ | R₆ |
|---|---|---|---|---|---|
| 1535 | —CH₂—CH₂—N(CH₃)—CH₂—CH₂— | H |  | H | H |
| 1536 | —CH₂—CH₂—N(CH₃)—CH₂—CH₂— | H | 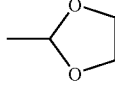 | H | H |
| 1537 | —CH₂—CH₂—N(CH₃)—CH₂—CH₂— | H | 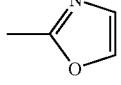 | H | H |
| 1538 | —CH₂—CH₂—N(CH₃)—CH₂—CH₂— | H | 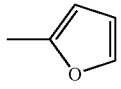 | H | H |
| 1539 | —CH₂—CH₂—N(CH₃)—CH₂—CH₂— | H | 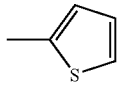 | H | H |
| 1540 | —CH₂—CH₂—N(CH₃)—CH₂—CH₂— | H | 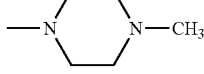 | H | H |
| 1541 | —CH₂—CH₂—N(CH₃)—CH₂—CH₂— | H | 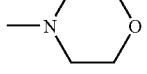 | H | H |
| 1543 | —CH₂—CH₂—N(CH₃)—CH₂—CH₂— | H | 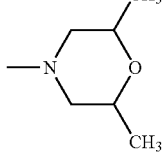 | H | H |
| 1544 | —CH₂—CH₂—N(CH₃)—CH₂—CH₂— | H | 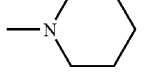 | H | H |
| 1545 | —CH₂—CH₂—N(CH₃)—CH₂—CH₂— | H | 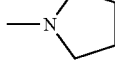 | H | H |
| 1546 | —CH₂—CH₂—N(CH₃)—CH₂—CH₂— | H | H | H | H |
| 1547 | —CH₂—CH₂—N(CH₃)—CH₂—CH₂— | H | CN | H | H |
| 1548 | —CH₂—CH₂—N(CH₃)—CH₂—CH₂— | H | —C(CH₃)₂—OH | H | H |
| 1549 | —CH₂—CH₂—N(CH₃)—CH₂—CH₂— | H | —CH₂—OH | H | H |
| 1550 | —CH₂—CH₂—N(CH₃)—CH₂—CH₂— | H | —CO—CH₃ | H | H |
| 1551 | —CH₂—CH₂—N(CH₃)—CH₂—CH₂— | H | —C(=NOH)—CH₃ | H | H |
| 1552 | —CH₂—CH₂—N(CH₃)—CH₂—CH₂— | H | —CH(OH)—CH₃ | H | H |
| 1553 | —CH₂—CH₂—N(CH₃)—CH₂—CH₂— | H | (3) —CO—O—CH₂— (4) | | H |
| 1554 | —CH₂—CH₂—N(CH₃)—CH₂—CH₂— | H | —CH₂—O—CO—CH₃ | H | H |
| 1555 | —CH₂—CH₂—N(CH₃)—CH₂—CH₂— | H | —C(=NO—CH₃)—CH₃ | H | H |
| 1556 | —CH₂—CH₂—N(CH₃)—CH₂—CH₂— | H | —CO—O—CH₃ | H | H |
| 1557 | —CH₂—CH₂—N(CH₃)—CH₂—CH₂— | H | —NH—CO—C₃H₅-cycl. | H | H |
| 1558 | —CH₂—CH₂—N(CH₃)—CH₂—CH₂— | H | —CO—CH₃ | Cl | H |
| 1559 | —CH₂—CH₂—N(CH₃)—CH₂—CH₂— | H | —OH | H | H |
| 1560 | —CH₂—CH₂—N(CH₃)—CH₂—CH₂— | H | —OH | —OCH₃ | H |
| 1561 | —CH₂—CH₂—N(CH₃)—CH₂—CH₂— | H | —OCH₃ | H | —OCH₃ |
| 1562 | —CH₂—CH₂—N(CH₃)—CH₂—CH₂— | H | —SCH₃ | H | H |
| 1563 | —CH₂—CH₂—N(CH₃)—CH₂—CH₂— | H | —OCH₃ | H | H |
| 1564 | —CH₂—CH₂—N(CH₃)—CH₂—CH₂— | H | —OCH₃ | —OCH₃ | —OCH₃ |
| 1565 | —CH₂—CH₂—N(CH₃)—CH₂—CH₂— | H | —OH | —OCH₃ | —OCH₃ |
| 1566 | —CH₂—CH₂—N(CH₃)—CH₂—CH₂— | H | H | —SCH₃ | H |
| 1567 | —CH₂—CH₂—N(CH₃)—CH₂—CH₂— | H | H | —OCH₃ | H |

TABLE A-continued

| Comp-No. | R$_1$ | R$_2$ | R$_3$ | R$_4$ | R$_5$ | R$_6$ |
|---|---|---|---|---|---|---|
| 1568 | —CH$_2$—CH$_2$—N(CH$_3$)—CH$_2$—CH$_2$— | H | —OCH$_3$ | —OH | H |
| 1569 | —CH$_2$—CH$_2$—N(CH$_3$)—CH$_2$—CH$_2$— | —OCH$_3$ | —CH$_3$ | H | H |
| 1570 | —CH$_2$—CH$_2$—N(CH$_3$)—CH$_2$—CH$_2$— | H | —CH$_2$—CH$_3$ | H | H |
| 1571 | —CH$_2$—CH$_2$—N(CH$_3$)—CH$_2$—CH$_2$— | —OCH$_3$ | —CH(CH$_3$)$_2$ | H | H |
| 1572 | —CH$_2$—CH$_2$—N(CH$_3$)—CH$_2$—CH$_2$— | H | —C$_3$H$_7$-n | H | H |
| 1573 | —CH$_2$—CH$_2$—N(CH$_3$)—CH$_2$—CH$_2$— | H | —OCH$_2$—CH$_3$ | H | H |
| 1574 | —CH$_2$—CH$_2$—N(CH$_3$)—CH$_2$—CH$_2$— | H | F | H | H |
| 1575 | —CH$_2$—CH$_2$—N(CH$_3$)—CH$_2$—CH$_2$— | H | Cl | H | H |
| 1576 | —CH$_2$—CH$_2$—N(CH$_3$)—CH$_2$—CH$_2$— | H | Br | H | H |
| 1577 | —CH$_2$—CH$_2$—N(CH$_3$)—CH$_2$—CH$_2$— | H | Cl | Cl | H |
| 1578 | —CH$_2$—CH$_2$—N(CH$_3$)—CH$_2$—CH$_2$— | H | OH | OH | OH |
| 1579 | —CH$_2$—CH$_2$—N(CH$_3$)—CH$_2$—CH$_2$— | Cl | Cl | H | Cl |
| 1580 | —CH$_2$—CH$_2$—N(CH$_3$)—CH$_2$—CH$_2$— | H | —CF$_3$ | H | H |
| 1581 | —CH$_2$—CH$_2$—N(CH$_3$)—CH$_2$—CH$_2$— | H | —OCF$_3$ | H | H |
| 1582 | —CH$_2$—CH$_2$—N(CH$_3$)—CH$_2$—CH$_2$— | H | —C$_2$F$_5$ | H | H |
| 1583 | —CH$_2$—CH$_2$—N(CH$_3$)—CH$_2$—CH$_2$— | H | —C$_4$H$_9$-tert | H | H |
| 1584 | —CH$_2$—CH$_2$—N(CH$_3$)—CH$_2$—CH$_2$— | H | —OC$_3$H$_7$-i | H | H |
| 1585 | —CH$_2$—CH$_2$—N(CH$_3$)—CH$_2$—CH$_2$— | H | —SO—CH$_3$ | H | H |
| 1586 | —CH$_2$—CH$_2$—N(CH$_3$)—CH$_2$—CH$_2$— | H | —SO$_2$—CH$_3$ | H | H |
| 1587 | —CH$_2$—CH$_2$—N(CH$_3$)—CH$_2$—CH$_2$— | H | —NH—CH$_2$—CH$_3$ | H | H |
| 1588 | —CH$_2$—CH$_2$—N(CH$_3$)—CH$_2$—CH$_2$— | H | —O—CH$_2$—CH=CH$_2$ | H | H |
| 1589 | —CH$_2$—CH$_2$—N(CH$_3$)—CH$_2$—CH$_2$— | H | —O—CH$_2$—C≡CH | H | H |
| 1590 | —CH$_2$—CH$_2$—N(CH$_3$)—CH$_2$—CH$_2$— | H | —NH—CH$_2$—CH$_2$—NH—CH$_3$ | H | H |
| 1591 | —CH$_2$—CH$_2$—N(CH$_3$)—CH$_2$—CH$_2$— | H | —SO$_2$—C$_2$H$_5$ | H | H |
| 1592 | —CH$_2$—CH$_2$—N(CH$_3$)—CH$_2$—CH$_2$— | H | —SO$_2$—CH$_3$ | Cl | H |
| 1593 | —CH$_2$—CH$_2$—N(CH$_3$)—CH$_2$—CH$_2$— | H | —CH$_2$—CN | H | H |
| 1594 | —CH$_2$—CH$_2$—N(CH$_3$)—CH$_2$—CH$_2$— | H | —CH—(CH$_3$)—CN | H | H |
| 1595 | —CH$_2$—CH$_2$—N(CH$_3$)—CH$_2$—CH$_2$— | H | —C(CH$_3$)$_2$—CN | H | H |
| 1596 | —CH$_2$—CH$_2$—N(CH$_3$)—CH$_2$—CH$_2$— | H | —CH—(C$_2$H$_5$)—CN | H | H |
| 1597 | —CH$_2$—CH$_2$—N(CH$_3$)—CH$_2$—CH$_2$— | H | —C(C$_2$H$_5$)$_2$—CN | H | H |
| 1598 | —CH$_2$—CH$_2$—N(CH$_3$)—CH$_2$—CH$_2$— | H | —CH$_2$—CH$_2$—CN | H | H |
| 1599 | —CH$_2$—CH$_2$—N(CH$_3$)—CH$_2$—CH$_2$— | H | —CH(CH$_3$)—CH$_2$—CN | H | H |
| 1600 | —CH$_2$—CH$_2$—N(CH$_3$)—CH$_2$—CH$_2$— | H | —CH$_2$—CO$_2$—CH$_3$ | H | H |
| 1601 | —CH$_2$—CH$_2$—N(CH$_3$)—CH$_2$—CH$_2$— | H | —CH(CH$_3$)—CO$_2$—CH$_3$ | H | H |

For the following example compounds physico-chemical data have been obtained and are displayed in order to illustrate the working of the present invention, including the outlined methods of synthesis. The number of given data may not be interpreted as a limitation of the invention.

TABLE B

| Comp. No. | Melting point [OC] or 1H-NMR [δ in ppm] |
|---|---|
| 01.0025 | 244–245 |
| 01.0026 | 260–261 |
| 01.0027 | 219–220 |
| 01.0028 | 214–215 |
| 01.0029 | 228–229 |
| 01.0030 | >260 |
| 01.0031 | 216–217 |
| 01.0032 | >260 |
| 01.0034 | 237–238 |
| 01.0035 | 223–225 |
| 01.0038 | 133–234 |
| 01.0039 | 244–245 |
| 01.0042 | 115–117 |
| 01.0052 | 243–245 |
| 01.0169 | 244–245 |
| 01.0307 | >260 |
| 01.0315 | 235–236 |
| 01.0377 | >260 |
| 01.0448 | 188–189 |
| 01.0588 | 255–256 |
| 01.0658 | 206–207 |
| 01.0729 | >260 |
| 01.0869 | 196–197 |
| 01.0940 | 230 |
| 01.1013 | >260 |
| 01.1083 | 178–179 |

TABLE B-continued

| Comp. No. | Melting point [OC] or 1H-NMR [δ in ppm] |
|---|---|
| 01.1465 | 233–234 |
| 01.1546 | 239–240 |
| 02.0026 | 236–238 |
| 02.0027 | 252–253 |
| 02.0028 | >260 |
| 02.0031 | 260–261 |
| 02.0038 | 256–258 |
| 02.0041 | 238–240 |
| 02.0042 | 223–225 |
| 02.0052 | 208–210 |
| 02.0054 | >260 |
| 02.0058 | >260 |
| 02.0059 | >260 |
| 02.0061 | 239–240 |
| 02.0063 | 222–223 |
| 02.0123 | >260 |
| 02.0124 | >260 |
| 02.0193 | >260 |
| 02.1130 | 259–260 |
| 03.0025 | >260 |
| 03.0026 | >260 |
| 03.0029 | 255–256 |
| 03.0035 | 241.242 |
| 03.0236 | 224.227 |
| 03.0242 | 88–91 |
| 04.0035 | 236–237 |
| 06.0025 | >260 |
| 06.0026 | >260 |
| 06.0029 | >260 |
| 06.0035 | 249–250 |
| 07.0025 | 212–213 |
| 07.0026 | 234–235 |

TABLE B-continued

| Comp. No. | Melting point [OC] or 1H-NMR [δ in ppm] |
|---|---|
| 07.0029 | 198–200 |
| 10.0029 | 228–229 |
| 10.0518 | 90–92 |

In the following, examples of test systems in plant protection are provided which can demonstrate the efficiency of the compounds of the formula I (designated as "active ingredient" or "test compounds"):

Biological Examples

Example B-1

Effect Against *Puccinia graminis* on Wheat (Brownrust on Wheat)

a) Residual Protective Activity 1 week old wheat plants cv. Arina are treated with the formulated test-compound (0.02% active substance) in a spray chamber. Two days after application wheat plants are inoculated by spraying a spore suspension ($1 \times 10^5$ ureidospores/ml) on the test plants. After an incubation period of 1 day at +20° C. and 95% relative atmospheric humidity (r. h.) plants are kept for 9 days at +20° C. and 60% r.h. in a greenhouse. The disease incidence is assessed 10 days after inoculation.

Compounds of Tables 1 to 10 show good activity in this test.

b) Systemic Activity

An aqueous spray liquor prepared from the formulated test compound (0.002% active substance, based on the volume of soil) is poured onto wheat plants 5 days after sowing. Care is taken that the spray liquor does not come into contact with the above-ground parts of the plant. 48 hours later, the plants are inoculated with a spore suspension of the fungus. After an incubation period of 48 hours (95 to 100% r.h. at +20° C.), the plants are placed in a greenhouse at +20° C. 12 days after infection, the disease incidence is evaluated.

Compounds of Tables 1 to 10 show good activity in this test.

Example B-2

Effect Against *Phytophthora infestans* on Tomatoes (Late Blight on Potato)

a) Residual Protective Activity 3 week old tomato plants cv. Roter Gnom are treated with the formulated test compound (0.02% active substance) in a spray chamber. Two day after application the plants are inoculated by spraying a sporangia suspension ($2 \times 10^4$ sporangia/ml) on the test plants. After an incubation period of 4 days at +18° C. and 95% r.h. in a growth chamber the disease incidence is assessed.

Compounds of Tables 1 to 10 show good activity in this test.

At the indicated concentration compounds 01.0025, 01.0028, 01.0031, 01.0307, 01.0315, 01.0729, 02.0027, 02.0028, 02.0031, 02.0038, 10.0029, and 10.0518 exhibited over 70% control of the fungal infection in this test.

b) Systemic Activity

An aqueous suspension prepared from the formulated test compound (0.002% active substance, based on the volume of soil) is poured onto tomato plants which have been cultivated for three weeks. Care is taken that the spray liquor does not come into contact with the above-ground parts of the plant. 48 hours later, the plants are inoculated with a sporangia suspension of the fungus. Evaluation of the disease incidence takes place 5 days after infection, during which period conditions of 90 to 100% r.h. and +20° C. are maintained.

Compounds of Tables 1 to 10 show good activity in this test.

At the indicated concentration compounds 01.0025, 01.0028, 01.0031, 01.0307, 01.0315, 01.0729, 02.0027, 02.0028, 02.0031, 02.0038, 10.0029, and 10.0518 exhibited over 70% control of the fungal infection in this test.

Example B-3

Effect Against *Phytophthora infestans*/Potato (Late Blight on Potato)

5 week old potato plants cv. Bintje are treated with the formulated test compound (0.02% active substance) in a spray chamber. Two days after application the plants are inoculated by spraying a sporangia suspension ($1.4 \times 10^5$ sporangia/ml) on the test plants. After an incubation period of 4 days at +18° C. and 95% r. h. in a growth chamber the disease incidence is assessed.

Compounds of Tables 1 to 10 show good activity in this test.

At the indicated concentration compounds 01.0025, 01.0028, 01.0031, 01.0307, 01.0315, 01.0729, 02.0027, 02.0028, 02.0031, 02.0038, 10.0029, and 10.0518 exhibited over 70% control of the fungal infection in this test.

Example B-4

Effect Against *Plasmopara viticola* on Grapevine (Grape Downy Mildew)

5 week old grape seedlings cv. Gutedel are treated with the formulated test compound (0.02% active substance) in a spray chamber. One day after application grape plants are inoculated by spraying a sporangia suspension ($4 \times 10^4$ sporangia/ml) on the lower leaf side of the test plants. After an incubation period of 6 days at +22° C. and 95% r. h. in a greenhouse the disease incidence is assessed.

Compounds of Tables 1 to 10 show good activity in this test.

At the indicated concentration compounds 01.0025, 01.0027, 01.0028, 01.0030, 01.0031, 01.0034, 01.0042, 01.0169, 01.0658, 01.0729, 01.0869, 02.0027, 02.0028, 02.0031, 02.0038, 10.0029 and 10.0518 exhibited over 70% control of the fungal infection in this test.

Example B-5

Residual Protective Activity Against *Venturia inaequalis* on Apples (Scab on Apple)

4 week old apple seedlings cv. McIntosh are treated with the formulated test compound (0.02% active substance) in a spray chamber. One day after application apple plants are inoculated by spraying a spore suspension (4×10⁵ conidia/ml) on the test plants. After an incubation period of 4 days at +21° C. and 95% r. h. the plants are placed for 4 days at +21° C. and 60% r. h. in a greenhouse. After another 4 day incubation period at +21° C. and 95% r. h. the disease incidence is assessed.

Compounds of Tables 1 to 10 show good activity in this test.

Example B-6

Effect Against *Erysiphe graminis* on Barley
(Powdery Mildew on Barley)

a) Residual Protective Activity

Barley plants of approximately 8 cm height are sprayed to drip point with an aqueous spray liquor prepared from wettable powder of the active ingredient (0.02% active substance), and dusted 3 to 4 hours later with conidia of the fungus. The infected plants are placed in a greenhouse at +22° C. 12 days after infection, the fungal attack is evaluated.

Compounds of Tables 1 to 10 show good activity in this test.

b) Systemic Activity

An aqueous spray liquor prepared from the formulated test compound (0.002% active substance, based on the volume of soil) is poured onto barley plants of approximately 8 cm height. Care is taken that the spray liquor does not come into contact with the above-ground parts of the plant. 48 hours later, the plants are dusted with conidia of the fungus. The infected plants are placed in a greenhouse at +22° C. 12 days after infection, the disease incidence is evaluated.

Compounds of Tables 1 to 10 show good activity in this test.

Example B-7

*Botrytis cinerea*/Grape (*botrytis* on Grapes)

5 week old grape seedlings cv. Gutedel are treated with the formulated test compound (0.02% active substance) in a spray chamber. Two days after application grape plants are inoculated by spraying a spore suspension (1×10⁶ conidia/ml) on the test plants. After an incubation period of 4 days at +21° C. and 95% r. h. in a greenhouse the disease incidence is assessed.

Compounds of Tables 1 to 10 show good activity in this test.

At the indicated concentration compound 01.0042 exhibited over 70% control of the fungal infection in this test.

Example B-8

Effect Against *Botrytis cinerea*/Tomato (*botrytis* on Tomatoes)

4 week old tomato plants cv. Roter Gnom are treated with the formulated test compound 0.02% active substance) in a spray chamber. Two days after application tomato plants are inoculated by spraying a spore suspension (1×10⁵ conidia/ml) on the test plants. After an incubation period of 4 days at +20° C. and 95% r. h. in a greenhouse the disease incidence is assessed.

Compounds of Tables 1 to 10 show good activity in this test.

At the indicated concentration compound 01.0042 exhibited over 70% control of the fungal infection in this test.

Example B-9

Effect Against *Pyricularia oryzae*/Rice (Rice Blast)

3 week old rice plants cv. Sasanishiki are treated with the formulated test compound (0.02% active substance) in a spray chamber. Two days after application rice plants are inoculated by spraying a spore suspension (1×10⁵ conidia/ml) on the test plants. After an incubation period of 6 days at +25° C. and 95% r. h. the disease incidence is assessed.

Compounds of Tables 1 to 10 show good activity in this test.

Example B-10

Effect Against *Pyrenophora teres*
(*Helminthosporium*)/Barley (Net Blotch on Barley)

1 week old barley plants cv. Regina are treated with a formulated test compound (0.02% active substance) in a spray chamber. Two days after application barley plants are inoculated by spraying a spore suspension (3×10⁴ conidia/ml) on the test plants. After an incubation period of 2 days at +20° C. and 95% r.h. plants are kept for 2 days at +20° C. and 60% r.h. in a greenhouse. The disease incidence is assessed 4 days after inoculation.

Compounds of Tables 1 to 10 show good activity in this test.

At the indicated concentration compound 01.0028 exhibited over 70% control of the fungal infection in this test.

Example B-11

Effect Against *Fusarium culmorum*/Wheat
(*Fusarium* Head Blight on Wheat)

A conidia suspension of *F. culmorum* (7×10⁵ conidia/ml) is mixed with the formulated test compound (0.002% active substance). The mixture is applied into a pouch which has been equipped before with a filter paper. After the application wheat seeds (cv. Orestis) are sown into the upper fault of the filter paper. The prepared pouches are then incubated for 11 days at approx. +10° C. to +18° C. and a relative humidity of 100% with a light period of 14 hours. The evaluation is made by assessing the degree of disease occurrence in the form of brown lesions on the roots.

Compounds of Tables 1 to 10 show good activity in this test.

Example B-12

Effect Against *Septoria nodorum*/Wheat (*Septoria* Leaf Spot on Wheat)

1 week old wheat plants cv. Arina are treated with a formulated test compound (0.02% active substance) in a spray chamber. One day after application wheat plants are inoculated by spraying a spore suspension (5×10⁵ conidia/ml) on the test plants. After an incubation period of 1 day at +20° C. and 95% r.h. plants are kept for 10 days at +20° C. and 60% r.h. in a greenhouse. The disease incidence is assessed 11 days after inoculation. Compounds of Tables 1 to 10 show good activity in this test.

The invention claimed is:

1. A compound of formula IA

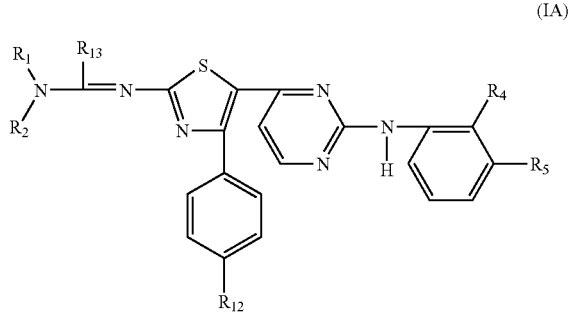

wherein $R_4$ is hydrogen, cyano, hydroxy, $C_1$–$C_4$alkoxy, $C_1$–$C_6$aminoalkyl, $C_1$–$C_8$alkanoyloxy-$C_1$–$C_4$alkyl, $C_1$–$C_8$alkanoylamino-$C_1$–$C_4$alkyl, $C_1$–$C_4$alkoxy-$C_1$–$C_6$alkyl, $C_1$–$C_6$hydroxyalkyl or $C_1$–$C_4$cyanoalkyl; $R_5$ is hydrogen, hydroxy, halogen, $C_1$–$C_6$alkyl, $C_1$–$C_6$alkoxy or $C_1$–$C_6$haloalkyl; $R_9$ is hydrogen, $C_1$–$C_6$alkyl, $C_1$–$C_6$haloalkyl, $C_3$–$C_7$cycloalkyl, $C_3$–$C_7$cycloalkyl-$C_1$–$C_4$alkyl, $C_1$–$C_4$alkyl-$C_3$–$C_7$cycloalkyl-$C_1$–$C_4$alkyl, aryl, aryl-$C_1$–$C_4$alkyl, heteroaryl or heteroaryl-$C_1$–$C_4$alkyl; $R_{10}$ is $C_1$–$C_6$alkyl, $C_1$–$C_6$haloalkyl, $C_3$–$C_7$cycloalkyl-$C_1$–$C_4$alkyl or $C_1$–$C_4$alkoxy-$C_1$–$C_6$alkyl; $R_{11}$ is $C_1$–$C_6$alkyl, $C_3$–$C_7$cycloalkyl, $C_3$–$C_7$cycloalkyl-$C_1$–$C_4$alkyl, $C_1$–$C_4$alkoxy-$C_1$–$C_6$alkyl, aryl or heteroaryl; and $R_{12}$ is halogen, $C_1$–$C_4$alkyl, $C_1$–$C_4$alkoxy, $C_1$–$C_4$haloalkyl or $C_1$–$C_4$haloalkoxy.

2. A method of controlling and preventing an infestation of crop plants by phytopathogenic microorganisms, which comprises the application of a compound of formula I

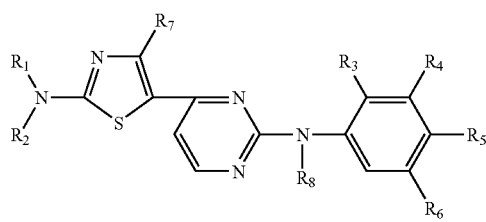

wherein
$R_1$ is hydrogen, $C_1$–$C_6$alkyl, $C_2$–$C_6$alkenyl, $C_3$–$C_7$cycloalkyl, $C_3$–$C_7$cycloalkyl-$C_1$–$C_4$alkyl, $C_1$–$C_4$alkyl-$C_3$–$C_7$cycloalkyl-$C_1$–$C_4$alkyl, $C_1$–$C_6$haloalkyl, $C_1$–$C_6$hydroxyalkyl, $C_1$–$C_4$alkoxy-$C_1$–$C_6$alkyl, $C_1$–$C_6$aminoalkyl, $C_1$–$C_4$alkyl-$C_1$–$C_6$aminoalkyl, di($C_1$–$C_4$alkyl)-$C_1$–$C_6$aminoalkyl, aryl-$C_1$–$C_4$alkyl, heteroaryl-$C_1$–$C_4$alkyl, or a group —CO—$R_9$, —CO—O$R_{10}$, —CO—N$R_{10}R_{11}$, or —N$R_{10}R_{11}$;
$R_2$ is hydrogen, $C_1$–$C_6$alkyl, $C_1$–$C_6$haloalkyl, $C_1$–$C_6$hydroxyalkyl, $C_1$–$C_4$alkoxy-$C_1$–$C_6$alkyl, $C_1$–$C_6$aminoalkyl, $C_1$–$C_4$alkyl-$C_1$–$C_6$aminoalkyl or a group —CO—$R_9$; or
$R_1$ and $R_2$ together with the nitrogen to which they are bound form an optionally substituted N-linked saturated or unsaturated N-ring system which may contain oxygen or sulfur as a ring member, or form a group —N=C$R_9$—N$R_{10}R_{11}$;
$R_3$ is hydrogen, halogen or $C_1$–$C_4$alkyl;
$R_4$ is hydrogen, $C_1$–$C_6$alkyl, $C_1$–$C_6$haloalkyl, $C_1$–$C_6$cyanoalkyl, $C_3$–$C_7$cycloalkyl, $C_2$–$C_6$alkenyl, $C_2$–$C_6$haloalkenyl, $C_2$–$C_6$alkynyl, $C_2$–$C_6$haloalkynyl, amino, $C_1$–$C_6$alkylamino, di($C_1$–$C_4$alkyl)-amino, halogen, hydroxy, mercapto, cyano, $C_1$–$C_6$alkoxy, $C_2$–$C_6$alkenyloxy, $C_2$–$C_6$alkynyloxy, $C_1$–$C_6$haloalkoxy, $C_1$–$C_8$alkanoyloxy-$C_1$–$C_6$alkyl, $C_1$–$C_6$alkylthio, $C_1$–$C_6$alkylsulfinyl, $C_1$–$C_6$akylsulfonyl, $C_1$–$C_6$hydroxyalkyl, $C_1$–$C_4$alkoxy-$C_1$–$C_6$alkyl, $C_1$–$C_6$aminoalkyl, $C_1$–$C_4$alkyl-$C_1$–$C_6$aminoalkyl, di($C_1$–$C_4$alkyl)-$C_1$–$C_6$aminoalkyl, $C_1$–$C_8$alkoxycarbonyl, $C_1$–$C_8$alkanoyl-$C_1$–$C_6$aminoalkyl, optionally substituted heterocyclyl, optionally substituted aryl, optionally substituted heteroaryl, or a group —CO—$R_9$, —O—CO—$R_9$, —NH—CO—$R_9$, —($C_1$–$C_6$alkylene-)-CO—$R_9$, —C(—O—$C_1$–$C_6$alkylene-O—)—$R_9$, —C(=NO$R_8$)—$R_9$ or —CO—N$R_{10}R_{11}$;
$R_5$ is hydrogen, hydroxy, halogen, $C_1$–$C_6$alkyl, $C_1$–$C_6$alkoxy or $C_1$–$C_6$haloalkyl;
$R_6$ is hydrogen, $C_1$–$C_6$alkyl or $C_1$–$C_6$haloalkyl;
$R_7$ is thienyl, pyridinyl or aryl each optionally substituted with one to three substituents independently selected from the group comprising halogen, $C_1$–$C_4$alkyl, $C_1$–$C_4$alkoxy, $C_1$–$C_4$haloalkyl and $C_1$–$C_4$haloalkoxy;
$R_8$ is hydrogen, $C_1$–$C_6$alkyl, $C_2$–$C_6$alkenyl, $C_2$–$C_6$alkynyl, $C_1$–$C_4$alkoxy-$C_1$–$C_6$alkyl, or a group —CO—$R_9$ or —CO—O$R_{10}$;
$R_9$ is hydrogen, $C_1$–$C_6$alkyl, $C_1$–$C_6$haloalkyl, $C_3$–$C_7$cycloalkyl, $C_3$–$C_7$cycloalkyl-$C_1$–$C_4$alkyl, aryl, $C_1$–$C_4$alkyl-$C_3$–$C_7$cycloalkyl-$C_1$–$C_4$alkyl, aryl-$C_1$–$C_4$alkyl, heteroaryl or heteroaryl-$C_1$–$C_4$alkyl;
$R_{10}$ is $C_1$–$C_6$alkyl, $C_1$–$C_6$haloalkyl, $C_3$–$C_7$cycloalkyl-$C_1$–$C_4$alkyl or $C_1$–$C_4$alkoxy-$C_1$–$C_6$alkyl;
$R_{11}$ is $C_1$–$C_6$alkyl, $C_3$–$C_7$cycloalkyl, $C_3$–$C_7$cycloalkyl-$C_1$–$C_4$alkyl, $C_1$–$C_4$alkoxy-$C_1$–$C_6$alkyl, aryl or heteroaryl; or a salt thereof to the plant, to parts of plants or to the locus thereof.

3. A method according to claim 1, wherein $R_3$, $R_6$ and $R_8$ are all hydrogen.

4. A method according to claim 1, wherein $R_1$ is hydrogen, $C_1$–$C_4$alkyl, or is a group —CO—$R_9$; and $R_2$ is hydrogen or $C_1$–$C_4$alkyl; or $R_1$ and $R_2$ together form the group —N=C$R_9$—N$R_{10}R_{11}$; $R_3$ is hydrogen or methyl; and $R_4$ is hydrogen, hydroxy, amino, $C_1$–$C_4$alkyl, $C_1$–$C_4$haloalkyl, $C_1$–$C_4$cyanoalkyl, $C_1$–$C_6$alkylamino, di($C_1$–$C_4$alkyl)-amino, $C_1$–$C_6$aminoalkyl, halogen, mercapto, cyano, $C_1$–$C_6$alkoxy, $C_2$–$C_6$alkenyloxy, $C_2$–$C_6$alkynyloxy, $C_1$–$C_6$alkylthio, $C_1$–$C_6$alkylsulfinyl, $C_1$–$C_6$alkylsulfonyl, $C_1$–$C_6$hydroxyalkyl, $C_1$–$C_4$alkoxy-$C_1$–$C_6$alkyl, $C_1$–$C_4$alkyl-$C_1$–$C_6$aminoalkyl, di($C_1$–$C_4$alkyl)-$C_1$–$C_6$aminoalkyl, $C_1$–$C_4$alkoxycarbonyl; —CO—$R_9$, or —NH—CO—$R_9$; and $R_5$ is hydrogen, hydroxy, or methoxy; and $R_6$ is hydrogen; and $R_7$ is 4-pyridyl or optionally substituted aryl carrying one to three substituents independently selected from the group comprising halogen, $C_1$–$C_4$alkyl, $C_1$–$C_4$alkoxy, $C_1$–$C_4$haloalkyl and $C_1$–$C_4$haloalkoxy; and $R_8$ is hydrogen, $C_1$–$C_4$alkanoyl, $C_1$–$C_4$haloalkanoyl or $C_1$–$C_4$alkyl.

5. A method according to claim 1, wherein; $R_1$ is hydrogen, methyl, trifluoroacetyl, pentafluoropropionyl or heptafluorobutyryl; and $R_2$ is hydrogen or $C_1$–$C_4$alkyl; or $R_1$ and $R_2$ are both hydrogen, or $R_1$ and $R_2$ together form the groups —N=CH—N(CH$_3$)$_2$ or —N=C(CH$_3$)—N(CH$_3$)$_2$; and $R_3$ is hydrogen or methyl; and $R_4$ is hydrogen, hydroxy, $C_1$–$C_4$alkyl, $C_1$–$C_4$alkoxy, $C_1$–$C_4$haloalkoxy, $C_1$–$C_4$haloalkyl, $C_1$–$C_4$cyanoalkyl, $C_1$–$C_4$alkanoyloxy, $C_1$–$C_4$hydroxyalkyl, $C_1$–$C_4$haloalkanoyloxy, $C_1$–$C_4$alkanoyl-$C_1$–$C_6$aminoalkyl, $C_1$–$C_4$alkanoyloxy-$C_1$–$C_4$alkyl, $C_1$–$C_4$alkanoyl, $C_1$–$C_4$alkylthio or $C_1$–$C_4$alkoxycarbonyl; and $R_5$ is hydrogen or hydroxy; and $R_6$ is hydrogen; and $R_7$ is phenyl or halophenyl; and $R_8$ is hydrogen or $C_1$–$C_4$fluoroalkanoyl.

6. A method according to claim 1, wherein; $R_1$ is acetyl; and $R_2$ is hydrogen or methyl; or $R_1$ and $R_2$ together form the groups —N=CH—N(CH$_3$)$_2$ or —N=C(CH$_3$)—N(CH$_3$)$_2$; and $R_3$ is hydrogen; and $R_4$ is hydrogen, hydroxy, cyano, fluorine, chlorine, bromine, methyl, tert. butyl, methylthio, trifluoromethyl, hydroxymethyl, cyanomethyl, 2-cyanoethyl, 1-hydroxyethyl, 2-hydroxyisopropyl, acetyl, acetoxymethyl, methoxycarbonyl, methoxy, ethoxy or trifluoromethoxy; and $R_5$ and $R_6$ are hydrogen; and $R_7$ is phenyl, 4-fluorophenyl or 4-chlorophenyl; and $R_8$ is hydrogen or $C_1$–$C_4$fluoroalkanoyl.

7. A method according to claim 1, wherein $R_1$, $R_2$, $R_3$, $R_5$, $R_6$ and $R_8$ are all hydrogen and $R_4$ is hydrogen, hydroxy, cyano, fluorine, chlorine, bromine, methyl, tert.butyl, methylthio, trifluoromethyl, cyanomethyl, 2-cyanoethyl, hydroxymethyl, 1-hydroxyethyl, 2-hydroxyisopropyl, acetyl, acetoxymethyl, and $R_7$ is phenyl, 4-fluorophenyl or 4-chlorophenyl.

8. A method according to claim 1, wherein the compound of formula I is a compound of subformula IA

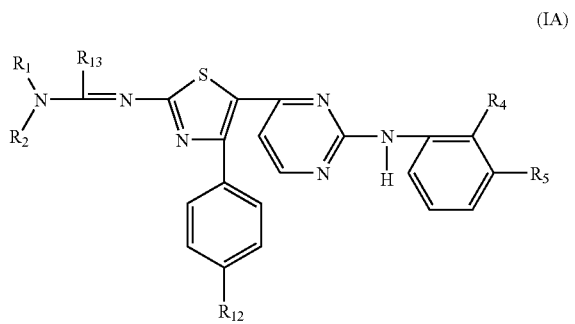

(IA)

wherein $R_4$ is hydrogen, cyano, hydroxy, $C_1$–$C_4$alkoxy, $C_1$–$C_6$aminoalkyl, $C_1$–$C_8$alkanoyloxy-$C_1$–$C_4$alkyl, $C_1$–$C_8$alkanoylamino-$C_1$–$C_4$alkyl, $C_1$–$C_4$alkoxy-$C_1$–$C_6$alkyl, $C_1$–$C_6$hydroxyalkyl or $C_1$–$C_4$cyanoalkyl; $R_5$ is hydrogen, hydroxy, halogen, $C_1$–$C_6$alkyl, $C_1$–$C_6$alkoxy or $C_1$–$C_6$haloalkyl; $R_9$ is hydrogen, $C_1$–$C_6$alkyl, $C_1$–$C_6$haloalkyl, $C_3$–$C_7$cycloalkyl, $C_3$–$C_7$cycloalkyl-$C_1$–$C_4$alkyl, $C_1$–$C_4$alkyl-$C_3$–$C_7$cycloalkyl-$C_1$–$C_4$alkyl, aryl, aryl-$C_1$–$C_4$alkyl, heteroaryl or heteroaryl-$C_1$–$C_4$alkyl; $R_{10}$ is $C_1$–$C_6$alkyl, $C_1$–$C_6$haloalkyl, $C_3$–$C_7$cycloalkyl-$C_1$–$C_4$alkyl or $C_1$–$C_4$alkoxy-$C_1$–$C_6$alkyl; $R_{11}$ is $C_1$–$C_6$alkyl, $C_3$–$C_7$cycloalkyl, $C_3$–$C_7$cycloalkyl-$C_1$–$C_4$alkyl, $C_1$–$C_4$alkoxy-$C_1$–$C_6$alkyl, aryl or heteroaryl; and $R_{12}$ is halogen, $C_1$–$C_4$alkyl, $C_1$–$C_4$alkoxy, $C_1$–$C_4$haloalkyl or $C_1$–$C_4$haloalkoxy.

9. A method according to claim 1, wherein the compound of formula I is a compound of subformula IB

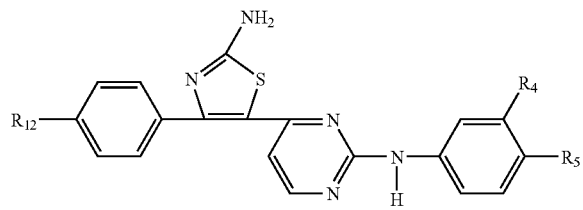

(IB)

wherein $R_4$ is hydrogen, hydroxy, cyano, $C_1$–$C_4$alkoxy, $C_1$–$C_6$aminoalkyl, $C_1$–$C_8$alkanoyloxy-$C_1$–$C_4$alkyl, $C_1$–$C_8$alkanoylamino-$C_1$–$C_4$alkyl, $C_1$–$C_4$alkoxy-$C_1$–$C_6$alkyl, $C_1$–$C_6$hydroxyalkyl or $C_1$–$C_4$cyanoalkyl, and $R_{12}$ is halogen, $C_1$–$C_4$alkyl, $C_1$–$C_4$alkoxy, $C_1$–$C_4$haloalkyl and $C_1$–$C_4$haloalkoxy.

10. A method according to claim 1, wherein the compound of formula I is selected from the group consisting of:
N-[4-(2-amino-4-phenyl-thiazol-5-yl)-pyrimidin-2-yl]-N-phenyl-amine,
N-{4-[2-amino-4-(4-fluoro-phenyl)-thiazol-5-yl]-pyrimidin-2-yl}-N-phenyl-amine;
N-[4-(2-amino-4-phenyl-thiazol-5-yl)-pyrimidin-2-yl]-N-[3-(1-hydroxyethyl)-phenyl]-amine;
N-{4-[2-amino-4-(4-fluoro-phenyl)-thiazol-5-yl]-pyrimidin-2-yl}-N-[3-(1-hydroxyethyl)-phenyl]-amine;
N-[4-(2-amino-4-phenyl-thiazol-5-yl)-pyrimidin-2-yl]-N-[3-(1-hydroxy-1-methylethyl)-phenyl]-amine;
N-{4-[2-amino-4-(4-fluoro-phenyl)-thiazol-5-yl]-pyrimidin-2-yl}-N-[3-(1-hydroxy-1-methylethyl)-phenyl]-amine;
N-[4-(2-amino-4-phenyl, thiazol-5-yl)-pyrimidin-2-yl]-N-(3-acetyl-phenyl)-amine;
N-{4-[2-amino-4-(4-fluoro-phenyl)-thiazol-5-yl]-pyrimidin-2-yl}-N-(3-acetyl-phenyl)-amine;
N-[4-(2-amino-4-thiazol-5-yl)-pyrimidin-2-yl]-N-(3-cyano-phenyl)-amine;
N-{4-[2-amino-4-(4-fluoro-phenyl)-thiazol-5-yl]-pyrimidin-2-yl}-(3-cyano-phenyl)-amine;
{4-[2-acetylamino-4-(4-fluoro-phenyl)-thiazol-5-yl]-pyrimidin-2-yl}-N-(3-acetoxymethyl-phenyl)-amine;
N-[4-(2-amino-4-phenyl-thiazol-5-yl)-pyrimidin-2-yl]-N-(3-methoxy-phenyl)-amine;
N-{4-[2-amino-4-(4-fluoro-phenyl)-thiazol-5-yl]-pyrimidin-2-yl}-N-(3-methoxy-phenyl)-amine;
N-[4-(2-amino-4-phenyl-thiazol-5-yl)-pyrimidin-2-yl]-N-(3-cyano-phenyl)-amine;
N-[4-(2-amino-4-phenyl-thiazol-5-yl)-pyrimidin-2-yl]-N-(4-fluoro-phenyl)-amine;
N-{4-[2-amino-4-(4-fluoro-phenyl)-thiazol-5-yl]-pyrimidin-2-yl}-N-(3-cyano-phenyl)-amine;
N-[4-(2-amino-4-phenyl-thiazol-5-yl)-pyrimidin-2-yl]-N-(3-cyanomethyl-phenyl)-amine; and
N-{4-[2-amino-4-(4-fluoro-phenyl)-thiazol-5-yl]-pyrimidin-2-yl}-N-(3-cyanomethyl-phenyl)-amine.

11. A method according to claim 1, wherein the phytopathogenic microorganisms are fungal organisms.

* * * * *

UNITED STATES PATENT AND TRADEMARK OFFICE
CERTIFICATE OF CORRECTION

PATENT NO. : 7,105,517 B2
APPLICATION NO. : 10/491231
DATED : September 12, 2006
INVENTOR(S) : Mueller et al.

It is certified that error appears in the above-identified patent and that said Letters Patent is hereby corrected as shown below:

Col. 117, Line 5-35 Claim 1 of the above-identified patent should be deleted. Claims 2-11 in the patent should be renumbered as 1-10, respectively. Finally, claim 11 should be added to the patent as follows:

Col. 120, Line 61

11. A compound of formula IA

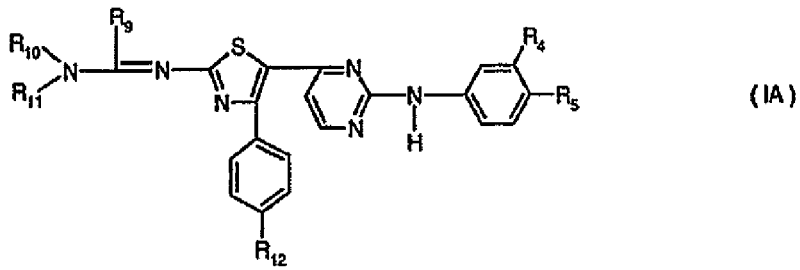

wherein $R_4$ is hydrogen, cyano, hydroxy, $C_1$-$C_4$alkoxy, $C_1$-$C_6$aminoalkyl, $C_1$-$C_8$alkanoyloxy-$C_1$-$C_4$alkyl, $C_1$-$C_8$alkanoylamino-$C_1$-$C_4$alkyl, $C_1$-$C_4$alkoxy-$C_1$-$C_6$alkyl, $C_1$-$C_6$hydroxyalkyl or $C_1$-$C_4$cyanoalkyl; $R_5$ is hydrogen, hydroxy, halogen, $C_1$-$C_6$alkyl, $C_1$-$C_6$alkoxy or $C_1$-$C_6$haloalkyl; $R_9$ is hydrogen, $C_1$-$C_6$alkyl, $C_1$-$C_6$haloalkyl, $C_3$-$C_7$cycloalkyl, $C_3$-$C_7$cycloalkyl-$C_1$-$C_4$alkyl, $C_1$-$C_4$alkyl-$C_3$-$C_7$cycloalkyl-$C_1$-$C_4$alkyl, aryl, aryl-$C_1$-$C_4$alkyl, heteroaryl or heteroaryl-$C_1$-$C_4$alkyl; $R_{10}$ is $C_1$-$C_6$alkyl, $C_1$-$C_6$haloalkyl, $C_3$-$C_7$cycloalkyl-$C_1$-$C_4$alkyl or $C_1$-$C_4$alkoxy-$C_1$-$C_6$alkyl; $R_{11}$ is $C_1$-$C_6$alkyl, $C_3$-$C_7$cycloalkyl, $C_3$-$C_7$cycloalkyl-$C_1$-$C_4$alkyl, $C_1$-$C_4$alkoxy-$C_1$-$C_6$alkyl, aryl or heteroaryl;

UNITED STATES PATENT AND TRADEMARK OFFICE
CERTIFICATE OF CORRECTION

PATENT NO. : 7,105,517 B2
APPLICATION NO. : 10/491231
DATED : September 12, 2006
INVENTOR(S) : Mueller et al.

It is certified that error appears in the above-identified patent and that said Letters Patent is hereby corrected as shown below:

and $R_{12}$ is halogen, $C_1$-$C_4$alkyl, $C_1$-$C_4$alkoxy, $C_1$-$C_4$haloalkyl or $C_1$-$C_4$haloalkoxy.

Signed and Sealed this

Twentieth Day of March, 2007

JON W. DUDAS
*Director of the United States Patent and Trademark Office*